(12) United States Patent
Waldraff et al.

(10) Patent No.: US 10,785,979 B2
(45) Date of Patent: Sep. 29, 2020

(54) SUBSTITUTED KETOXIME BENZOYLAMIDES

(71) Applicant: Bayer CropScience Aktiengesellschaft, Monheim am Rhein (DE)

(72) Inventors: Christian Waldraff, Bad Vilbel (DE); Ralf Braun, Ramberg (DE); Hansjoerg Dietrich, Liederbach am Taunus (DE); Elmar Gatzweiler, Bad Nauheim (DE); Christopher Hugh Rosinger, Hofheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/754,313

(22) PCT Filed: Aug. 22, 2016

(86) PCT No.: PCT/EP2016/069769
§ 371 (c)(1),
(2) Date: Feb. 22, 2018

(87) PCT Pub. No.: WO2017/032728
PCT Pub. Date: Mar. 2, 2017

(65) Prior Publication Data
US 2018/0235224 A1    Aug. 23, 2018

(30) Foreign Application Priority Data

Aug. 25, 2015 (EP) .................................. 15182355

(51) Int. Cl.
| | |
|---|---|
| *A01N 43/713* | (2006.01) |
| *C07D 249/14* | (2006.01) |
| *C07D 257/06* | (2006.01) |
| *A01N 43/653* | (2006.01) |
| *A01N 43/82* | (2006.01) |
| *C07D 271/08* | (2006.01) |
| *C07D 271/113* | (2006.01) |
| *C07D 271/06* | (2006.01) |
| *C07D 271/04* | (2006.01) |

(52) U.S. Cl.
CPC ......... *A01N 43/713* (2013.01); *A01N 43/653* (2013.01); *A01N 43/82* (2013.01); *C07D 249/14* (2013.01); *C07D 257/06* (2013.01); *C07D 271/04* (2013.01); *C07D 271/06* (2013.01); *C07D 271/08* (2013.01); *C07D 271/113* (2013.01)

(58) Field of Classification Search
CPC .. C07D 257/06; C07D 249/14; C07D 271/08; C07D 271/113; A01N 43/713
See application file for complete search history.

(56) References Cited

U.S. PATENT DOCUMENTS

| | | | |
|---|---|---|---|
| 6,028,035 | A | 2/2000 | Hill et al. |
| 8,957,096 | B2 | 2/2015 | Van Almsick et al. |
| 2014/0309112 | A1 | 10/2014 | Van Almsick et al. |
| 2018/0077935 | A1* | 3/2018 | Kohn .................... A01N 43/82 |

FOREIGN PATENT DOCUMENTS

| | | |
|---|---|---|
| DE | 197 00 096 A1 | 7/1998 |
| EP | 2 907 807 A1 | 8/2015 |
| WO | 2013/064459 A1 | 5/2013 |
| WO | 2015/052152 A1 | 4/2015 |
| WO | 2015/052153 A1 | 4/2015 |
| WO | WO 2016/146561 * | 9/2016 |

OTHER PUBLICATIONS

PCT International Search Report for PCT/EP2016/069769, dated Nov. 9, 2016.

\* cited by examiner

*Primary Examiner* — John Pak
(74) *Attorney, Agent, or Firm* — McBee Moore & Vanik IP, LLC

(57) ABSTRACT

What are described are substituted ketoxime benzoylamides of the general formula (I) as herbicides.

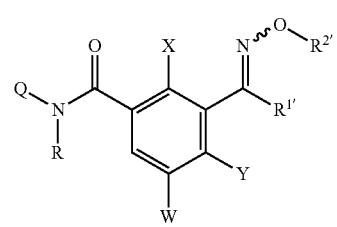

(I)

In this formula (I), $R^{1'}$, $R^{2'}$, X, Y and W are radicals such as hydrogen, organic radicals such as alkyl, and other radicals such as halogen. Q is an oxadiazole, tetrazole or triazole radical.

16 Claims, No Drawings

SUBSTITUTED KETOXIME BENZOYLAMIDES

CROSS-REFERENCE TO RELATED APPLICATIONS

This application is a National Stage entry of International Application No. PCT/EP2016/069769, filed Aug. 22, 2016, which claims priority to European Patent Application No. 15182355.6, filed Aug. 25, 2015.

BACKGROUND

Field

The invention relates to the technical field of the herbicides, especially that of the herbicides for selective control of weeds and weed grasses in crops of useful plants.

Description of Related Art

WO 2013/064459 A1 discloses aldoxime benzoylamides. WO 2015/052152 A1 and WO 2015/052153 A1 disclose ketoxime benzoylamides that are each substituted in the 6 position of the phenyl ring.

SUMMARY

It was an object of the present invention to provide further herbicidally active compounds.

It has now been found that particular substituted ketoxime benzoylamides are of particularly good suitability as herbicides.

The present invention thus provides substituted ketoxime benzoylamides of the formula (I)

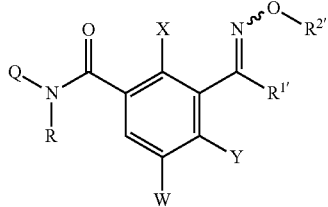

(I)

in which the symbols and indices are defined as follows:
Q is a Q1, Q2, Q3 or Q4 radical,

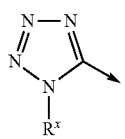

(Q1)

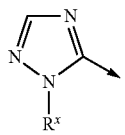

(Q2)

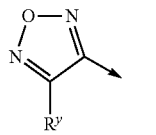

(Q3)

(Q4)

R is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $R^1(O)CO$—$(C_1-C_6)$-alkyl, $R^1O(O)C$—$O$—$(C_1-C_6)$-alkyloxy, $R^2(O)_2SO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $R^1(O)C$, $R^1O(O)C$, $(R^1)_2N(O)C$, $R^1O$, $(R^1)_2N$, $R^1O(O)C(R^1)N$, $(R^1)_2N(O)C(R^1)N$, $R^2(O)_2S$, or benzyl substituted in each case by s radicals from the group consisting of methyl, ethyl, methoxy, nitro, trifluoromethyl and halogen, $R^1$ is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N($R^3$)—$(C_1-C_6)$-alkyl, heteroaryl-N($R^3$)—$(C_1-C_6)$-alkyl, heterocyclyl-N($R^3$)—$(C_1-C_6)$-alkyl, phenyl-S(O)$_n$—$(C_1-C_6)$-alkyl, heteroaryl-S(O)$_n$—$(C_1-C_6)$-alkyl or heterocyclyl-S(O)$_n$—$(C_1-C_6)$-alkyl, where the fifteen latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1-C_6)$-alkyl, and where heterocyclyl bears n oxo groups, $R^2$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N($R^3$)—$(C_1-C_6)$-alkyl, heteroaryl-N($R^3$)—$(C_1-C_6)$-alkyl, heterocyclyl-N($R^3$)—$(C_1-C_6)$-alkyl, phenyl-S(O)$_n$—$(C_1-C_6)$-alkyl, heteroaryl-S(O)$_n$—$(C_1-C_6)$-alkyl or heterocyclyl-S(O)$_n$—$(C_1-C_6)$-alkyl, where the fifteen latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1-C_6)$-alkyl, and where heterocyclyl bears n oxo groups, $R^3$ is hydrogen, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ is $(C_1\text{-}C_6)$-alkyl, halo-$(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_6)$-alkyl or phenyl, $R^5$ is hydrogen or $(C_1\text{-}C_4)$-alkyl, $R^6$ is $(C_1\text{-}C_4)$-alkyl, $R^7$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, methylsulfenyl, methylsulfinyl, methylsulfonyl, $(C_3\text{-}C_6)$-cycloalkyl, or heteroaryl or heterocyclyl each substituted by s radicals from the group consisting of methyl, ethyl, methoxy, trifluoromethyl and halogen, $R^8$ is $(C_1\text{-}C_6)$-alkyl, halo-$(C_1\text{-}C_6)$-alkyl, $(C_1\text{-}C_6)$-alkyl-O—$(C_1\text{-}C_6)$-alkyl, $(C_2\text{-}C_6)$-alkenyl or $(C_3\text{-}C_6)$-alkynyl, $R^9$ is $(C_1\text{-}C_6)$-alkyl, halo-$(C_1\text{-}C_6)$-alkyl, $(C_2\text{-}C_6)$-alkenyl or $(C_3\text{-}C_6)$-alkynyl, $R^{10}$ is hydrogen, $(C_1\text{-}C_6)$-alkyl, halo-$(C_1\text{-}C_6)$-alkyl, $(C_2\text{-}C_6)$-alkenyl, $(C_2\text{-}C_6)$-alkynyl, $(C_3\text{-}C_6)$-cycloalkyl or $(C_3\text{-}C_6)$-cycloalkyl-$(C_1\text{-}C_6)$-alkyl, $R^{11}$ is $(C_1\text{-}C_6)$-alkyl, $(C_2\text{-}C_6)$-alkenyl or $(C_2\text{-}C_6)$-alkynyl, $R^{1'}$ is cyano, $(C_1\text{-}C_6)$-alkyl, $(C_3\text{-}C_6)$-cycloalkyl, halo-$(C_1\text{-}C_6)$-alkyl, $OR^8$, $SR^8$, $NR^8R^9$, $R^{2'}$ is hydrogen, $(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkenyl, $(C_3\text{-}C_6)$-cycloalkyl-$(C_1\text{-}C_6)$-alkyl, where the last six radicals are each substituted by s radicals from the group consisting of cyano, halogen, nitro, thiocyanato, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1\text{-}C_4)$-alkoxy-$(C_2\text{-}C_6)$-alkoxycarbonyl, or $R^{2'}$ is phenyl, phenyl-$(C_1\text{-}C_6)$-alkyl, heteroaryl, $(C_1\text{-}C_6)$-alkylheteroaryl, heterocyclyl, $(C_1\text{-}C_6)$-alkylheterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^{10}$-heteroaryl or $(C_1\text{-}C_6)$-alkyl-$NR^{10}$-heterocyclyl, where the ten latter radicals are each substituted by s radicals from the group consisting of cyano, halogen, nitro, thiocyanato, $(C_1\text{-}C_6)$-alkyl, halo-$(C_1\text{-}C_6)$-alkyl, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1\text{-}C_4)$-alkoxy-$(C_2\text{-}C_6)$-alkoxycarbonyl, and where heterocyclyl bears n oxo groups, $R^X$ is $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, where the six aforementioned radicals are each substituted by s radicals from the group consisting of nitro, cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)C$, $R^1(O)C(R^1)N$, $R^2(O)_2S(R^1)N$, $(C_3\text{-}C_6)$-cycloalkyl, heteroaryl, heterocyclyl and phenyl, where the four latter radicals themselves are in turn substituted by s radicals from the group consisting of $(C_1\text{-}C_6)$-alkyl, halo-$(C_1\text{-}C_6)$-alkyl, $(C_1\text{-}C_6)$-alkoxy, halo-$(C_1\text{-}C_6)$-alkoxy and halogen, and where heterocyclyl bears n oxo groups, or $R^X$ is $(C_3\text{-}C_7)$-cycloalkyl, heteroaryl, heterocyclyl or phenyl, where the four aforementioned radicals are each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $(C_1\text{-}C_6)$-alkyl-$S(O)_n$, $(C_1\text{-}C_6)$-alkoxy, halo-$(C_1\text{-}C_6)$-alkoxy and $(C_1\text{-}C_6)$-alkoxy-$(C_1\text{-}C_4)$-alkyl, $R^Y$ is hydrogen, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_7)$-cycloalkyl, $(C_1\text{-}C_6)$-alkoxy, halo-$(C_1\text{-}C_6)$-alkoxy, $(C_2\text{-}C_6)$-alkenyloxy, $(C_2\text{-}C_6)$-alkynyloxy, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by s radicals from the group consisting of $(C_1\text{-}C_6)$-alkyl, halo-$(C_1\text{-}C_6)$-alkyl, $(C_1\text{-}C_6)$-alkoxy, halo-$(C_1\text{-}C_6)$-alkoxy and halogen, and where heterocyclyl bears n oxo groups, $R^Z$ is hydrogen, $(C_1\text{-}C_6)$-alkyl, $R^1O$—$(C_1\text{-}C_6)$-alkyl, $R^7CH_2$, $(C_3\text{-}C_7)$-cycloalkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $R^1O$, $R^1(H)N$, methoxycarbonyl, ethoxycarbonyl, methylcarbonyl, dimethylamino, trifluoromethylcarbonyl, acetylamino, methylsulfenyl, methylsulfinyl, methylsulfonyl, or heteroaryl, heterocyclyl, benzyl or phenyl each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $(C_1\text{-}C_6)$-alkyl-$S(O)_n$, $(C_1\text{-}C_6)$-alkoxy, halo-$(C_1\text{-}C_6)$-alkoxy and $(C_1\text{-}C_6)$-alkoxy-$(C_1\text{-}C_4)$-alkyl, where heterocyclyl bears n oxo groups, W is hydrogen, halogen, nitro, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_7)$-cycloalkyl, halo-$(C_3\text{-}C_7)$-cycloalkyl, $(C_1\text{-}C_6)$-alkoxy, halo-$(C_1\text{-}C_6)$-alkoxy, $(C_1\text{-}C_6)$-alkyl-$(O)_nS$—, $(C_1\text{-}C_6)$-haloalkyl-$(O)_nS$—, $(C_1\text{-}C_6)$-alkoxy-$(C_1\text{-}C_4)$-alkyl, $(C_1\text{-}C_6)$-alkoxy-$(C_1\text{-}C_4)$-haloalkyl, $R^1(O)C$, $R^1(R^1ON=)C$, $R^1O(O)C$, $(R^1)_2N$, $R^1(O)C(R^1)N$ or $R^2(O)_2S(R^1)N$, X is nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $R^1(O)C$, $R^1(R^1ON=)C$, $R^1O(O)C$, $(R^1)_2N(O)C$, $R^1(R^1)N(O)C$, $(R^1)_2N(R^1)N(O)C$, $R^1(O)C(R^1)N(O)C$, $R^1O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^1O(O)CO$, $(R^1)_2N(O)CO$, $(R^1)_2N$, $R^1(O)C(R^1)N$, $R^2(O)_2S(R^1)N$, $R^1O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^1O(O)C(R^1)N(O)_2S$, $(R^1)_2N(O)C(R^1)N(O)_2S$, $(R^5O)_2(O)P$, $R^1(O)C$—$(C_1\text{-}C_6)$-alkyl, $R^1O(O)C$—$(C_1\text{-}C_6)$-alkyl, $(R^1)_2N(O)C$—$(C_1\text{-}C_6)$-alkyl, $(R^1)(R^1)N(O)C$—$(C_1\text{-}C_6)$-alkyl, $(R^1)_2N(R^1)N(O)C$—$(C_1\text{-}C_6)$-alkyl, $R^1(O)C(R^1)N(O)C$—$(C_1\text{-}C_6)$-alkyl, $R^1O(O)C(R^1)N(O)C$—$(C_1\text{-}C_6)$-alkyl, $(R^1)_2N(O)C(R^1)N(O)C$—$(C_1\text{-}C_6)$-alkyl, $R^2(O)_2S(R^1)N(O)C$—$(C_1\text{-}C_6)$-alkyl, $R^1O(O)_2S(R^1)N(O)C$—$(C_1\text{-}C_6)$-alkyl, $(R^1)_2N(O)_2S(R^1)N(O)C$—$(C_1\text{-}C_6)$-alkyl, NC—$(C_1\text{-}C_6)$-alkyl, $R^1O$—$(C_1\text{-}C_6)$-alkyl, $R^1(O)CO$—$(C_1\text{-}C_6)$-alkyl, $R^2(O)_2SO$—$(C_1\text{-}C_6)$-alkyl, $R^1O(O)CO$—$(C_1\text{-}C_6)$-alkyl, $(R^1)_2N(O)CO$—$(C_1\text{-}C_6)$-alkyl, $(R^1)_2N$—$(C_1\text{-}C_6)$-alkyl, $R^1(O)C(R^1)N$—$(C_1\text{-}C_6)$-alkyl, $R^2(O)_2S(R^1)N$—$(C_1\text{-}C_6)$-alkyl, $R^1O(O)C(R^1)N$—$(C_1\text{-}C_6)$-alkyl, $(R^1)_2N(O)C(R^1)N$—$(C_1\text{-}C_6)$-alkyl, $R^1O(O)_2S(R^1)N$—$(C_1\text{-}C_6)$-alkyl, $(R^1)_2N(O)_2S(R^1)N$—$(C_1\text{-}C_6)$-alkyl, $R^2(O)_nS$—$(C_1\text{-}C_6)$-alkyl, $R^1O(O)_2S$—$(C_1\text{-}C_6)$-alkyl, $(R^1)_2N(O)_2S$—$(C_1\text{-}C_6)$-alkyl, $R^1(O)C(R^1)N(O)_2S$—$(C_1\text{-}C_6)$-alkyl, $R^1O(O)C(R^1)N(O)_2S$—$(C_1\text{-}C_6)$-alkyl, $(R^1)_2N(O)C(R^1)N(O)_2S$—$(C_1\text{-}C_6)$-alkyl, $(R^5O)_2(O)P$—$(C_1\text{-}C_6)$-alkyl, phenyl, heteroaryl, heterocyclyl, phenyl-$(C_1\text{-}C_6)$-alkyl, heteroaryl-$(C_1\text{-}C_6)$-alkyl, heterocyclyl-$(C_1\text{-}C_6)$-alkyl, where the six latter radicals are each substituted by s radicals from the group consisting of nitro, halogen, cyano, thiocyanato, $(C_1\text{-}C_6)$-alkyl, halo-$(C_1\text{-}C_6)$-alkyl, $(C_3\text{-}C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1\text{-}C_6)$-alkyl, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1(R^1)N(O)C$, $(R^1)_2N(R^1)N(O)C$, $R^1(O)C(R^1)N(O)C$, $R^1O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^1O(O)CO$, $(R^1)_2N(O)CO$, $(R^1)_2N$, $R^1(O)C(R^1)N$, $R^2(O)_2S(R^1)N$, $R^1O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^1O(O)C(R^1)N(O)_2S$, $(R^1)_2N(O)C(R^1)N(O)_2S$, $(R^5O)_2(O)P$, $R^1(O)C—(C_1-C_6)$-alkyl, $R^1O(O)C—(C_1-C_6)$-alkyl, $(R^1)_2N(O)C—(C_1-C_6)$-alkyl, $(R^1)(R^1)N(O)C—(C_1-C_6)$-alkyl, $(R^1)_2N(R^1)N(O)C—(C_1-C_6)$-alkyl, $R^1(O)C(R^1)N(O)C—(C_1-C_6)$-alkyl, $R^1O(O)C(R^1)N(O)C—(C_1-C_6)$-alkyl, $(R^1)_2N(O)C(R^1)N(O)C—(C_1-C_6)$-alkyl, $R^2(O)_2S(R^1)N(O)C—(C_1-C_6)$-alkyl, $R^1O(O)_2S(R^1)N(O)C—(C_1-C_6)$-alkyl, $(R^1)_2N(O)_2S(R^1)N(O)C—(C_1-C_6)$-alkyl, $NC—(C_1-C_6)$-alkyl, $R^1O—(C_1-C_6)$-alkyl, $R^1(O)CO—(C_1-C_6)$-alkyl, $R^2(O)_2SO—(C_1-C_6)$-alkyl, $R^1O(O)CO—(C_1-C_6)$-alkyl, $(R^1)_2N(O)CO—(C_1-C_6)$-alkyl, $(R^1)_2N—(C_1-C_6)$-alkyl, $R^1(O)C(R^1)N—(C_1-C_6)$-alkyl, $R^2(O)_2S(R^1)N—(C_1-C_6)$-alkyl, $R^1O(O)C(R^1)N—(C_1-C_6)$-alkyl, $(R^1)_2N(O)C(R^1)N—(C_1-C_6)$-alkyl, $R^1O(O)_2S(R^1)N—(C_1-C_6)$-alkyl, $(R^1)_2N(O)_2S(R^1)N—(C_1-C_6)$-alkyl, $R^2(O)_nS—(C_1-C_6)$-alkyl, $R^1O(O)_2S—(C_1-C_6)$-alkyl, $(R^1)_2N(O)_2S—(C_1-C_6)$-alkyl, $R^1(O)C(R^1)N(O)_2S—(C_1-C_6)$-alkyl, $R^1O(O)C(R^1)N(O)_2S—(C_1-C_6)$-alkyl, $(R^1)_2N(O)C(R^1)N(O)_2S—(C_1-C_6)$-alkyl, $(R^5O)_2(O)P—(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O—(C_1-C_6)$-alkyl, and where heterocyclyl bears n oxo groups, n is 0, 1 or 2, s is 0, 1, 2 or 3.

DETAILED DESCRIPTION OF A PREFERRED EMBODIMENT

Preference is given to compounds of the general formula (I) in which the symbols and indices are defined as follows:
Q is a Q1, Q2, Q3 or Q4 radical,

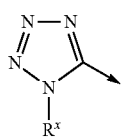 (Q1)

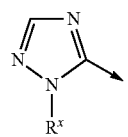 (Q2)

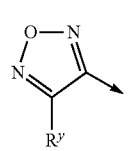 (Q3)

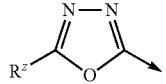 (Q4)

R is hydrogen, $(C_1-C_6)$-alkyl, halo-$(C_1-C_6)$-alkyl, $R^1(O)C—(C_1-C_6)$-alkyl, $R^1O(O)C—(C_1-C_6)$-alkyl, $R^1O(O)C—O—(C_1-C_6)$-alkyloxy, $R^1O—(C_1-C_6)$-alkyl, $R^1(O)C$, $R^1O(O)C$, $R^1O$, $R^2(O)_2S$, or benzyl substituted in each case by s radicals from the group consisting of methyl, ethyl, methoxy, nitro, trifluoromethyl and halogen, $R^1$ is hydrogen, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_1-C_6)$-alkyl-O—$(C_1-C_6)$-alkyl, phenyl, heteroaryl or heterocyclyl, where the three latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O—(C_1-C_6)$-alkyl, and where heterocyclyl bears n oxo groups, $R^2$ is $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_1-C_6)$-alkyl-O—$(C_1-C_6)$-alkyl, phenyl, heteroaryl or heterocyclyl, where the three latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O—(C_1-C_6)$-alkyl, and where heterocyclyl bears n oxo groups, $R^3$ is hydrogen, $(C_1-C_6)$-alkyl, halo-$(C_1-C_6)$-alkyl, $(C_3-C_6)$-cycloalkyl or phenyl, $R^4$ is $(C_1-C_6)$-alkyl, halo-$(C_1-C_6)$-alkyl, $(C_3-C_6)$-cycloalkyl or phenyl, $R^5$ is hydrogen or $(C_1-C_4)$-alkyl, $R^6$ is $(C_1-C_4)$-alkyl, $R^7$ is acetoxy, benzoyloxy, methoxycarbonyl, ethoxycarbonyl, methylcarbonyl, trifluoromethylcarbonyl, methylsulfenyl, methylsulfinyl, methylsulfonyl, $(C_3-C_6)$-cycloalkyl, or heteroaryl or heterocyclyl each substituted by s radicals from the group consisting of methyl, ethyl, methoxy, trifluoromethyl and halogen, $R^8$ is $(C_1-C_6)$-alkyl, halo-$(C_1-C_6)$-alkyl, $(C_1-C_6)$-alkyl-O—$(C_1-C_6)$-alkyl, $(C_2-C_6)$-alkenyl or $(C_3-C_6)$-alkynyl, $R^9$ is $(C_1-C_6)$-alkyl or halo-$(C_1-C_6)$-alkyl, $R^{10}$ is hydrogen, $(C_1-C_6)$-alkyl, halo-$(C_1-C_6)$-alkyl or $(C_3-C_6)$-cycloalkyl, $R^{11}$ is $(C_1-C_6)$-alkyl, $R^{1'}$ is $(C_1-C_6)$-alkyl, $(C_3-C_6)$-cycloalkyl, halo-$(C_1-C_6)$-alkyl, $OR^8$, $SR^8$ or $NR^8R^9$, $R^{2'}$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, where the last six radicals are each substituted by s radicals from the group consisting of cyano, halogen, $OR^{10}$, $S(O)_nR^{11}$, $N(R^{10})_2$, $COR^{10}$, $CO_2R^{10}$ and $(C_1-C_4)$-alkoxy-$(C_2-C_6)$-alkoxycarbonyl, or $R^{2'}$ is phenyl, heteroaryl, heterocyclyl, where the three latter radicals are each substituted by s radicals from the group consisting of cyano, halogen, nitro, thiocyanato, $(C_1-C_6)$-alkyl, halo-$(C_1-C_6)$-alkyl, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1-C_4)$-alkoxy-$(C_2-C_6)$-alkoxycarbonyl, and where heterocyclyl bears n oxo groups, $R^x$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, where the five aforementioned radicals are each substituted by s radicals from the group consisting of cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)CO$, $(C_3-C_6)$-cycloalkyl, heteroaryl, heterocyclyl and phenyl, where the four latter radicals themselves are in turn substituted by s radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl bears n oxo groups, or $R^X$ is $(C_3-C_7)$-cycloalkyl, heteroaryl, heterocyclyl or phenyl, where the four aforementioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkyl-$S(O)_n$, $(C_1-C_6)$-alkoxy, halo-$(C_1-C_6)$-alkoxy and $(C_1-C_6)$-alkoxy-$(C_1-C_4)$-alkyl, $R^Y$ is hydrogen, $(C_1-C_6)$-alkyl, halo-$(C_1-C_6)$-alkyl, $(C_2-C_6)$-alkenyl, $(C_2-C_6)$-alkynyl, $(C_3-C_7)$-cycloalkyl, $(C_1-C_6)$-alkoxy, cyano, methylsulfenyl, methylsulfinyl, methylsulfonyl, acetylamino, methoxycarbonyl, ethoxycarbonyl, methoxycarbonylmethyl, ethoxycarbonylmethyl, benzoyl, methylcarbonyl, trifluoromethylcarbonyl, halogen, amino, methylaminocarbonyl, dimethylaminocarbonyl, methoxymethyl, or heteroaryl, heterocyclyl or phenyl each substituted by s radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl bears n oxo groups, $R^Z$ is hydrogen, $(C_1-C_6)$-alkyl, $R^1O$—$(C_1-C_6)$-alkyl, $R^7CH_2$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, $R^1O$, $R^1(H)N$, methoxycarbonyl, ethoxycarbonyl, methylcarbonyl, dimethylamino, trifluoromethylcarbonyl, acetylamino, methylsulfenyl, methylsulfinyl, methylsulfonyl, or heteroaryl, heterocyclyl, benzyl or phenyl each substituted by s radicals from the group consisting of halogen, cyano, $(C_1-C_6)$-alkyl, halo-$(C_1-C_6)$-alkyl, $(C_3-C_6)$-cycloalkyl, $(C_1-C_6)$-alkyl-$S(O)_n$, $(C_1-C_6)$-alkoxy, halo-$(C_1-C_6)$-alkoxy and $(C_1-C_6)$-alkoxy-$(C_1-C_4)$-alkyl, where heterocyclyl bears n oxo groups, W is hydrogen, halogen, $(C_1-C_6)$-alkyl, halo-$(C_1-C_6)$-alkyl, $(C_2-C_6)$-alkenyl, $(C_2-C_6)$-alkynyl, $(C_3-C_7)$-cycloalkyl, $(C_1-C_6)$-alkoxy, halo-$(C_1-C_6)$-alkoxy, $(C_1-C_6)$-alkyl-$(O)_nS$—, $(C_1-C_6)$-alkoxy-$(C_1-C_4)$-alkyl, $(C_1-C_6)$-alkoxy-$(C_1-C_4)$-haloalkyl, $R^1(O)C$, $(R^1)_2N$, $R^1(O)C(R^1)N$ or $R^2(O)_2S(R^1)N$, X is nitro, halogen, cyano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $R^1(O)CO$, $R^1O(O)CO$, $(R^1)_2N$, $R^1(O)C(R^1)N$, $R^2(O)_2S(R^1)N$, $R^1O(O)C(R^1)N$, $R^2(O)_nS$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $NC$—$(C_1-C_6)$-alkyl, $R^1O$—$(C_1-C_6)$-alkyl, $R^1(O)CO$—$(C_1-C_6)$-alkyl, $R^2(O)_2SO$—$(C_1-C_6)$-alkyl, $R^1O(O)CO$—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^1O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $(R^5O)_2(O)P$—$(C_1-C_6)$-alkyl, phenyl, heteroaryl, heterocyclyl, where the three latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $R^1(O)CO$, $R^2(O)_2SO$, $R^1O(O)CO$, $(R^1)_2N(O)CO$, $(R^1)_2N$, $R^1(O)C(R^1)N$, $R^2(O)_2S(R^1)N$, $R^1O(O)C(R^1)N$, $R^2(O)_nS$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $NC$—$(C_1-C_6)$-alkyl, $R^1O$—$(C_1-C_6)$-alkyl, $R^1(O)CO$—$(C_1-C_6)$-alkyl, $R^2(O)_2SO$—$(C_1-C_6)$-alkyl, $R^1O(O)CO$—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^1O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $(R^5O)_2(O)P$—$(C_1-C_6)$-alkyl, phenyl, heteroaryl, heterocyclyl, where the three latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, n is 0, 1 or 2, s is 0, 1, 2 or 3.

Particular preference is given to compounds of the general formula (I) in which the symbols and indices are defined as follows:

Q is a Q1, Q2, Q3 or Q4 radical,

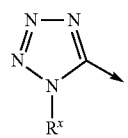

(Q1)

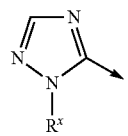

(Q2)

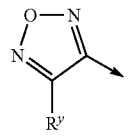

(Q3)

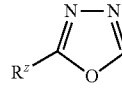

(Q4)

R is hydrogen, $(C_1-C_6)$-alkyl, halo-$(C_1-C_6)$-alkyl, $R^1(O)C$—$(C_1-C_6)$-alkyl, $R^1O(O)C$—$O$—$(C_1-C_6)$-alkyloxy, $R^1(O)C$, $R^1O(O)C$ or $R^2(O)_2S$, $R^1$ is hydrogen, $(C_1-C_6)$-alkyl, halo-$(C_1-C_6)$-alkyl, $(C_3-C_6)$-cycloalkyl, $(C_1-C_6)$-alkyl-$O$—$(C_1-C_6)$-alkyl, phenyl, heteroaryl or heterocyclyl, where the three latter radicals are each substituted by s radicals from the group consisting of halogen, $(C_1-C_6)$-alkyl, halo-$(C_1-C_6)$-alkyl and $R^3O(O)C$, and where heterocyclyl bears n oxo groups, $R^2$ is $(C_1-C_6)$-alkyl, halo-$(C_1-C_6)$-alkyl, $(C_3-C_6)$-cycloalkyl, $(C_1-C_6)$-alkyl-$O$—$(C_1-C_6)$-alkyl, phenyl, heteroaryl or heterocyclyl, where the three latter radicals are each substituted by s radicals from the group consisting of halogen, $(C_1-C_6)$-alkyl, halo-$(C_1-C_6)$-alkyl, $R^3O(O)C$, $R^3O$, $R^4(O)_nS$ and $R^3O$—$(C_1-C_6)$-alkyl, and where heterocyclyl bears n oxo groups, R³ is hydrogen, (C₁-C₆)-alkyl or halo-(C₁-C₆)-alkyl,
R⁴ is (C₁-C₆)-alkyl or halo-(C₁-C₆)-alkyl,
R⁵ is hydrogen or (C₁-C₄)-alkyl,
R⁶ is (C₁-C₄)-alkyl,
R⁷ is acetoxy, methylsulfenyl or (C₃-C₆)-cycloalkyl,
R⁸ is (C₁-C₆)-alkyl or halo-(C₁-C₆)-alkyl,
R⁹ is (C₁-C₆)-alkyl,
R¹⁰ is hydrogen, (C₁-C₆)-alkyl or halo-(C₁-C₆)-alkyl,
R¹¹ is (C₁-C₆)-alkyl,
R¹' is (C₁-C₆)-alkyl, (C₃-C₆)-cycloalkyl, halo-(C₁-C₆)-alkyl, OR⁸, SR⁸, NR⁸R⁹,
R²' is hydrogen, (C₁-C₆)-alkyl, (C₃-C₆)-cycloalkyl, (C₃-C₆)-cycloalkyl-(C₁-C₆)-alkyl, where the last three radicals are each substituted by s radicals from the group consisting of cyano, halogen, OR¹⁰, S(O)ₙR¹¹, N(R¹⁰)₂, COR¹⁰, CO₂R¹⁰ and (C₁-C₄)-alkoxy-(C₂-C₆)-alkoxycarbonyl,
or R²' is phenyl, heteroaryl, heterocyclyl, where the three latter radicals are each substituted by s radicals from the group consisting of cyano, halogen, (C₁-C₆)-alkyl, halo-(C₁-C₆)-alkyl, OR¹⁰, S(O)ₙR¹¹, N(R¹⁰)₂, COR¹⁰ and CO₂R¹⁰, and where heterocyclyl bears n oxo groups,
Rˣ is (C₁-C₆)-alkyl, halo-(C₁-C₆)-alkyl, (C₂-C₆)-alkenyl, (C₂-C₆)-alkynyl, where the four aforementioned radicals are each substituted by s radicals from the group consisting of cyano, (R⁶)₃Si, (R⁵O)₂(O)P, R²(O)ₙS, (R¹)₂N, R¹O, R¹(O)C, R¹O(O)C, (C₃-C₆)-cycloalkyl, heteroaryl, heterocyclyl and phenyl, where the four latter radicals themselves are in turn substituted by s radicals from the group consisting of (C₁-C₆)-alkyl, halo-(C₁-C₆)-alkyl, (C₁-C₆)-alkoxy, halo-(C₁-C₆)-alkoxy and halogen, and where heterocyclyl bears n oxo groups,
or Rˣ is (C₃-C₇)-cycloalkyl, heteroaryl, heterocyclyl or phenyl, where the four aforementioned radicals are each substituted by s radicals from the group consisting of halogen, cyano, (C₁-C₆)-alkyl, halo-(C₁-C₆)-alkyl, (C₃-C₆)-cycloalkyl, (C₁-C₆)-alkyl-S(O)ₙ, (C₁-C₆)-alkoxy, halo-(C₁-C₆)-alkoxy and (C₁-C₆)-alkoxy-(C₁-C₄)-alkyl,
Rʸ is hydrogen, (C₁-C₆)-alkyl, halo-(C₁-C₆)-alkyl, (C₂-C₆)-alkenyl, (C₂-C₆)-alkynyl, (C₃-C₇)-cycloalkyl, (C₁-C₆)-alkoxy, methylsulfenyl, methylsulfinyl, methylsulfonyl, acetylamino, methoxycarbonyl, ethoxycarbonyl, methoxycarbonylmethyl, ethoxycarbonylmethyl, benzoyl, methylcarbonyl, trifluoromethylcarbonyl, halogen, methoxymethyl, or phenyl substituted in each case by s radicals from the group consisting of (C₁-C₆)-alkyl, halo-(C₁-C₆)-alkyl, (C₁-C₆)-alkoxy, halo-(C₁-C₆)-alkoxy and halogen,
Rᶻ is hydrogen, (C₁-C₆)-alkyl, R¹O—(C₁-C₆)-alkyl, R⁷CH₂, (C₃-C₇)-cycloalkyl, halo-(C₁-C₆)-alkyl, (C₂-C₆)-alkenyl, halo-(C₂-C₆)-alkenyl, (C₂-C₆)-alkynyl, R¹O, R¹(H)N, methoxycarbonyl, ethoxycarbonyl, methylcarbonyl, dimethylamino, trifluoromethylcarbonyl, acetylamino, methylsulfenyl, methylsulfinyl, methylsulfonyl, or phenyl substituted in each case by s radicals from the group consisting of halogen, cyano, (C₁-C₆)-alkyl, halo-(C₁-C₆)-alkyl, (C₃-C₆)-cycloalkyl, (C₁-C₆)-alkyl-S(O)ₙ, (C₁-C₆)-alkoxy and halo-(C₁-C₆)-alkoxy,
W is hydrogen, halogen, (C₁-C₆)-alkyl, halo-(C₁-C₆)-alkyl, (C₃-C₇)-cycloalkyl, (C₁-C₆)-alkoxy, halo-(C₁-C₆)-alkoxy, (C₁-C₆)-alkyl-S(O)ₙ or (C₁-C₆)-alkoxy-(C₁-C₄)-alkyl,
X is halogen, (C₁-C₆)-alkyl, halo-(C₁-C₆)-alkyl, (C₃-C₆)-cycloalkyl, R¹(O)C, R¹O(O)C, (R¹)₂N(O)C, R¹O, (R¹)₂N, R²(O)ₙS, R¹O—(C₁-C₆)-alkyl, (R¹)₂N—(C₁-C₆)-alkyl, R²(O)ₙS—(C₁-C₆)-alkyl, phenyl, where the latter radical is substituted in each case by s radicals from the group consisting of halogen, (C₁-C₆)-alkyl, halo-(C₁-C₆)-alkyl, R¹O(O)C, R¹O, (R¹)₂N, R²(O)ₙS and R¹O—(C₁-C₆)-alkyl, Y is hydrogen, halogen, cyano, (C₁-C₆)-alkyl, halo-(C₁-C₆)-alkyl, (C₂-C₆)-alkenyl, (C₂-C₆)-alkynyl, (C₃-C₆)-cycloalkyl, halo-(C₃-C₆)-cycloalkyl, (C₃-C₆)-cycloalkyl-(C₁-C₆)-alkyl, R¹(O)C, R¹O(O)C, R¹O, (R¹)₂N, R²(O)ₙS, (R⁵O)₂(O)P, R¹O—(C₁-C₆)-alkyl, (R¹)₂N—(C₁-C₆)-alkyl, R²(O)ₙS—(C₁-C₆)-alkyl, phenyl, where the latter radical is substituted in each case by s radicals from the group consisting of halogen, (C₁-C₆)-alkyl, halo-(C₁-C₆)-alkyl, R¹O(O)C, R¹O, (R¹)₂N, R²(O)ₙS and R¹O—(C₁-C₆)-alkyl,
n is 0, 1 or 2,
s is 0, 1, 2 or 3.

Very particular preference is given to compounds of the general formula (I) in which the symbols and indices are defined as follows:
Q is a Q1, Q2, Q3 or Q4 radical,

(Q1)

(Q2)

(Q3)

(Q4)

R is hydrogen,
R¹' is methyl, ethyl, trifluoromethyl or cyclopropyl,
R²' is methyl, ethyl, 2,2,2-trifluoroethyl, cyclopropylmethyl or trifluoromethyl,
Rˣ is methyl, ethyl, propyl, methoxyethyl, 2-methoxy-2-methyl-1-propyl or phenyl,
Rʸ is chlorine, methyl or ethyl,
Rᶻ is chlorine, methyl or ethyl,
X is fluorine, chlorine, bromine, methyl, methoxy, methylsulfonyl, methoxymethyl, methylsulfenyl, trifluoromethyl or cyclopropyl,
Y is chlorine, methyl, ethyl, cyclopropyl, allyl, vinyl, trifluoromethyl, difluoromethyl, chlorodifluoromethyl, pentafluoroethyl, methoxy, methylsulfenyl, methylsulfinyl, methylsulfonyl or ethylsulfonyl,
W is hydrogen, fluorine, chlorine, methyl or trifluoromethyl.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical.

Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this should be understood to mean that this group is substituted by one or more identical or different radicals selected from the radicals mentioned. The same applies to the formation of ring systems by different atoms and elements.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically. Owing to the oxime ether structure, the compounds of the invention may also occur as geometric isomers (E/Z isomers). The invention also relates to all E/Z isomers and mixtures thereof which are encompassed by the general formula (I) but not defined specifically. In general, the E isomers occur in excess.

Inventive compounds in which Q is Q1 or Q2 can be prepared, for example, by the method shown in scheme 1, by base-catalyzed reaction of a benzoyl chloride (II) with a 5-amino-1H-1,2,4-triazole or 5-amino-1H-tetrazole (III):

Scheme 1

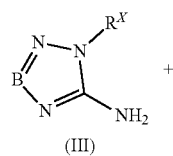

(III)

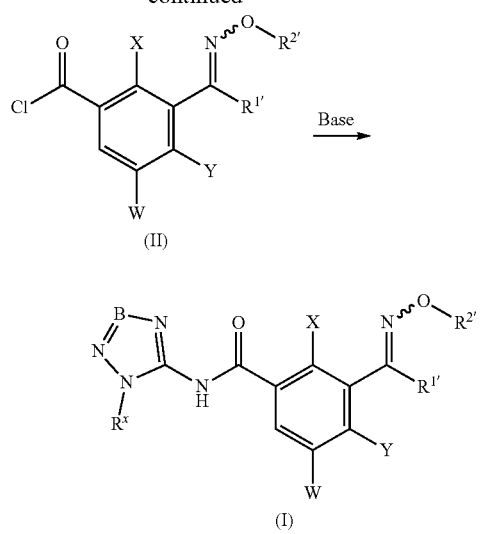

B therein is CH or N. The benzoyl chlorides of the formula (II) or their parent benzoic acids are known in principle and can be prepared, for example, by the methods described in WO 98/29392 and WO 98/29384, or in JP 11021274 and WO 98/45273. In the synthesis of these benzoyl chlorides, or their parent benzoic acids, according to the synthesis regime or substitution patterns, only one of the two possible isomers (E or Z isomer) or else E/Z mixtures may arise. For the syntheses of the inventive compounds (I), it is possible to use such E/Z mixtures, in which case the compounds of type I can be isolated in isomerically pure form after the workup or in the purification. Alternatively, the E/Z mixtures, for example of the benzoic acids, are separated by means of preparative HPLC in order then to convert the isomers individually to the benzoylamides (I) of the invention.

Inventive compounds in which Q is Q1 or Q2 can also be prepared by the method shown in scheme 2, by reaction of a benzoic acid of the formula (IV) with a 5-amino-(1H-1,2,4-triazole or 5-amino-1H-tetrazole (III):

Scheme 2

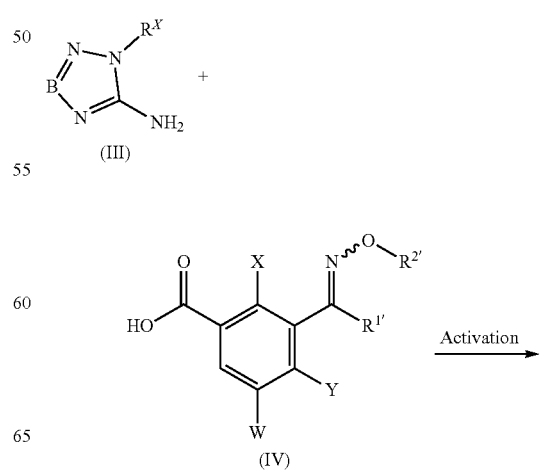

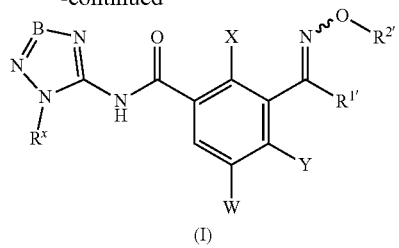

(I)

For the activation, it is possible to use dehydrating reagents which are typically for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

Inventive compounds in which Q is Q1 or Q2 can also be prepared by the method shown in scheme 3, by conversion of an N-(1H-1,2,4-triazol-5-yl)benzamide or of an N-(1H-tetrazol-5-yl)benzamide:

Scheme 3

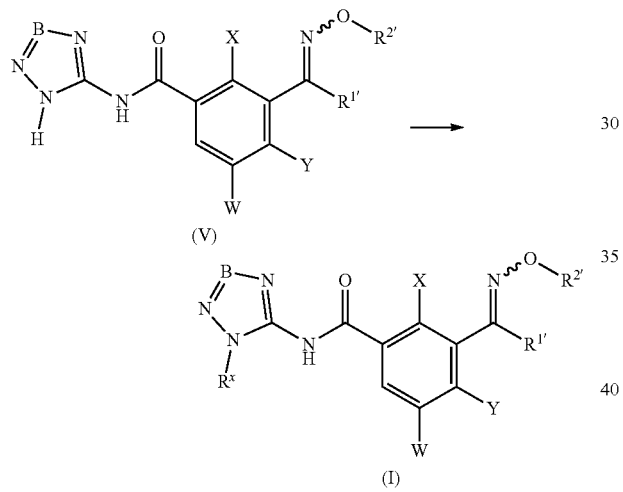

For this reaction shown in scheme 3, it is possible, for example, to use alkylating agents, for example alkyl halides or sulfonates or dialkyl sulfates, in the presence of a base.

The 5-amino-1H-tetrazoles of the formula (III) are either commercially available or can be prepared analogously to methods known from the literature. For example, substituted 5-aminotetrazoles can be prepared from aminotetrazole by the method described in Journal of the American Chemical Society (1954), 76, 923-924:

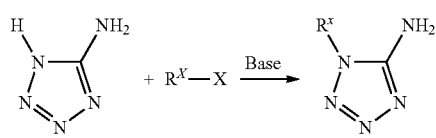

In the above reaction, X is a leaving group such as iodine. Substituted 5-aminotetrazoles can also be synthesized, for example, as described in Journal of the American Chemical Society (1954) 76, 88-89:

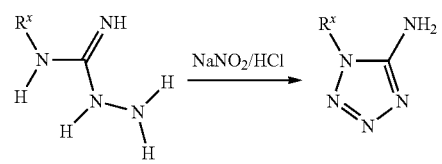

The 5-amino-1H-triazoles of the formula (III) are either commercially available or can be prepared analogously to methods known from the literature. For example, substituted 5-aminotriazoles can be prepared from aminotriazole by the method described in Zeitschrift für Chemie (1990), 30(12), 436-437:

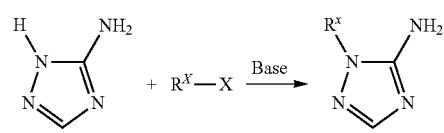

Substituted 5-aminotriazoles can also be synthesized, for example, as described in Chemische Berichte (1964), 97(2), 396-404:

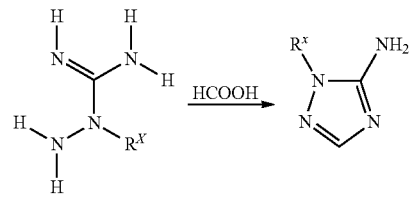

Substituted 5-aminotriazoles can also be synthesized, for example, as described in Angewandte Chemie (1963), 75, 918:

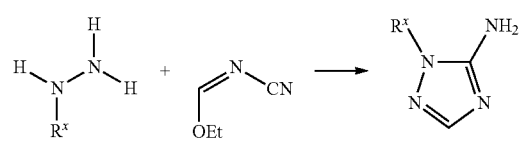

Inventive compounds in which Q is Q3 can be prepared, for example, by the method shown in scheme 4, by base-catalyzed reaction of a benzoyl chloride (II) with a 4-amino-1,2,5-oxadiazole (VI):

Scheme 4

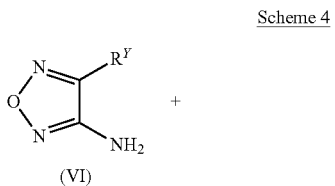

(VI)

-continued

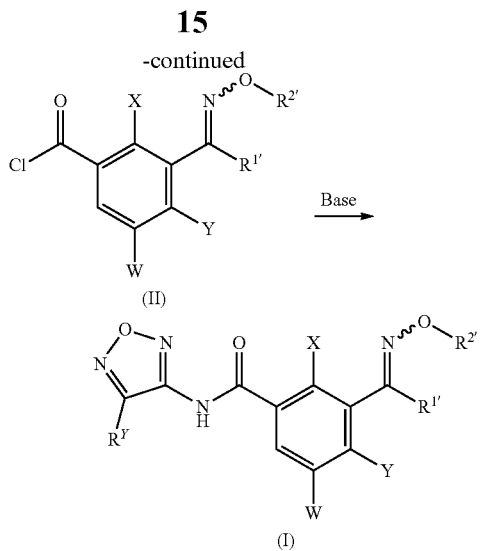

Compounds according to the invention can also be prepared by the method described in scheme 5, by reacting a benzoic acid of the formula (IV) with a 4-amino-1,2,5-oxadiazole (VI):

Scheme 5

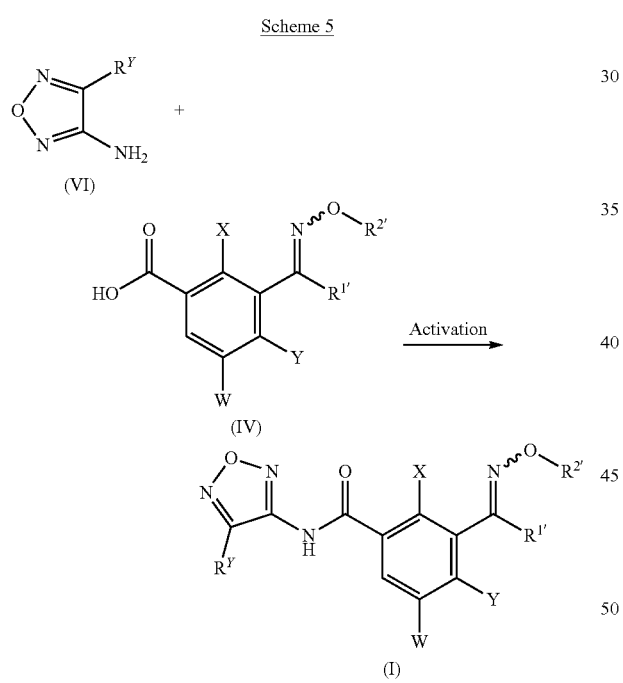

For the activation, it is possible to use dehydrating reagents which are typically for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

The 4-amino-1,2,5-oxadiazoles of the formula (VI) are either commercially available or known, or can be prepared analogously to methods known from the literature.

For example, 3-alkyl-4-amino-1,2,5-oxadiazoles can be prepared from β-keto esters by the method described in Russian Chemical Bulletin, Int. Ed., vol. 54, no. 4, p. 1032-1037 (2005):

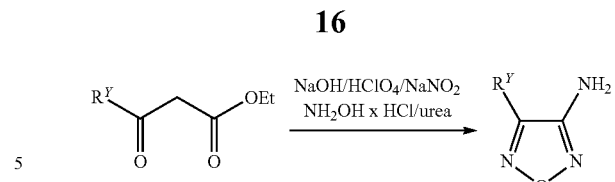

3-Aryl-4-amino-1,2,5-oxadiazoles can be synthesized, for example, as described in Russian Chemical Bulletin, 54(4), 1057-1059, (2005) or Indian Journal of Chemistry, Section B: Organic Chemistry Including Medicinal Chemistry, 26B (7), 690-2, (1987):

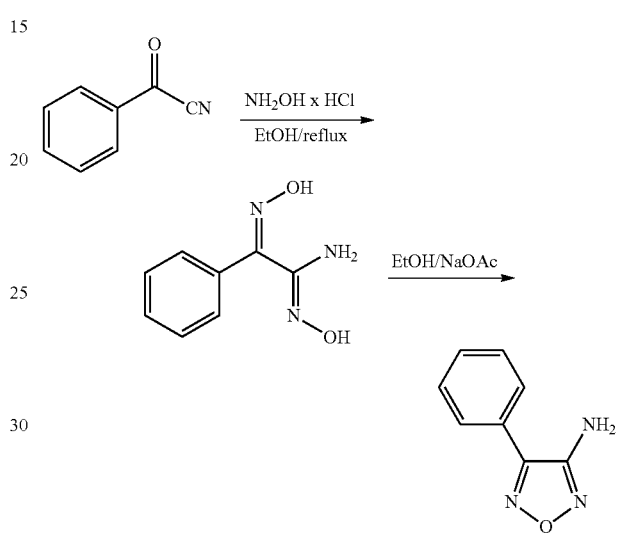

3-Amino-4-halo-1,2,5-oxadiazoles can be prepared, for example, by a Sandmeyer reaction from the commercially available 3,4-diamino-1,2,5-oxadiazole, according to the method described in Heteroatom Chemistry 15(3), 199-207 (2004):

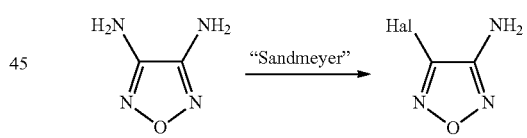

Nucleophilic $R^Y$ radicals can be introduced into 3-amino-1,2,5-oxadiazoles by substitution of the leaving group L as described in Journal of Chemical Research, Synopses, (6), 190, 1985 or in or Izvestiya Akademii Nauk SSSR, Seriya Khimicheskaya, (9), 2086-8, 1986 or in Russian Chemical Bulletin (Translation of Izvestiya Akademii Nauk, Seriya Khimicheskaya), 53(3), 596-614, 2004. L is a leaving group, for example chlorine, bromine, iodine, mesyloxy, tosyloxy, trifluorosulfonyloxy, etc.

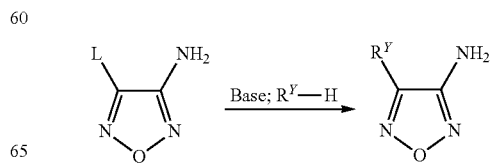

Inventive compounds in which Q is Q4 can be prepared, for example, by the method shown in scheme 6, by base-catalyzed reaction of a benzoyl chloride (II) with a 2-amino-1,3,4-oxadiazole (VII):

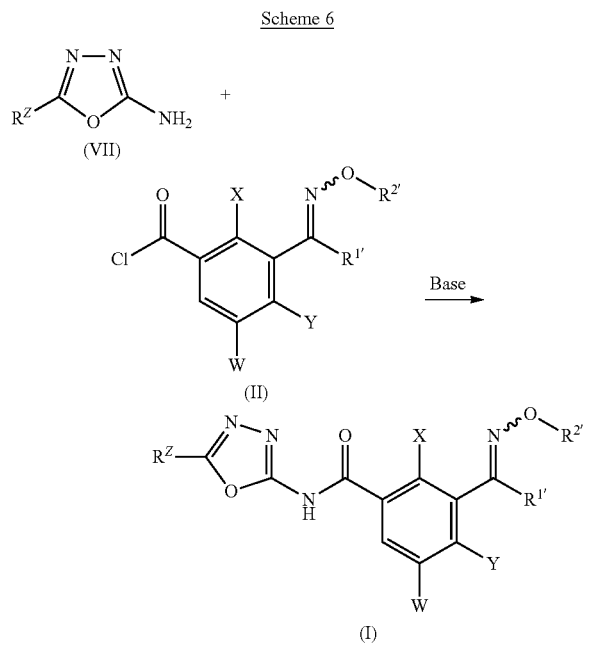

Compounds according to the invention can also be prepared by the method described in scheme 7, by reacting a benzoic acid of the formula (IV) with a 2-amino-1,3,4-oxadiazole (VII):

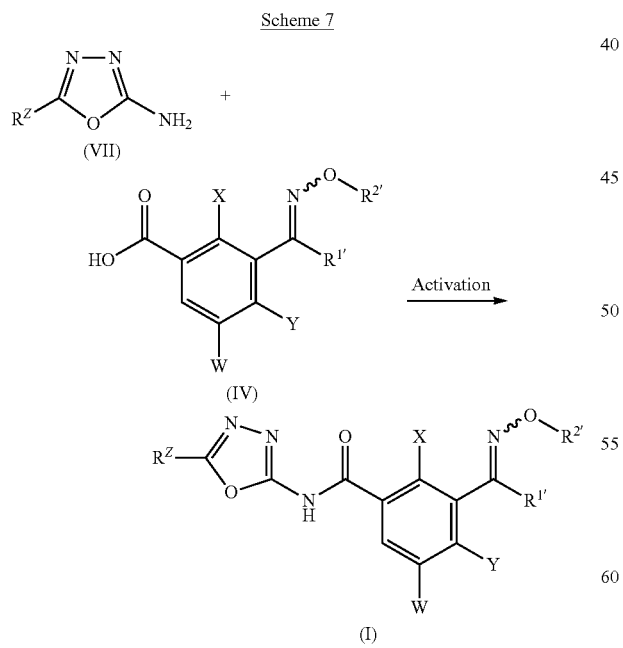

For the activation, it is possible to use dehydrating reagents which are typically for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

Inventive compounds can also be prepared by the method described in scheme 8, by cyclizing a compound of the formula VIII:

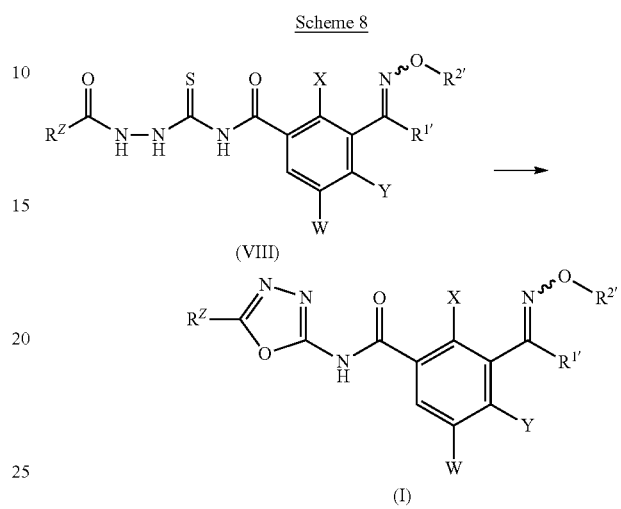

The cyclization can be performed by the methods described in Synth. Commun. 31 (12), 1907-1912 (2001) or in Indian J. Chem., Section B: Organic Chemistry Including Medicinal Chemistry; Vol. 43 (10), 2170-2174 (2004).

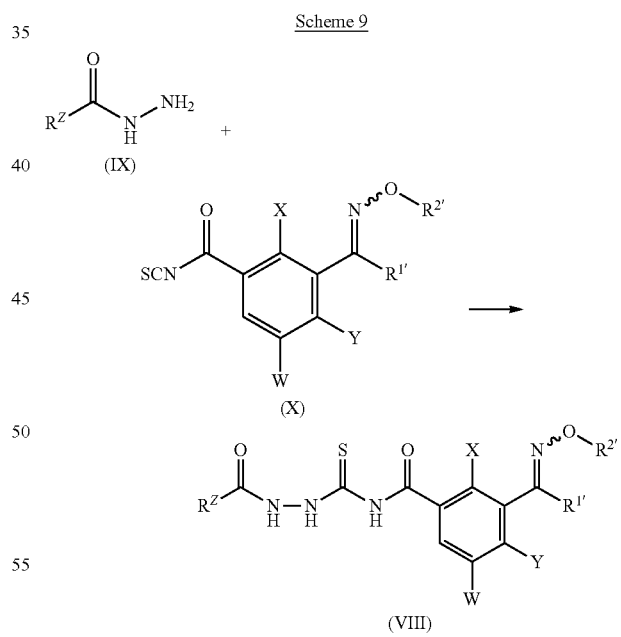

The compound of the formula VIII used in scheme 8 can be prepared by reaction of an acyl isothiocyanate of the formula X with a hydrazide of the formula IX by the method described in Synth. Commun. 25(12), 1885-1892 (1995).

Inventive compounds in which the substituent R is not hydrogen can be prepared, for example, according to the method shown in scheme 10, by reacting an N-(1,2,5-oxadiazol-3-yl)-, N-(1,3,4-oxadiazol-2-yl)-, N-(tetrazol-5- yl)- or N-(triazol-5-yl)arylcarboxamide (I) with a compound of the general formula (III) where L is a leaving group, for example a chlorine, bromine, iodine, mesyloxy, tosyloxy, trifluorosulfonyloxy, etc.:

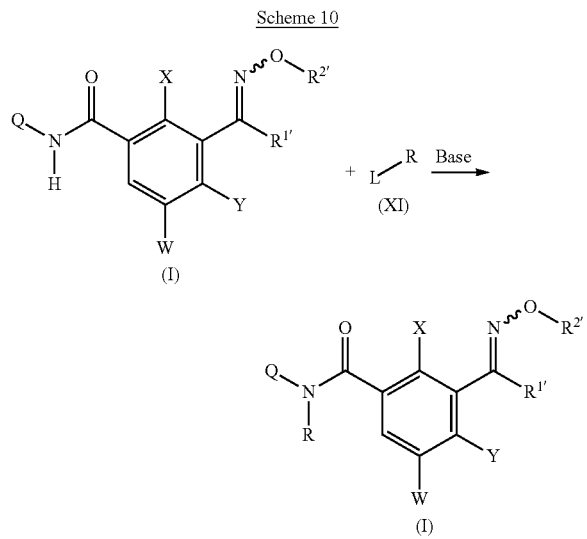

The compounds of the formula (XI) in which L is a leaving group, for example chlorine, bromine, iodine, methylsulfonyloxy, tosyloxy or trifluorosulfonyloxy are either commercially available or can be prepared by known methods described in the literature.

Inventive compounds can also be prepared according to the method shown in scheme 11 by reaction of an amine of the formula (XII) with an acid chloride (II), as described, for example, in J. Het. Chem. (1972), 9 (1), 107-109:

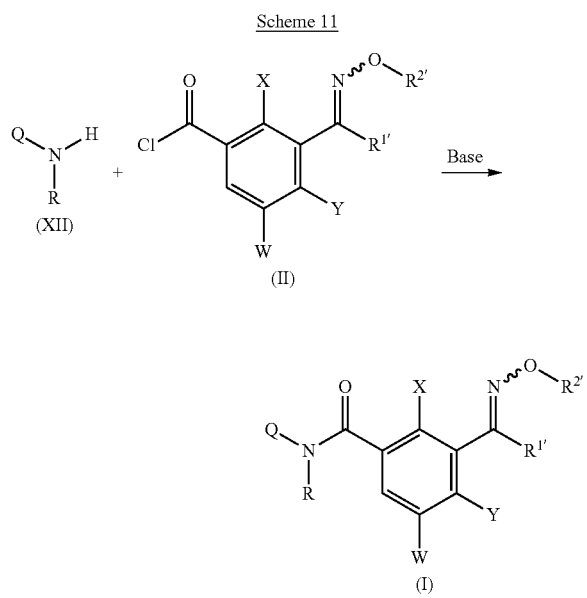

Inventive compounds can also be prepared according to the method shown in scheme 12, by reaction of an amine of the formula (XII) with an acid of the formula (IV):

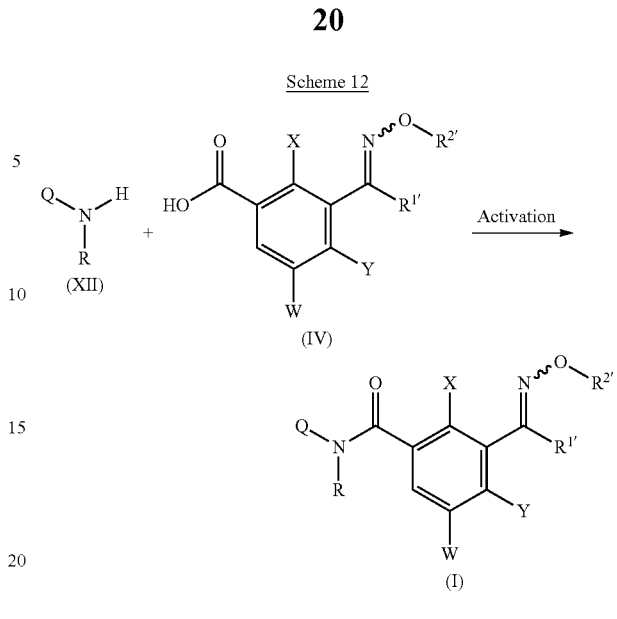

For the activation, it is possible to use dehydrating reagents which are typically for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

The amines of the formula (XII) are either commercially available or known in the literature or can be prepared, for example, by the methods described in scheme 13, by base-catalyzed alkylation or by reductive alkylation, or according to the method described in scheme 14, by nucleophilic substitution of a leaving group L by amines R—$NH_2$.

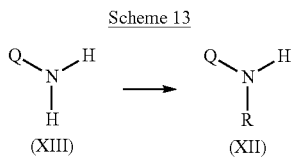

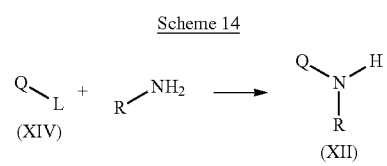

The amines of the formula (XII) can also be prepared by cyclization reactions as described, for example, in J. Org. Chem. 73(10), 3738-3744 (2008) where Q=Q1, or in Buletinul Institutului Politehnic din Iasi (1974), 20(1-2), 95-99 or in J. Org. Chem. 67(21), 7361-7364 (2002) where Q=Q4.

It may be appropriate to alter the sequence of the reaction steps. For instance, benzoic acids bearing a sulfoxide cannot be converted directly to their acid chlorides. One option here is first to prepare the amide at the thioether stage, and then to oxidize the thioether to the sulfoxide.

The workup of the respective reaction mixtures is generally effected by known processes, for example by crystallization, aqueous-extractive workup, by chromatographic methods or by a combination of these methods.

Collections of compounds of the formula (I) which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Gunther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from Perkin Elmer, Waltham, Mass. 02451, USA. For the parallelized purification of compounds of the general formula (I) or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the general formula (I) can take place completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Gunther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the implementation of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described herein gives compounds of the formula (I) in the form of substance collections, which are called libraries. The present invention also provides libraries comprising at least two compounds of the formula (I).

The compounds according to the invention of the formula (I), referred to hereinbelow as "compounds according to the invention", have an excellent herbicidal effectiveness against a broad spectrum of economically important mono- and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferable, with respect to transgenic crops, to use the compounds of the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other types of vegetable. Preferably, the compounds of the invention can be used as herbicides in crops of useful plants which are resistant, or have been made resistant by genetic engineering, to the phytotoxic effects of the herbicides.

It is preferred to use the compounds of the invention in economically important transgenic crops of useful plants and ornamentals, for example of cereals such as wheat, barley, rye, oats, millet/sorghum, rice, cassava and corn or else crops of sugar beet, cotton, soybean, oilseed rape, potato, tomato, peas and other types of vegetable. Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or the sulfonylurea type (EP-A-0257993, U.S. Pat. No. 5,013,659), transgenic crop plants, for example cotton, capable of producing *Bacillus thuringiensis* toxins (Bt toxins), which make the plants resistant to particular pests (EP-A-0142924, EP-A-0193259).

transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature, for example, the abovementioned novel properties ("gene stacking") through combinations.

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition Cold Spring Harbor Laboratory Press, Cold Spring Harbor, N.Y., or Winnacker "Gene und Klone [Genes and clones]", VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227, Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active ingredients of the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986, Wade van Valkenburg, "Pesticide Formulations", Marcel Dekker, N.Y., 1973, K. Martens, "Spray Drying" Handbook, 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", volume 7, C. Hanser Verlag Munich, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active ingredient concentration is, for example, about 10 to 90% by weight, the remainder to 100% by weight consisting of customary formulation constituents. In emulsifiable concentrates, the active ingredient concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active ingredient is in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

A. Chemical Examples

1. Synthesis of 3-[(1E or Z)—N-(cyclopropylmethoxy)ethanimidoyl]-2-methyl-4-(methylsulfonyl)-N-(1-methyl-1H-1,2,4-triazol-5-yl)benzamide (Example No. 4-74))

To an initial charge of 200 mg (0.62 mmol) of 3-[(1E or Z)—N-(cyclopropylmethoxy)ethanimidoyl]-2-methyl-4-(methylsulfonyl)benzoic acid together with 83 mg (0.8 mmol) of 1-methyl-1H-1,2,4-triazol-5-amine in 10 ml of pyridine at room temperature is added 0.07 ml (0.8 mmol) of oxalyl chloride. The reaction solution was stirred at room temperature for 12 h, then concentrated to dryness. The residue was taken up in acetonitrile and separated by column chromatography (HPLC, C18, gradient: acetonitrile/water+ 0.05% trifluoroacetic acid, 20:80→100:0 in 30 min). This gave 92 mg of 3-[(1E or Z)—N-(cyclopropylmethoxy)ethanimidoyl]-2-methyl-4-(methylsulfonyl)-N-(1-methyl-1H-1,2,4-triazol-5-yl)benzamide.

2. Synthesis of 2,4-dichloro-N-(4-chloro-1,2,5-oxadiazol-3-yl)-3-[(1E or Z)—N-methoxyethanimidoyl]benzamide (Example No. 5-1)

To an initial charge of 200 mg (0.76 mmol) of 2,4-dichloro-3-[(1E or Z)—N-methoxyethanimidoyl]benzoic acid together with 115.2 mg (0.92 mmol) of 4-chloro-1,2,5-oxadiazol-3-amine in 3 ml of pyridine at room temperature is added 0.1 ml (1.14 mmol) of oxalyl chloride. The reaction solution was stirred at room temperature for 12 h, then 10 ml of water were added and the mixture was stirred for 10 min. Thereafter, the mixture was extracted with dichloromethane. The organic phase was removed by means of a phase separator and concentrated to dryness. The residue was separated by column chromatography (HPLC, C18, gradient: acetonitrile/water+0.05% trifluoroacetic acid, 20:80→100:0 in 30 min). This gave 172 mg of 2,4-dichloro-N-(4-chloro-1,2,5-oxadiazol-3-yl)-3-[(1E or Z)—N-methoxyethanimidoyl]benzamide.

The examples listed in the tables below were prepared analogously to the abovementioned methods or are obtainable analogously to the abovementioned methods. The compounds listed in the tables below are very particularly preferred. $^1$H NMR data of the compounds indicated by an (*) in tables 1-14 are listed after table 14.

TABLE 1

Inventive compounds of the general formula (I) in which Q is Q1, $R^x$ is a methyl group, and R and W are each hydrogen (E isomer, or Z isomer)

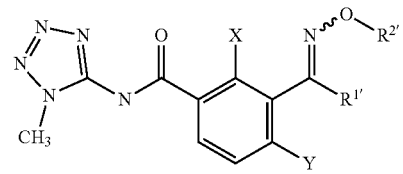

| No. | X | Y | $R^{1'}$ | $R^{2'}$ | Physical data ($^1$H NMR) |
|---|---|---|---|---|---|
| 1-1 | Cl | Cl | Me | Me | |
| 1-2 | Cl | Cl | Et | Me | |
| 1-3 | Cl | Cl | CF$_3$ | Me | |
| 1-4 | Cl | Cl | OMe | Me | |
| 1-5 | Cl | Cl | Me | Et | * |
| 1-6 | Cl | Cl | Me | Pr | |
| 1-7 | Cl | Cl | Me | c-Pr | |
| 1-8 | Cl | Cl | Me | CH$_2$—c-Pr | * |
| 1-9 | Cl | Cl | Me | CH$_2$—CF$_3$ | * |
| 1-10 | Cl | SMe | Me | Me | |
| 1-11 | Cl | SMe | Me | Et | |
| 1-12 | Cl | SMe | Me | CH$_2$—c-Pr | |
| 1-13 | Cl | SMe | Me | CH$_2$—CF$_3$ | |
| 1-14 | Cl | S(O)Me | Me | Me | |
| 1-15 | Cl | SO$_2$Me | Me | Me | * |
| 1-16 | Cl | SO$_2$Me | Et | Me | |
| 1-17 | Cl | SO$_2$Me | CF$_3$ | Me | |

TABLE 1-continued

Inventive compounds of the general formula (I) in which Q is Q1, R$^x$ is a methyl group, and R and W are each hydrogen (E isomer, or Z isomer)

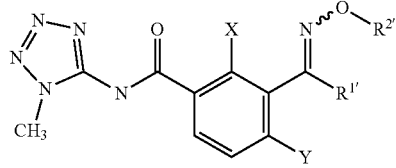

| No. | X | Y | R$^{1'}$ | R$^{2'}$ | Physical data ($^1$H NMR) |
|---|---|---|---|---|---|
| 1-18 | Cl | SO$_2$Me | OMe | Me | |
| 1-19 | Cl | SO$_2$Me | Me | Et | |
| 1-20 | Cl | SO$_2$Me | Me | Pr | |
| 1-21 | Cl | SO$_2$Me | Me | c-Pr | |
| 1-22 | Cl | SO$_2$Me | Me | CH$_2$—c-Pr | * |
| 1-23 | Cl | SO$_2$Me | Me | CH$_2$—CF$_3$ | |
| 1-24 | Cl | Me | Me | Me | |
| 1-25 | Cl | Me | Me | Et | |
| 1-26 | Cl | Me | Me | CH$_2$—c-Pr | |
| 1-27 | Cl | Me | Me | CH$_2$—CF$_3$ | |
| 1-28 | Cl | Et | Me | Me | |
| 1-29 | Cl | c-Pr | Me | Me | |
| 1-30 | Cl | CF$_3$ | Me | Me | |
| 1-31 | Cl | CF$_3$ | Et | Me | |
| 1-32 | Cl | CF$_3$ | CF$_3$ | Me | |
| 1-33 | Cl | CF$_3$ | OMe | Me | |
| 1-34 | Cl | CF$_3$ | Me | Et | |
| 1-35 | Cl | CF$_3$ | Me | Pr | |
| 1-36 | Cl | CF$_3$ | Me | c-Pr | |
| 1-37 | Cl | CF$_3$ | Me | CH$_2$—c-Pr | |
| 1-38 | Cl | CF$_3$ | Me | CH$_2$—CF$_3$ | |
| 1-39 | Cl | OMe | Me | Me | |
| 1-40 | Cl | OMe | Me | Et | |
| 1-41 | Cl | OMe | Me | CH$_2$—c-Pr | |
| 1-42 | Cl | OMe | Me | CH$_2$—CF$_3$ | |
| 1-43 | Cl | SO$_2$Et | Me | Me | |
| 1-44 | Cl | SO$_2$Et | Me | Et | |
| 1-45 | Cl | SO$_2$Et | Me | CH$_2$—c-Pr | |
| 1-46 | Cl | SO$_2$Et | Me | CH$_2$—CF$_3$ | |
| 1-47 | Cl | C$_2$F$_5$ | Me | Me | |
| 1-48 | Cl | Vinyl | Me | Me | |
| 1-49 | Cl | 1-Me-vinyl | Me | Me | |
| 1-50 | Br | SO$_2$Me | Me | Me | |
| 1-51 | Br | SO$_2$Me | Et | Me | |
| 1-52 | Br | SO$_2$Me | CF$_3$ | Me | |
| 1-53 | Br | SO$_2$Me | OMe | Me | |
| 1-54 | Br | SO$_2$Me | Me | Et | |
| 1-55 | Br | SO$_2$Me | Me | Pr | |
| 1-56 | Br | SO$_2$Me | Me | c-Pr | |
| 1-57 | Br | SO$_2$Me | Me | CH$_2$—c-Pr | |
| 1-58 | Br | SO$_2$Me | Me | CH$_2$—CF$_3$ | |
| 1-59 | Br | Me | Me | Me | |
| 1-60 | Br | Et | Me | Me | |
| 1-61 | Br | CF$_3$ | Me | Me | |
| 1-62 | Br | CF$_3$ | Me | Et | |
| 1-63 | Br | CF$_3$ | Me | CH$_2$—c-Pr | |
| 1-64 | Br | CF$_3$ | Me | CH$_2$—CF$_3$ | |
| 1-65 | Me | SMe | Me | Me | |
| 1-66 | Me | S(O)Me | Me | Me | |
| 1-67 | Me | SO$_2$Me | Me | Me | * |
| 1-68 | Me | SO$_2$Me | Et | Me | |
| 1-69 | Me | SO$_2$Me | CF$_3$ | Me | |
| 1-70 | Me | SO$_2$Me | OMe | Me | |
| 1-71 | Me | SO$_2$Me | Me | Et | * |
| 1-72 | Me | SO$_2$Me | Me | Pr | |
| 1-73 | Me | SO$_2$Me | Me | c-Pr | |
| 1-74 | Me | SO$_2$Me | Me | CH$_2$—c-Pr | * |
| 1-75 | Me | SO$_2$Me | Me | CH$_2$—CF$_3$ | |
| 1-76 | Me | Me | Me | Me | |
| 1-77 | Me | Me | Et | Me | |
| 1-78 | Me | Me | CF$_3$ | Me | |
| 1-79 | Me | Me | OMe | Me | |
| 1-80 | Me | Me | Me | Et | |
| 1-81 | Me | Me | Me | Pr | |
| 1-82 | Me | Me | Me | c-Pr | |
| 1-83 | Me | Me | Me | CH$_2$—c-Pr | |
| 1-84 | Me | Me | Me | CH$_2$—CF$_3$ | |
| 1-85 | Me | Et | Me | Me | |
| 1-86 | Me | CF$_3$ | Me | Me | |
| 1-87 | Me | CF$_3$ | Et | Me | |
| 1-88 | Me | CF$_3$ | CF$_3$ | Me | |
| 1-89 | Me | CF$_3$ | OMe | Me | |
| 1-90 | Me | CF$_3$ | Me | Et | |
| 1-91 | Me | CF$_3$ | Me | Pr | |
| 1-92 | Me | CF$_3$ | Me | c-Pr | |
| 1-93 | Me | CF$_3$ | Me | CH$_2$—c-Pr | |
| 1-94 | Me | CF$_3$ | Me | CH$_2$—CF$_3$ | |
| 1-95 | Me | SO$_2$Et | Me | Me | |
| 1-96 | Me | SO$_2$Et | Me | Et | |
| 1-97 | Me | SO$_2$Et | Me | CH$_2$—c-Pr | |
| 1-98 | Me | SO$_2$Et | Me | CH$_2$—CF$_3$ | |
| 1-99 | Me | C$_2$F$_5$ | Me | Me | |
| 1-100 | Me | c-Pr | Me | Me | |
| 1-101 | OMe | Cl | Me | Me | |
| 1-102 | OMe | CF$_3$ | Me | Me | |
| 1-103 | OMe | CF$_3$ | Me | Et | |
| 1-104 | OMe | CF$_3$ | Me | CH$_2$—c-Pr | |
| 1-105 | OMe | CF$_3$ | Me | CH$_2$—CF$_3$ | |
| 1-106 | OMe | CHF$_2$ | Me | Me | |
| 1-107 | OMe | CHF$_2$ | Et | Me | |
| 1-108 | OMe | CHF$_2$ | CF$_3$ | Me | |
| 1-109 | OMe | CHF$_2$ | OMe | Me | |
| 1-110 | OMe | CHF$_2$ | Me | Et | |
| 1-111 | OMe | CHF$_2$ | Me | Pr | |
| 1-112 | OMe | CHF$_2$ | Me | c-Pr | |
| 1-113 | OMe | CHF$_2$ | Me | CH$_2$—c-Pr | |
| 1-114 | OMe | CHF$_2$ | Me | CH$_2$—CF$_3$ | |
| 1-115 | OMe | CF$_2$Cl | Me | Me | |
| 1-116 | OMe | SO$_2$Me | Me | Me | |
| 1-117 | SO$_2$Me | CF$_3$ | Me | Me | |
| 1-118 | SO$_2$Me | CF$_3$ | Et | Me | |
| 1-119 | SO$_2$Me | CF$_3$ | CF$_3$ | Me | |
| 1-120 | SO$_2$Me | CF$_3$ | OMe | Me | |
| 1-121 | SO$_2$Me | CF$_3$ | Me | Et | |
| 1-122 | SO$_2$Me | CF$_3$ | Me | Pr | |
| 1-123 | SO$_2$Me | CF$_3$ | Me | c-Pr | |
| 1-124 | SO$_2$Me | CF$_3$ | Me | CH$_2$—c-Pr | |
| 1-125 | CH$_2$OMe | CF$_3$ | Me | CH$_2$—CF$_3$ | |
| 1-126 | SMe | CF$_3$ | Me | Me | |
| 1-127 | SMe | CF$_3$ | Me | Et | |
| 1-128 | SMe | CF$_3$ | Me | CH$_2$—c-Pr | |
| 1-129 | SMe | CF$_3$ | Me | CH$_2$—CF$_3$ | |
| 1-130 | SMe | SO$_2$Me | Me | Me | |
| 1-131 | CF$_3$ | CF$_3$ | Me | Me | |
| 1-132 | CF$_3$ | CF$_3$ | Me | Et | |
| 1-133 | CF$_3$ | CF$_3$ | Me | CH$_2$—c-Pr | |
| 1-134 | CF$_3$ | CF$_3$ | Me | CH$_2$—CF$_3$ | |
| 1-135 | F | CF$_3$ | Me | Me | |
| 1-136 | Me | SO$_2$Me | Me | i-Bu | |
| 1-137 | | | | | |

TABLE 2

Inventive compounds of the general formula (I) in which Q is Q1, $R^x$ is an ethyl group, and R and W are each hydrogen (E isomer, or Z isomer)

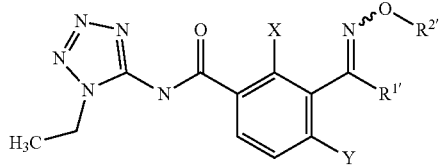

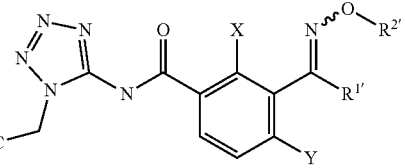

| No. | X | Y | $R^{1'}$ | $R^{2'}$ | Physical data ($^1$H NMR) | No. | X | Y | $R^{1'}$ | $R^{2'}$ | Physical data ($^1$H NMR) |
|---|---|---|---|---|---|---|---|---|---|---|---|
| 2-1 | Cl | Cl | Me | Me | * | 2-65 | Me | S(O)Me | Me | Me | |
| 2-2 | Cl | Cl | Et | Me | | 2-66 | Me | SO₂Me | Me | Me | * |
| 2-3 | Cl | Cl | CF₃ | Me | | 2-67 | Me | SO₂Me | Et | Me | |
| 2-4 | Cl | Cl | OMe | Me | | 2-68 | Me | SO₂Me | CF₃ | Me | |
| 2-5 | Cl | Cl | Me | Et | | 2-69 | Me | SO₂Me | OMe | Me | |
| 2-6 | Cl | Cl | Me | Pr | | 2-70 | Me | SO₂Me | Me | Et | * |
| 2-7 | Cl | Cl | Me | c-Pr | | 2-71 | Me | SO₂Me | Me | Pr | |
| 2-8 | Cl | Cl | Me | CH₂—c-Pr | | 2-72 | Me | SO₂Me | Me | c-Pr | |
| 2-9 | Cl | Cl | Me | CH₂—CF₃ | | 2-73 | Me | SO₂Me | Me | CH₂—c-Pr | * |
| 2-10 | Cl | SMe | Me | Me | | 2-74 | Me | SO₂Me | Me | CH₂—CF₃ | |
| 2-11 | Cl | SMe | Me | Et | | 2-75 | Me | Me | Me | Me | |
| 2-12 | Cl | SMe | Me | CH₂—c-Pr | | 2-76 | Me | Me | Et | Me | |
| 2-13 | Cl | SMe | Me | CH₂—CF₃ | | 2-77 | Me | Me | CF₃ | Me | |
| 2-14 | Cl | S(O)Me | Me | Me | | 2-78 | Me | Me | OMe | Me | |
| 2-15 | Cl | SO₂Me | Me | Me | * | 2-79 | Me | Me | Me | Et | |
| 2-16 | Cl | SO₂Me | Et | Me | | 2-80 | Me | Me | Me | Pr | |
| 2-17 | Cl | SO₂Me | CF₃ | Me | | 2-81 | Me | Me | Me | c-Pr | |
| 2-18 | Cl | SO₂Me | OMe | Me | | 2-82 | Me | Me | Me | CH₂—c-Pr | |
| 2-19 | Cl | SO₂Me | Me | Et | * | 2-83 | Me | Me | Me | CH₂—CF₃ | |
| 2-20 | Cl | SO₂Me | Me | Pr | | 2-84 | Me | Et | Me | Me | |
| 2-21 | Cl | SO₂Me | Me | c-Pr | | 2-85 | Me | CF₃ | Me | Me | |
| 2-22 | Cl | SO₂Me | Me | CH₂—c-Pr | * | 2-86 | Me | CF₃ | Et | Me | |
| 2-23 | Cl | SO₂Me | Me | CH₂—CF₃ | | 2-87 | Me | CF₃ | CF₃ | Me | |
| 2-24 | Cl | Me | Me | Me | | 2-88 | Me | CF₃ | OMe | Me | |
| 2-25 | Cl | Me | Me | Et | | 2-89 | Me | CF₃ | Me | Et | |
| 2-26 | Cl | Me | Me | CH₂—c-Pr | | 2-90 | Me | CF₃ | Me | Pr | |
| 2-27 | Cl | Me | Me | CH₂—CF₃ | | 2-91 | Me | CF₃ | Me | c-Pr | |
| 2-28 | Cl | Et | Me | Me | | 2-92 | Me | CF₃ | Me | CH₂—c-Pr | |
| | Cl | c-Pr | Me | Me | | 2-93 | Me | CF₃ | Me | CH₂—CF₃ | |
| 2-29 | Cl | CF₃ | Me | Me | | 2-94 | Me | SO₂Et | Me | Me | |
| 2-30 | Cl | CF₃ | Me | Et | | 2-95 | Me | SO₂Et | Me | Et | |
| 2-31 | Cl | CF₃ | CF₃ | Me | | 2-96 | Me | SO₂Et | Me | CH₂—c-Pr | |
| 2-32 | Cl | CF₃ | OMe | Me | | 2-97 | Me | SO₂Et | Me | CH₂—CF₃ | |
| 2-33 | Cl | CF₃ | Me | Et | | 2-98 | Me | C₂F₅ | Me | Me | |
| 2-34 | Cl | CF₃ | Me | Pr | | 2-99 | Me | c-Pr | Me | Me | |
| 2-35 | Cl | CF₃ | Me | c-Pr | | 2-100 | OMe | Cl | Me | Me | |
| 2-36 | Cl | CF₃ | Me | CH₂—c-Pr | | 2-101 | OMe | CF₃ | Me | Me | |
| 2-37 | Cl | CF₃ | Me | CH₂—CF₃ | | 2-102 | OMe | CF₃ | Me | Et | |
| 2-38 | Cl | OMe | Me | Me | | 2-103 | OMe | CF₃ | Me | CH₂—c-Pr | |
| 2-39 | Cl | OMe | Me | Et | | 2-104 | OMe | CF₃ | Me | CH₂—CF₃ | |
| 2-40 | Cl | OMe | Me | CH₂—c-Pr | | 2-105 | OMe | CHF₂ | Me | Me | |
| 2-41 | Cl | OMe | Me | CH₂—CF₃ | | 2-106 | OMe | CHF₂ | Et | Me | |
| 2-42 | Cl | SO₂Et | Me | Me | | 2-107 | OMe | CHF₂ | CF₃ | Me | |
| 2-43 | Cl | SO₂Et | Me | Et | | 2-108 | OMe | CHF₂ | OMe | Me | |
| 2-44 | Cl | SO₂Et | Me | CH₂—c-Pr | | 2-109 | OMe | CHF₂ | Me | Et | |
| 2-45 | Cl | SO₂Et | Me | CH₂—CF₃ | | 2-110 | OMe | CHF₂ | Me | Pr | |
| 2-46 | Cl | C₂F₅ | Me | Me | | 2-111 | OMe | CHF₂ | Me | c-Pr | |
| 2-47 | Cl | Vinyl | Me | Me | | 2-112 | OMe | CHF₂ | Me | CH₂—c-Pr | |
| 2-48 | Cl | 1-Me-vinyl | Me | Me | | 2-113 | OMe | CHF₂ | Me | CH₂—CF₃ | |
| 2-49 | Br | SO₂Me | Me | Me | | 2-114 | OMe | CF₂Cl | Me | Me | |
| 2-50 | Br | SO₂Me | Et | Me | | 2-115 | OMe | SO₂Me | Me | Me | |
| 2-51 | Br | SO₂Me | CF₃ | Me | | 2-116 | SO₂Me | CF₃ | Me | Me | |
| 2-52 | Br | SO₂Me | OMe | Me | | 2-117 | SO₂Me | CF₃ | Et | Me | |
| 2-53 | Br | SO₂Me | Me | Et | | 2-118 | SO₂Me | CF₃ | CF₃ | Me | |
| 2-54 | Br | SO₂Me | Me | Pr | | 2-119 | SO₂Me | CF₃ | OMe | Me | |
| 2-55 | Br | SO₂Me | Me | c-Pr | | 2-120 | SO₂Me | CF₃ | Me | Et | |
| 2-56 | Br | SO₂Me | Me | CH₂—c-Pr | | 2-121 | SO₂Me | CF₃ | Me | Pr | |
| 2-57 | Br | SO₂Me | Me | CH₂—CF₃ | | 2-122 | SO₂Me | CF₃ | Me | c-Pr | |
| 2-58 | Br | Me | Me | Me | | 2-123 | SO₂Me | CF₃ | Me | CH₂—c-Pr | |
| 2-59 | Br | Et | Me | Me | | 2-124 | CH₂OMe | CF₃ | Me | CH₂—CF₃ | |
| 2-60 | Br | CF₃ | Me | Me | | 2-125 | SMe | CF₃ | Me | Me | |
| 2-61 | Br | CF₃ | Me | Et | | 2-126 | SMe | CF₃ | Me | Et | |
| 2-62 | Br | CF₃ | Me | CH₂—c-Pr | | 2-127 | SMe | CF₃ | Me | CH₂—c-Pr | |
| 2-63 | Br | CF₃ | Me | CH₂—CF₃ | | 2-128 | SMe | CF₃ | Me | CH₂—CF₃ | |
| 2-64 | Me | SMe | Me | Me | | 2-129 | SMe | SO₂Me | Me | Me | |

TABLE 2-continued

Inventive compounds of the general formula (I) in which Q is Q1, R$^x$ is an ethyl group, and R and W are each hydrogen (E isomer, or Z isomer)

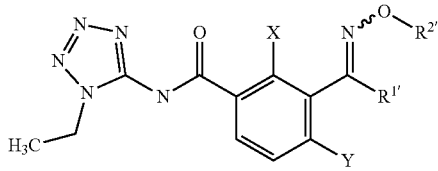

| No. | X | Y | R$^{1'}$ | R$^{2'}$ | Physical data ($^1$H NMR) |
|---|---|---|---|---|---|
| 2-130 | CF$_3$ | CF$_3$ | Me | Me | |
| 2-131 | CF$_3$ | CF$_3$ | Me | Et | |
| 2-132 | CF$_3$ | CF$_3$ | Me | CH$_2$—c-Pr | |
| 2-133 | CF$_3$ | CF$_3$ | Me | CH$_2$—CF$_3$ | |
| 2-134 | F | CF$_3$ | Me | Me | |
| 2-135 | Me | SO$_2$Me | Me | i-Bu | * |
| 2-136 | | | | | |

TABLE 3

Inventive compounds of the general formula (I) in which Q is Q1, R$^x$ is a propyl group, and R and W are each hydrogen (E isomer, or Z isomer)

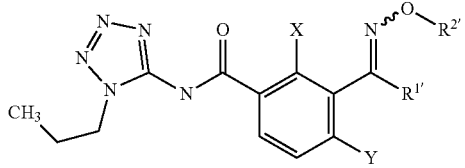

| No. | X | Y | R$^{1'}$ | R$^{2'}$ | Physical data ($^1$H NMR) |
|---|---|---|---|---|---|
| 3-1 | Cl | Cl | Me | Me | * |
| 3-2 | Cl | Cl | Et | Me | |
| 3-3 | Cl | Cl | CF$_3$ | Me | |
| 3-4 | Cl | Cl | OMe | Me | |
| 3-5 | Cl | Cl | Me | Et | * |
| 3-6 | Cl | Cl | Me | Pr | |
| 3-7 | Cl | Cl | Me | c-Pr | |
| 3-8 | Cl | Cl | Me | CH$_2$—c-Pr | * |
| 3-9 | Cl | Cl | Me | CH$_2$—CF$_3$ | * |
| 3-10 | Cl | SMe | Me | Me | |
| 3-11 | Cl | SMe | Me | Et | |
| 3-12 | Cl | SMe | Me | CH$_2$—c-Pr | |
| 3-13 | Cl | SMe | Me | CH$_2$—CF$_3$ | |
| 3-14 | Cl | S(O)Me | Me | Me | |
| 3-15 | Cl | SO$_2$Me | Me | Me | * |
| 3-16 | Cl | SO$_2$Me | Et | Me | |
| 3-17 | Cl | SO$_2$Me | CF$_3$ | Me | |
| 3-18 | Cl | SO$_2$Me | OMe | Me | |
| 3-19 | Cl | SO$_2$Me | Me | Et | * |
| 3-20 | Cl | SO$_2$Me | Me | Pr | |
| 3-21 | Cl | SO$_2$Me | Me | c-Pr | |
| 3-22 | Cl | SO$_2$Me | Me | CH$_2$—c-Pr | * |
| 3-23 | Cl | SO$_2$Me | Me | CH$_2$—CF$_3$ | |
| 3-24 | Cl | Me | Me | Me | |
| 3-25 | Cl | Me | Me | Et | |
| 3-26 | Cl | Me | Me | CH$_2$—c-Pr | |
| 3-27 | Cl | Me | Me | CH$_2$—CF$_3$ | |
| 3-28 | Cl | Et | Me | Me | |
| 3-29 | Cl | c-Pr | Me | Me | |
| 3-30 | Cl | CF$_3$ | Me | Me | |
| 3-31 | Cl | CF$_3$ | Et | Me | |
| 3-32 | Cl | CF$_3$ | CF$_3$ | Me | |
| 3-33 | Cl | CF$_3$ | OMe | Me | |
| 3-34 | Cl | CF$_3$ | Me | Et | |
| 3-35 | Cl | CF$_3$ | Me | Pr | |
| 3-36 | Cl | CF$_3$ | Me | c-Pr | |
| 3-37 | Cl | CF$_3$ | Me | CH$_2$—c-Pr | |

TABLE 3-continued

Inventive compounds of the general formula (I) in which Q is Q1, R$^x$ is a propyl group, and R and W are each hydrogen (E isomer, or Z isomer)

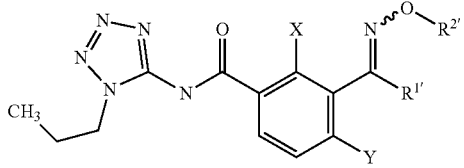

| No. | X | Y | R$^{1'}$ | R$^{2'}$ | Physical data ($^1$H NMR) |
|---|---|---|---|---|---|
| 3-38 | Cl | CF$_3$ | Me | CH$_2$—CF$_3$ | |
| 3-39 | Cl | OMe | Me | Me | |
| 3-40 | Cl | OMe | Me | Et | |
| 3-41 | Cl | OMe | Me | CH$_2$—c-Pr | |
| 3-42 | Cl | OMe | Me | CH$_2$—CF$_3$ | |
| 3-43 | Cl | SO$_2$Et | Me | Me | |
| 3-44 | Cl | SO$_2$Et | Me | Et | |
| 3-45 | Cl | SO$_2$Et | Me | CH$_2$—c-Pr | |
| 3-46 | Cl | SO$_2$Et | Me | CH$_2$—CF$_3$ | |
| 3-47 | Cl | C$_2$F$_5$ | Me | Me | |
| 3-48 | Cl | Vinyl | Me | Me | |
| 3-49 | Cl | 1-Me-vinyl | Me | Me | |
| 3-50 | Br | SO$_2$Me | Me | Me | |
| 3-51 | Br | SO$_2$Me | Et | Me | |
| 3-52 | Br | SO$_2$Me | CF$_3$ | Me | |
| 3-53 | Br | SO$_2$Me | OMe | Me | |
| 3-54 | Br | SO$_2$Me | Me | Et | |
| 3-55 | Br | SO$_2$Me | Me | Pr | |
| 3-56 | Br | SO$_2$Me | Me | c-Pr | |
| 3-57 | Br | SO$_2$Me | Me | CH$_2$—c-Pr | |
| 3-58 | Br | SO$_2$Me | Me | CH$_2$—CF$_3$ | |
| 3-59 | Br | Me | Me | Me | |
| 3-60 | Br | Et | Me | Me | |
| 3-61 | Br | CF$_3$ | Me | Me | |
| 3-62 | Br | CF$_3$ | Me | Et | |
| 3-63 | Br | CF$_3$ | Me | CH$_2$—c-Pr | |
| 3-64 | Br | CF$_3$ | Me | CH$_2$—CF$_3$ | |
| 3-65 | Me | SMe | Me | Me | |
| 3-66 | Me | S(O)Me | Me | Me | |
| 3-67 | Me | SO$_2$Me | Me | Me | |
| 3-68 | Me | SO$_2$Me | Et | Me | |
| 3-69 | Me | SO$_2$Me | CF$_3$ | Me | |
| 3-70 | Me | SO$_2$Me | OMe | Me | |
| 3-71 | Me | SO$_2$Me | Me | Et | |
| 3-72 | Me | SO$_2$Me | Me | Pr | |
| 3-73 | Me | SO$_2$Me | Me | c-Pr | |
| 3-74 | Me | SO$_2$Me | Me | CH$_2$—c-Pr | |
| 3-75 | Me | SO$_2$Me | Me | CH$_2$—CF$_3$ | |
| 3-76 | Me | Me | Me | Me | |
| 3-77 | Me | Me | Et | Me | |
| 3-78 | Me | Me | CF$_3$ | Me | |
| 3-79 | Me | Me | OMe | Me | |
| 3-80 | Me | Me | Me | Et | |
| 3-81 | Me | Me | Me | Pr | |
| 3-82 | Me | Me | Me | c-Pr | |
| 3-83 | Me | Me | Me | CH$_2$—c-Pr | |
| 3-84 | Me | Me | Me | CH$_2$—CF$_3$ | |
| 3-85 | Me | Et | Me | Me | |
| 3-86 | Me | CF$_3$ | Me | Me | |
| 3-87 | Me | CF$_3$ | Et | Me | |
| 3-88 | Me | CF$_3$ | CF$_3$ | Me | |
| 3-89 | Me | CF$_3$ | OMe | Me | |
| 3-90 | Me | CF$_3$ | Me | Et | |
| 3-91 | Me | CF$_3$ | Me | Pr | |
| 3-92 | Me | CF$_3$ | Me | c-Pr | |
| 3-93 | Me | CF$_3$ | Me | CH$_2$—c-Pr | |
| 3-94 | Me | CF$_3$ | Me | CH$_2$—CF$_3$ | |
| 3-95 | Me | SO$_2$Et | Me | Me | |
| 3-96 | Me | SO$_2$Et | Me | Et | |
| 3-97 | Me | SO$_2$Et | Me | CH$_2$—c-Pr | |
| 3-98 | Me | SO$_2$Et | Me | CH$_2$—CF$_3$ | |
| 3-99 | Me | C$_2$F$_5$ | Me | Me | |
| 3-100 | Me | c-Pr | Me | Me | |
| 3-101 | OMe | Cl | Me | Me | |
| 3-102 | OMe | CF$_3$ | Me | Me | |

TABLE 3-continued

Inventive compounds of the general formula (I) in which Q is Q1, $R^x$ is a propyl group, and R and W are each hydrogen (E isomer, or Z isomer)

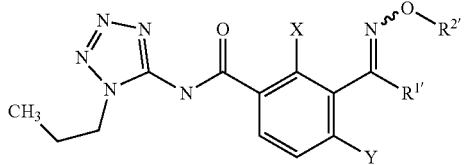

| No. | X | Y | $R^{1'}$ | $R^{2'}$ | Physical data ($^1$H NMR) |
|---|---|---|---|---|---|
| 3-103 | OMe | $CF_3$ | Me | Et | |
| 3-104 | OMe | $CF_3$ | Me | $CH_2$—c-Pr | |
| 3-105 | OMe | $CF_3$ | Me | $CH_2$—$CF_3$ | |
| 3-106 | OMe | $CHF_2$ | Me | Me | |
| 3-107 | OMe | $CHF_2$ | Et | Me | |
| 3-108 | OMe | $CHF_2$ | $CF_3$ | Me | |
| 3-109 | OMe | $CHF_2$ | OMe | Me | |
| 3-110 | OMe | $CHF_2$ | Me | Et | |
| 3-111 | OMe | $CHF_2$ | Me | Pr | |
| 3-112 | OMe | $CHF_2$ | Me | c-Pr | |
| 3-113 | OMe | $CHF_2$ | Me | $CH_2$—c-Pr | |
| 3-114 | OMe | $CHF_2$ | Me | $CH_2$—$CF_3$ | |
| 3-115 | OMe | $CF_2Cl$ | Me | Me | |
| 3-116 | OMe | $SO_2Me$ | Me | Me | |
| 3-117 | $SO_2Me$ | $CF_3$ | Me | Me | |
| 3-118 | $SO_2Me$ | $CF_3$ | Et | Me | |
| 3-119 | $SO_2Me$ | $CF_3$ | $CF_3$ | Me | |
| 3-120 | $SO_2Me$ | $CF_3$ | OMe | Me | |
| 3-121 | $SO_2Me$ | $CF_3$ | Me | Et | |
| 3-122 | $SO_2Me$ | $CF_3$ | Me | Pr | |
| 3-123 | $SO_2Me$ | $CF_3$ | Me | c-Pr | |
| 3-124 | $SO_2Me$ | $CF_3$ | Me | $CH_2$—c-Pr | |
| 3-125 | $CH_2OMe$ | $CF_3$ | Me | $CH_2$—$CF_3$ | |
| 3-126 | SMe | $CF_3$ | Me | Me | |
| 3-127 | SMe | $CF_3$ | Me | Et | |
| 3-128 | SMe | $CF_3$ | Me | $CH_2$—c-Pr | |
| 3-129 | SMe | $CF_3$ | Me | $CH_2$—$CF_3$ | |
| 3-130 | SMe | $SO_2Me$ | Me | Me | |
| 3-131 | $CF_3$ | $CF_3$ | Me | Me | |
| 3-132 | $CF_3$ | $CF_3$ | Me | Et | |
| 3-133 | $CF_3$ | $CF_3$ | Me | $CH_2$—c-Pr | |
| 3-134 | $CF_3$ | $CF_3$ | Me | $CH_2$—$CF_3$ | |
| 3-135 | F | $CF_3$ | Me | Me | |
| 3-136 | Me | $SO_2Me$ | Me | i-Bu | |

TABLE 4

Inventive compounds of the general formula (I) in which Q is Q2, $R^x$ is a methyl group, and R and W are each hydrogen (E isomer, or Z isomer)

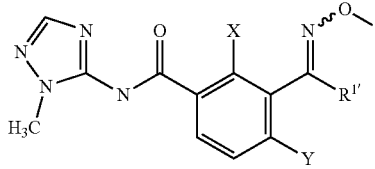

| No. | X | Y | $R^{1'}$ | $R^{2'}$ | Physical data ($^1$H NMR) |
|---|---|---|---|---|---|
| 4-1 | Cl | Cl | Me | Me | * |
| 4-2 | Cl | Cl | Et | Me | |
| 4-3 | Cl | Cl | $CF_3$ | Me | |
| 4-4 | Cl | Cl | OMe | Me | |
| 4-5 | Cl | Cl | Me | Et | * |
| 4-6 | Cl | Cl | Me | Pr | |
| 4-7 | Cl | Cl | Me | c-Pr | |
| 4-8 | Cl | Cl | Me | $CH_2$-c-Pr | * |
| 4-9 | Cl | Cl | Me | $CH_2$—$CF_3$ | * |

TABLE 4-continued

Inventive compounds of the general formula (I) in which Q is Q2, $R^x$ is a methyl group, and R and W are each hydrogen (E isomer, or Z isomer)

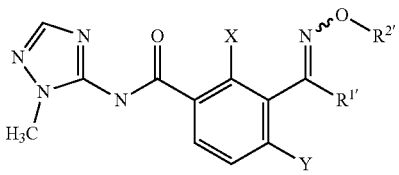

| No. | X | Y | $R^{1'}$ | $R^{2'}$ | Physical data ($^1$H NMR) |
|---|---|---|---|---|---|
| 4-10 | Cl | SMe | Me | Me | |
| 4-11 | Cl | SMe | Me | Et | |
| 4-12 | Cl | SMe | Me | $CH_2$-c-Pr | |
| 4-13 | Cl | SMe | Me | $CH_2$—$CF_3$ | |
| 4-14 | Cl | S(O)Me | Me | Me | |
| 4-15 | Cl | $SO_2Me$ | Me | Me | * |
| 4-16 | Cl | $SO_2Me$ | Et | Me | |
| 4-17 | Cl | $SO_2Me$ | $CF_3$ | Me | |
| 4-18 | Cl | $SO_2Me$ | OMe | Me | |
| 4-19 | Cl | $SO_2Me$ | Me | Et | * |
| 4-20 | Cl | $SO_2Me$ | Me | Pr | |
| 4-21 | Cl | $SO_2Me$ | Me | c-Pr | |
| 4-22 | Cl | $SO_2Me$ | Me | $CH_2$-c-Pr | * |
| 4-23 | Cl | $SO_2Me$ | Me | $CH_2$—$CF_3$ | |
| 4-24 | Cl | Me | Me | Me | |
| 4-25 | Cl | Me | Me | Et | |
| 4-26 | Cl | Me | Me | $CH_2$-c-Pr | |
| 4-27 | Cl | Me | Me | $CH_2$—$CF_3$ | |
| 4-28 | Cl | Et | Me | Me | |
| 4-29 | Cl | c-Pr | Me | Me | |
| 4-30 | Cl | $CF_3$ | Me | Me | |
| 4-31 | Cl | $CF_3$ | Et | Me | |
| 4-32 | Cl | $CF_3$ | $CF_3$ | Me | |
| 4-33 | Cl | $CF_3$ | OMe | Me | |
| 4-34 | Cl | $CF_3$ | Me | Et | |
| 4-35 | Cl | $CF_3$ | Me | Pr | |
| 4-36 | Cl | $CF_3$ | Me | c-Pr | |
| 4-37 | Cl | $CF_3$ | Me | $CH_2$-c-Pr | |
| 4-38 | Cl | $CF_3$ | Me | $CH_2$—$CF_3$ | |
| 4-39 | Cl | OMe | Me | Me | |
| 4-40 | Cl | OMe | Me | Et | |
| 4-41 | Cl | OMe | Me | $CH_2$-c-Pr | |
| 4-42 | Cl | OMe | Me | $CH_2$—$CF_3$ | |
| 4-43 | Cl | $SO_2Et$ | Me | Me | |
| 4-44 | Cl | $SO_2Et$ | Me | Et | |
| 4-45 | Cl | $SO_2Et$ | Me | $CH_2$-c-Pr | |
| 4-46 | Cl | $SO_2Et$ | Me | $CH_2$—$CF_3$ | |
| 4-47 | Cl | $C_2F_5$ | Me | Me | |
| 4-48 | Cl | Vinyl | Me | Me | |
| 4-49 | Cl | 1-Me-vinyl | Me | Me | |
| 4-50 | Br | $SO_2Me$ | Me | Me | |
| 4-51 | Br | $SO_2Me$ | Et | Me | |
| 4-52 | Br | $SO_2Me$ | $CF_3$ | Me | |
| 4-53 | Br | $SO_2Me$ | OMe | Me | |
| 4-54 | Br | $SO_2Me$ | Me | Et | |
| 4-55 | Br | $SO_2Me$ | Me | Pr | |
| 4-56 | Br | $SO_2Me$ | Me | c-Pr | |
| 4-57 | Br | $SO_2Me$ | Me | $CH_2$-c-Pr | |
| 4-58 | Br | $SO_2Me$ | Me | $CH_2$—$CF_3$ | |
| 4-59 | Br | Me | Me | Me | |
| 4-60 | Br | Et | Me | Me | |
| 4-61 | Br | $CF_3$ | Me | Me | |
| 4-62 | Br | $CF_3$ | Me | Et | |
| 4-63 | Br | $CF_3$ | Me | $CH_2$-c-Pr | |
| 4-64 | Br | $CF_3$ | Me | $CH_2$—$CF_3$ | |
| 4-65 | Me | SMe | Me | Me | |
| 4-66 | Me | S(O)Me | Me | Me | |
| 4-67 | Me | $SO_2Me$ | Me | Me | |
| 4-68 | Me | $SO_2Me$ | Et | Me | |
| 4-69 | Me | $SO_2Me$ | $CF_3$ | Me | |
| 4-70 | Me | $SO_2Me$ | OMe | Me | |
| 4-71 | Me | $SO_2Me$ | Me | Et | |
| 4-72 | Me | $SO_2Me$ | Me | Pr | |
| 4-73 | Me | $SO_2Me$ | Me | c-Pr | |

TABLE 4-continued

Inventive compounds of the general formula (I) in which Q is Q2, $R^x$ is a methyl group, and R and W are each hydrogen (E isomer, or Z isomer)

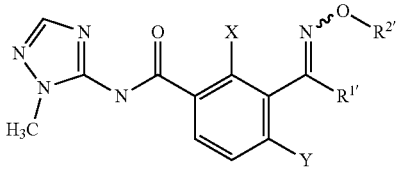

| No. | X | Y | $R^{1'}$ | $R^{2'}$ | Physical data ($^1$H NMR) |
|---|---|---|---|---|---|
| 4-74 | Me | SO$_2$Me | Me | CH$_2$-c-Pr | * |
| 4-75 | Me | SO$_2$Me | Me | CH$_2$—CF$_3$ | |
| 4-76 | Me | Me | Me | Me | |
| 4-77 | Me | Me | Et | Me | |
| 4-78 | Me | Me | CF$_3$ | Me | |
| 4-79 | Me | Me | OMe | Me | |
| 4-80 | Me | Me | Me | Et | |
| 4-81 | Me | Me | Me | Pr | |
| 4-82 | Me | Me | Me | c-Pr | |
| 4-83 | Me | Me | Me | CH$_2$-c-Pr | |
| 4-84 | Me | Me | Me | CH$_2$—CF$_3$ | |
| 4-85 | Me | Et | Me | Me | |
| 4-86 | Me | CF$_3$ | Me | Me | |
| 4-87 | Me | CF$_3$ | Et | Me | |
| 4-88 | Me | CF$_3$ | CF$_3$ | Me | |
| 4-89 | Me | CF$_3$ | OMe | Me | |
| 4-90 | Me | CF$_3$ | Me | Et | |
| 4-91 | Me | CF$_3$ | Me | Pr | |
| 4-92 | Me | CF$_3$ | Me | c-Pr | |
| 4-93 | Me | CF$_3$ | Me | CH$_2$-c-Pr | |
| 4-94 | Me | CF$_3$ | Me | CH$_2$—CF$_3$ | |
| 4-95 | Me | SO$_2$Et | Me | Me | |
| 4-96 | Me | SO$_2$Et | Me | Et | |
| 4-97 | Me | SO$_2$Et | Me | CH$_2$-c-Pr | |
| 4-98 | Me | SO$_2$Et | Me | CH$_2$—CF$_3$ | |
| 4-99 | Me | C$_2$F$_5$ | Me | Me | |
| 4-100 | Me | c-Pr | Me | Me | |
| 4-101 | OMe | Cl | Me | Me | |
| 4-102 | OMe | CF$_3$ | Me | Me | |
| 4-103 | OMe | CF$_3$ | Me | Et | |
| 4-104 | OMe | CF$_3$ | Me | CH$_2$-c-Pr | |
| 4-105 | OMe | CF$_3$ | Me | CH$_2$—CF$_3$ | |
| 4-106 | OMe | CHF$_2$ | Me | Me | |
| 4-107 | OMe | CHF$_2$ | Et | Me | |
| 4-108 | OMe | CHF$_2$ | CF$_3$ | Me | |
| 4-109 | OMe | CHF$_2$ | OMe | Me | |
| 4-110 | OMe | CHF$_2$ | Me | Et | |
| 4-111 | OMe | CHF$_2$ | Me | Pr | |
| 4-112 | OMe | CHF$_2$ | Me | c-Pr | |
| 4-113 | OMe | CHF$_2$ | Me | CH$_2$-c-Pr | |
| 4-114 | OMe | CHF$_2$ | Me | CH$_2$—CF$_3$ | |
| 4-115 | OMe | CF$_2$Cl | Me | Me | |
| 4-116 | OMe | SO$_2$Me | Me | Me | |
| 4-117 | SO$_2$Me | CF$_3$ | Me | Me | |
| 4-118 | SO$_2$Me | CF$_3$ | Et | Me | |
| 4-119 | SO$_2$Me | CF$_3$ | CF$_3$ | Me | |
| 4-120 | SO$_2$Me | CF$_3$ | OMe | Me | |
| 4-121 | SO$_2$Me | CF$_3$ | Me | Et | |
| 4-122 | SO$_2$Me | CF$_3$ | Me | Pr | |
| 4-123 | SO$_2$Me | CF$_3$ | Me | c-Pr | |
| 4-124 | SO$_2$Me | CF$_3$ | Me | CH$_2$-c-Pr | |
| 4-125 | CH$_2$OMe | CF$_3$ | Me | CH$_2$—CF$_3$ | |
| 4-126 | SMe | CF$_3$ | Me | Me | |
| 4-127 | SMe | CF$_3$ | Me | Et | |
| 4-128 | SMe | CF$_3$ | Me | CH$_2$-c-Pr | |
| 4-129 | SMe | CF$_3$ | Me | CH$_2$—CF$_3$ | |
| 4-130 | SMe | SO$_2$Me | Me | Me | |
| 4-131 | CF$_3$ | CF$_3$ | Me | Me | |
| 4-132 | CF$_3$ | CF$_3$ | Me | Et | |
| 4-133 | CF$_3$ | CF$_3$ | Me | CH$_2$-c-Pr | |
| 4-134 | CF$_3$ | CF$_3$ | Me | CH$_2$—CF$_3$ | |
| 4-135 | F | CF$_3$ | Me | Me | |
| 4-136 | Me | SO$_2$Me | Me | i-Bu | * |

TABLE 5

Inventive compounds of the general formula (I) in which Q is Q3, $R^y$ is chlorine, and R and W are each hydrogen (E isomer, or Z isomer)

| No. | X | Y | $R^{1'}$ | $R^{2'}$ | Physical data ($^1$H NMR) |
|---|---|---|---|---|---|
| 5-1 | Cl | Cl | Me | Me | * |
| 5-2 | Cl | Cl | Et | Me | |
| 5-3 | Cl | Cl | CF$_3$ | Me | |
| 5-4 | Cl | Cl | OMe | Me | |
| 5-5 | Cl | Cl | Me | Et | * |
| 5-6 | Cl | Cl | Me | Pr | |
| 5-7 | Cl | Cl | Me | c-Pr | |
| 5-8 | Cl | Cl | Me | CH$_2$-c-Pr | * |
| 5-9 | Cl | Cl | Me | CH$_2$—CF$_3$ | * |
| 5-10 | Cl | SMe | Me | Me | |
| 5-11 | Cl | SMe | Me | Et | |
| 5-12 | Cl | SMe | Me | CH$_2$-c-Pr | |
| 5-13 | Cl | SMe | Me | CH$_2$—CF$_3$ | |
| 5-14 | Cl | S(O)Me | Me | Me | |
| 5-15 | Cl | SO$_2$Me | Me | Me | * |
| 5-16 | Cl | SO$_2$Me | Et | Me | |
| 5-17 | Cl | SO$_2$Me | CF$_3$ | Me | |
| 5-18 | Cl | SO$_2$Me | OMe | Me | |
| 5-19 | Cl | SO$_2$Me | Me | Et | |
| 5-20 | Cl | SO$_2$Me | Me | Pr | |
| 5-21 | Cl | SO$_2$Me | Me | c-Pr | |
| 5-22 | Cl | SO$_2$Me | Me | CH$_2$-c-Pr | * |
| 5-23 | Cl | SO$_2$Me | Me | CH$_2$—CF$_3$ | |
| 5-24 | Cl | Me | Me | Me | |
| 5-25 | Cl | Me | Me | Et | |
| 5-26 | Cl | Me | Me | CH$_2$-c-Pr | |
| 5-27 | Cl | Me | Me | CH$_2$—CF$_3$ | |
| 5-28 | Cl | Et | Me | Me | |
| 5-29 | Cl | c-Pr | Me | Me | |
| 5-30 | Cl | CF$_3$ | Me | Me | |
| 5-31 | Cl | CF$_3$ | Et | Me | |
| 5-32 | Cl | CF$_3$ | CF$_3$ | Me | |
| 5-33 | Cl | CF$_3$ | OMe | Me | |
| 5-34 | Cl | CF$_3$ | Me | Et | |
| 5-35 | Cl | CF$_3$ | Me | Pr | |
| 5-36 | Cl | CF$_3$ | Me | c-Pr | |
| 5-37 | Cl | CF$_3$ | Me | CH$_2$-c-Pr | |
| 5-38 | Cl | CF$_3$ | Me | CH$_2$—CF$_3$ | |
| 5-39 | Cl | OMe | Me | Me | |
| 5-40 | Cl | OMe | Me | Et | |
| 5-41 | Cl | OMe | Me | CH$_2$-c-Pr | |
| 5-42 | Cl | OMe | Me | CH$_2$—CF$_3$ | |
| 5-43 | Cl | SO$_2$Et | Me | Me | |
| 5-44 | Cl | SO$_2$Et | Me | Et | |
| 5-45 | Cl | SO$_2$Et | Me | CH$_2$-c-Pr | |
| 5-46 | Cl | SO$_2$Et | Me | CH$_2$—CF$_3$ | |
| 5-47 | Cl | C$_2$F$_5$ | Me | Me | |
| 5-48 | Cl | Vinyl | Me | Me | |
| 5-49 | Cl | 1-Me-vinyl | Me | Me | |
| 5-50 | Br | SO$_2$Me | Me | Me | |
| 5-51 | Br | SO$_2$Me | Et | Me | |
| 5-52 | Br | SO$_2$Me | CF$_3$ | Me | |
| 5-53 | Br | SO$_2$Me | OMe | Me | |
| 5-54 | Br | SO$_2$Me | Me | Et | |
| 5-55 | Br | SO$_2$Me | Me | Pr | |
| 5-56 | Br | SO$_2$Me | Me | c-Pr | |
| 5-57 | Br | SO$_2$Me | Me | CH$_2$-c-Pr | |
| 5-58 | Br | SO$_2$Me | Me | CH$_2$—CF$_3$ | |
| 5-59 | Br | Me | Me | Me | |
| 5-60 | Br | Et | Me | Me | |
| 5-61 | Br | CF$_3$ | Me | Me | |
| 5-62 | Br | CF$_3$ | Me | Et | |
| 5-63 | Br | CF$_3$ | Me | CH$_2$-c-Pr | |
| 5-64 | Br | CF$_3$ | Me | CH$_2$—CF$_3$ | |

TABLE 5-continued

Inventive compounds of the general formula (I) in which Q is Q3, R$^y$ is chlorine, and R and W are each hydrogen (E isomer, or Z isomer)

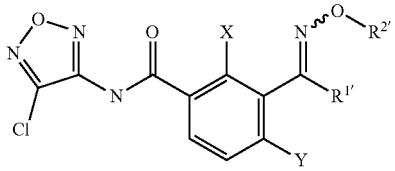

| No. | X | Y | R$^{1'}$ | R$^{2'}$ | Physical data ($^1$H NMR) |
|---|---|---|---|---|---|
| 5-65 | Me | SMe | Me | Me | |
| 5-66 | Me | S(O)Me | Me | Me | |
| 5-67 | Me | SO$_2$Me | Me | Me | * |
| 5-68 | Me | SO$_2$Me | Et | Me | |
| 5-69 | Me | SO$_2$Me | CF$_3$ | Me | |
| 5-70 | Me | SO$_2$Me | OMe | Me | |
| 5-71 | Me | SO$_2$Me | Me | Et | * |
| 5-72 | Me | SO$_2$Me | Me | Pr | |
| 5-73 | Me | SO$_2$Me | Me | c-Pr | |
| 5-74 | Me | SO$_2$Me | Me | CH$_2$-c-Pr | * |
| 5-75 | Me | SO$_2$Me | Me | CH$_2$—CF$_3$ | |
| 5-76 | Me | Me | Me | Me | |
| 5-77 | Me | Me | Et | Me | |
| 5-78 | Me | Me | CF$_3$ | Me | |
| 5-79 | Me | Me | OMe | Me | |
| 5-80 | Me | Me | Me | Et | |
| 5-81 | Me | Me | Me | Pr | |
| 5-82 | Me | Me | Me | c-Pr | |
| 5-83 | Me | Me | Me | CH$_2$-c-Pr | |
| 5-84 | Me | Me | Me | CH$_2$—CF$_3$ | |
| 5-85 | Me | Et | Me | Me | |
| 5-86 | Me | CF$_3$ | Me | Me | |
| 5-87 | Me | CF$_3$ | Et | Me | |
| 5-88 | Me | CF$_3$ | CF$_3$ | Me | |
| 5-89 | Me | CF$_3$ | OMe | Me | |
| 5-90 | Me | CF$_3$ | Me | Et | |
| 5-91 | Me | CF$_3$ | Me | Pr | |
| 5-92 | Me | CF$_3$ | Me | c-Pr | |
| 5-93 | Me | CF$_3$ | Me | CH$_2$-c-Pr | |
| 5-94 | Me | CF$_3$ | Me | CH$_2$—CF$_3$ | |
| 5-95 | Me | SO$_2$Et | Me | Me | |
| 5-96 | Me | SO$_2$Et | Me | Et | |
| 5-97 | Me | SO$_2$Et | Me | CH$_2$-c-Pr | |
| 5-98 | Me | SO$_2$Et | Me | CH$_2$—CF$_3$ | |
| 5-99 | Me | C$_2$F$_5$ | Me | Me | |
| 5-100 | Me | c-Pr | Me | Me | |
| 5-101 | OMe | Cl | Me | Me | |
| 5-102 | OMe | CF$_3$ | Me | Me | |
| 5-103 | OMe | CF$_3$ | Me | Et | |
| 5-104 | OMe | CF$_3$ | Me | CH$_2$-c-Pr | |
| 5-105 | OMe | CF$_3$ | Me | CH$_2$—CF$_3$ | |
| 5-106 | OMe | CHF$_2$ | Me | Me | |
| 5-107 | OMe | CHF$_2$ | Et | Me | |
| 5-108 | OMe | CHF$_2$ | CF$_3$ | Me | |
| 5-109 | OMe | CHF$_2$ | OMe | Me | |
| 5-110 | OMe | CHF$_2$ | Me | Et | |
| 5-111 | OMe | CHF$_2$ | Me | Pr | |
| 5-112 | OMe | CHF$_2$ | Me | c-Pr | |
| 5-113 | OMe | CHF$_2$ | Me | CH$_2$-c-Pr | |
| 5-114 | OMe | CHF$_2$ | Me | CH$_2$—CF$_3$ | |
| 5-115 | OMe | CF$_2$Cl | Me | Me | |
| 5-116 | OMe | SO$_2$Me | Me | Me | |
| 5-117 | SO$_2$Me | CF$_3$ | Me | Me | |
| 5-118 | SO$_2$Me | CF$_3$ | Et | Me | |
| 5-119 | SO$_2$Me | CF$_3$ | CF$_3$ | Me | |
| 5-120 | SO$_2$Me | CF$_3$ | OMe | Me | |
| 5-121 | SO$_2$Me | CF$_3$ | Me | Et | |
| 5-122 | SO$_2$Me | CF$_3$ | Me | Pr | |
| 5-123 | SO$_2$Me | CF$_3$ | Me | c-Pr | |
| 5-124 | SO$_2$Me | CF$_3$ | Me | CH$_2$-c-Pr | |
| 5-125 | CH$_2$OMe | CF$_3$ | Me | CH$_2$—CF$_3$ | |
| 5-126 | SMe | CF$_3$ | Me | Me | |
| 5-127 | SMe | CF$_3$ | Me | Et | |
| 5-128 | SMe | CF$_3$ | Me | CH$_2$-c-Pr | |
| 5-129 | SMe | CF$_3$ | Me | CH$_2$—CF$_3$ | |
| 5-130 | SMe | SO$_2$Me | Me | Me | |
| 5-131 | CF$_3$ | CF$_3$ | Me | Me | |
| 5-132 | CF$_3$ | CF$_3$ | Me | Et | |
| 5-133 | CF$_3$ | CF$_3$ | Me | CH$_2$-c-Pr | |
| 5-134 | CF$_3$ | CF$_3$ | Me | CH$_2$—CF$_3$ | |
| 5-135 | F | CF$_3$ | Me | Me | |
| 5-136 | Me | SO$_2$Me | Me | i-Bu | |

TABLE 6

Inventive compounds of the general formula (I) in which Q is Q3, R$^y$ is a methyl group, and R and W are each hydrogen (E isomer, or Z isomer)

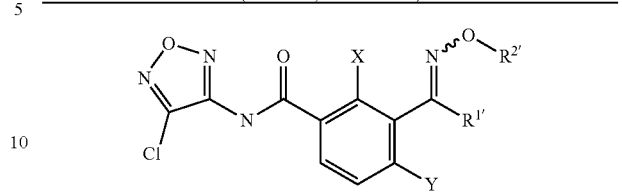

| No. | X | Y | R$^{1'}$ | R$^{2'}$ | Physical data ($^1$H NMR) |
|---|---|---|---|---|---|
| 6-1 | Cl | Cl | Me | Me | * |
| 6-2 | Cl | Cl | Et | Me | |
| 6-3 | Cl | Cl | CF$_3$ | Me | |
| 6-4 | Cl | Cl | OMe | Me | |
| 6-5 | Cl | Cl | Me | Et | * |
| 6-6 | Cl | Cl | Me | Pr | |
| 6-7 | Cl | Cl | Me | c-Pr | |
| 6-8 | Cl | Cl | Me | CH$_2$-c-Pr | * |
| 6-9 | Cl | Cl | Me | CH$_2$—CF$_3$ | * |
| 6-10 | Cl | SMe | Me | Me | |
| 6-11 | Cl | SMe | Me | Et | |
| 6-12 | Cl | SMe | Me | CH$_2$-c-Pr | |
| 6-13 | Cl | SMe | Me | CH$_2$—CF$_3$ | |
| 6-14 | Cl | S(O)Me | Me | Me | |
| 6-15 | Cl | SO$_2$Me | Me | Me | * |
| 6-16 | Cl | SO$_2$Me | Et | Me | |
| 6-17 | Cl | SO$_2$Me | CF$_3$ | Me | |
| 6-18 | Cl | SO$_2$Me | OMe | Me | |
| 6-19 | Cl | SO$_2$Me | Me | Et | * |
| 6-20 | Cl | SO$_2$Me | Me | Pr | |
| 6-21 | Cl | SO$_2$Me | Me | c-Pr | |
| 6-22 | Cl | SO$_2$Me | Me | CH$_2$-c-Pr | * |
| 6-23 | Cl | SO$_2$Me | Me | CH$_2$—CF$_3$ | |
| 6-24 | Cl | Me | Me | Me | |
| 6-25 | Cl | Me | Me | Et | |
| 6-26 | Cl | Me | Me | CH$_2$-c-Pr | |
| 6-27 | Cl | Me | Me | CH$_2$—CF$_3$ | |
| 6-28 | Cl | Et | Me | Me | |
| 6-29 | Cl | c-Pr | Me | Me | |
| 6-30 | Cl | CF$_3$ | Me | Me | |
| 6-31 | Cl | CF$_3$ | Et | Me | |
| 6-32 | Cl | CF$_3$ | CF$_3$ | Me | |
| 6-33 | Cl | CF$_3$ | OMe | Me | |
| 6-34 | Cl | CF$_3$ | Me | Et | |

TABLE 6-continued

Inventive compounds of the general formula (I) in which Q is Q3, $R^y$ is a methyl group, and R and W are each hydrogen (E isomer, or Z isomer)

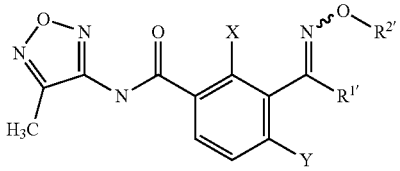

| No. | X | Y | $R^{1'}$ | $R^{2'}$ | Physical data ($^1$H NMR) |
|---|---|---|---|---|---|
| 6-35 | Cl | CF$_3$ | Me | Pr | |
| 6-36 | Cl | CF$_3$ | Me | c-Pr | |
| 6-37 | Cl | CF$_3$ | Me | CH$_2$-c-Pr | |
| 6-38 | Cl | CF$_3$ | Me | CH$_2$—CF$_3$ | |
| 6-39 | Cl | OMe | Me | Me | |
| 6-40 | Cl | OMe | Me | Et | |
| 6-41 | Cl | OMe | Me | CH$_2$-c-Pr | |
| 6-42 | Cl | OMe | Me | CH$_2$—CF$_3$ | |
| 6-43 | Cl | SO$_2$Et | Me | Me | |
| 6-44 | Cl | SO$_2$Et | Me | Et | |
| 6-45 | Cl | SO$_2$Et | Me | CH$_2$-c-Pr | |
| 6-46 | Cl | SO$_2$Et | Me | CH$_2$—CF$_3$ | |
| 6-47 | Cl | C$_2$F$_5$ | Me | Me | |
| 6-48 | Cl | Vinyl | Me | Me | |
| 6-49 | Cl | 1-Me-vinyl | Me | Me | |
| 6-50 | Br | SO$_2$Me | Me | Me | |
| 6-51 | Br | SO$_2$Me | Et | Me | |
| 6-52 | Br | SO$_2$Me | CF$_3$ | Me | |
| 6-53 | Br | SO$_2$Me | OMe | Me | |
| 6-54 | Br | SO$_2$Me | Me | Et | |
| 6-55 | Br | SO$_2$Me | Me | Pr | |
| 6-56 | Br | SO$_2$Me | Me | c-Pr | |
| 6-57 | Br | SO$_2$Me | Me | CH$_2$-c-Pr | |
| 6-58 | Br | SO$_2$Me | Me | CH$_2$—CF$_3$ | |
| 6-59 | Br | Me | Me | Me | |
| 6-60 | Br | Et | Me | Me | |
| 6-61 | Br | CF$_3$ | Me | Me | |
| 6-62 | Br | CF$_3$ | Me | Et | |
| 6-63 | Br | CF$_3$ | Me | CH$_2$-c-Pr | |
| 6-64 | Br | CF$_3$ | Me | CH$_2$—CF$_3$ | |
| 6-65 | Me | SMe | Me | Me | |
| 6-66 | Me | S(O)Me | Me | Me | |
| 6-67 | Me | SO$_2$Me | Me | Me | * |
| 6-68 | Me | SO$_2$Me | Et | Me | |
| 6-69 | Me | SO$_2$Me | CF$_3$ | Me | |
| 6-70 | Me | SO$_2$Me | OMe | Me | |
| 6-71 | Me | SO$_2$Me | Me | Et | * |
| 6-72 | Me | SO$_2$Me | Me | Pr | |
| 6-73 | Me | SO$_2$Me | Me | c-Pr | |
| 6-74 | Me | SO$_2$Me | Me | CH$_2$-c-Pr | * |
| 6-75 | Me | SO$_2$Me | Me | CH$_2$—CF$_3$ | |
| 6-76 | Me | Me | Me | Me | |
| 6-77 | Me | Me | Et | Me | |
| 6-78 | Me | Me | CF$_3$ | Me | |
| 6-79 | Me | Me | OMe | Me | |
| 6-80 | Me | Me | Me | Et | |
| 6-81 | Me | Me | Me | Pr | |
| 6-82 | Me | Me | Me | c-Pr | |
| 6-83 | Me | Me | Me | CH$_2$-c-Pr | |
| 6-84 | Me | Me | Me | CH$_2$—CF$_3$ | |
| 6-85 | Me | Et | Me | Me | |
| 6-86 | Me | CF$_3$ | Me | Me | |
| 6-87 | Me | CF$_3$ | Et | Me | |
| 6-88 | Me | CF$_3$ | CF$_3$ | Me | |
| 6-89 | Me | CF$_3$ | OMe | Me | |
| 6-90 | Me | CF$_3$ | Me | Et | |
| 6-91 | Me | CF$_3$ | Me | Pr | |
| 6-92 | Me | CF$_3$ | Me | c-Pr | |
| 6-93 | Me | CF$_3$ | Me | CH$_2$-c-Pr | |
| 6-94 | Me | CF$_3$ | Me | CH$_2$—CF$_3$ | |
| 6-95 | Me | SO$_2$Et | Me | Me | |
| 6-96 | Me | SO$_2$Et | Me | Et | |
| 6-97 | Me | SO$_2$Et | Me | CH$_2$-c-Pr | |
| 6-98 | Me | SO$_2$Et | Me | CH$_2$—CF$_3$ | |
| 6-99 | Me | C$_2$F$_5$ | Me | Me | |
| 6-100 | Me | c-Pr | Me | Me | |
| 6-101 | OMe | Cl | Me | Me | |
| 6-102 | OMe | CF$_3$ | Me | Me | |
| 6-103 | OMe | CF$_3$ | Me | Et | |
| 6-104 | OMe | CF$_3$ | Me | CH$_2$-c-Pr | |
| 6-105 | OMe | CF$_3$ | Me | CH$_2$—CF$_3$ | |
| 6-106 | OMe | CHF$_2$ | Me | Me | |
| 6-107 | OMe | CHF$_2$ | Et | Me | |
| 6-108 | OMe | CHF$_2$ | CF$_3$ | Me | |
| 6-109 | OMe | CHF$_2$ | OMe | Me | |
| 6-110 | OMe | CHF$_2$ | Me | Et | |
| 6-111 | OMe | CHF$_2$ | Me | Pr | |
| 6-112 | OMe | CHF$_2$ | Me | c-Pr | |
| 6-113 | OMe | CHF$_2$ | Me | CH$_2$-c-Pr | |
| 6-114 | OMe | CHF$_2$ | Me | CH$_2$—CF$_3$ | |
| 6-115 | OMe | CF$_2$Cl | Me | Me | |
| 6-116 | OMe | SO$_2$Me | Me | Me | |
| 6-117 | SO$_2$Me | CF$_3$ | Me | Me | |
| 6-118 | SO$_2$Me | CF$_3$ | Et | Me | |
| 6-119 | SO$_2$Me | CF$_3$ | CF$_3$ | Me | |
| 6-120 | SO$_2$Me | CF$_3$ | OMe | Me | |
| 6-121 | SO$_2$Me | CF$_3$ | Me | Et | |
| 6-122 | SO$_2$Me | CF$_3$ | Me | Pr | |
| 6-123 | SO$_2$Me | CF$_3$ | Me | c-Pr | |
| 6-124 | SO$_2$Me | CF$_3$ | Me | CH$_2$-c-Pr | |
| 6-125 | CH$_2$OMe | CF$_3$ | Me | CH$_2$—CF$_3$ | |
| 6-126 | SMe | CF$_3$ | Me | Me | |
| 6-127 | SMe | CF$_3$ | Me | Et | |
| 6-128 | SMe | CF$_3$ | Me | CH$_2$-c-Pr | |
| 6-129 | SMe | CF$_3$ | Me | CH$_2$—CF$_3$ | |
| 6-130 | SMe | SO$_2$Me | Me | Me | |
| 6-131 | CF$_3$ | CF$_3$ | Me | Me | |
| 6-132 | CF$_3$ | CF$_3$ | Me | Et | |
| 6-133 | CF$_3$ | CF$_3$ | Me | CH$_2$-c-Pr | |
| 6-134 | CF$_3$ | CF$_3$ | Me | CH$_2$—CF$_3$ | |
| 6-135 | F | CF$_3$ | Me | Me | |
| 6-136 | Me | SO$_2$Me | Me | i-Bu | |

TABLE 7

Inventive compounds of the general formula (I) in which Q is Q4, $R^z$ is a methyl group, and R and W are each hydrogen (E isomer, or Z isomer)

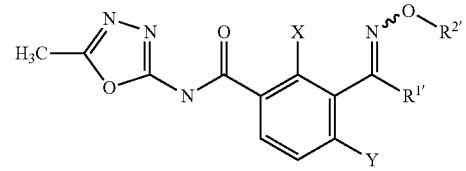

| No. | X | Y | $R^{1'}$ | $R^{2'}$ | Physical data ($^1$H NMR) |
|---|---|---|---|---|---|
| 7-1 | Cl | Cl | Me | Me | * |
| 7-2 | Cl | Cl | Et | Me | |
| 7-3 | Cl | Cl | CF$_3$ | Me | |
| 7-4 | Cl | Cl | OMe | Me | |

TABLE 7-continued

Inventive compounds of the general formula (I) in which Q is Q4, $R^z$ is a methyl group, and R and W are each hydrogen (E isomer, or Z isomer)

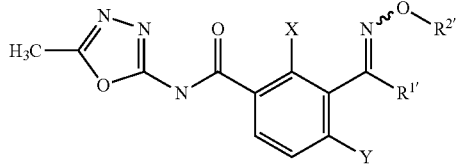

| No. | X | Y | $R^{1'}$ | $R^{2'}$ | Physical data ($^1$H NMR) |
|---|---|---|---|---|---|
| 7-5 | Cl | Cl | Me | Et | * |
| 7-6 | Cl | Cl | Me | Pr | |
| 7-7 | Cl | Cl | Me | c-Pr | |
| 7-8 | Cl | Cl | Me | $CH_2$-c-Pr | * |
| 7-9 | Cl | Cl | Me | $CH_2$—$CF_3$ | * |
| 7-10 | Cl | SMe | Me | Me | |
| 7-11 | Cl | SMe | Me | Et | |
| 7-12 | Cl | SMe | Me | $CH_2$-c-Pr | |
| 7-13 | Cl | SMe | Me | $CH_2$—$CF_3$ | |
| 7-14 | Cl | S(O)Me | Me | Me | |
| 7-15 | Cl | $SO_2Me$ | Me | Me | * |
| 7-16 | Cl | $SO_2Me$ | Et | Me | |
| 7-17 | Cl | $SO_2Me$ | $CF_3$ | Me | |
| 7-18 | Cl | $SO_2Me$ | OMe | Me | |
| 7-19 | Cl | $SO_2Me$ | Me | Et | * |
| 7-20 | Cl | $SO_2Me$ | Me | Pr | |
| 7-21 | Cl | $SO_2Me$ | Me | c-Pr | |
| 7-22 | Cl | $SO_2Me$ | Me | $CH_2$-c-Pr | * |
| 7-23 | Cl | $SO_2Me$ | Me | $CH_2$—$CF_3$ | |
| 7-24 | Cl | Me | Me | Me | |
| 7-25 | Cl | Me | Me | Et | |
| 7-26 | Cl | Me | Me | $CH_2$-c-Pr | |
| 7-27 | Cl | Me | Me | $CH_2$—$CF_3$ | |
| 7-28 | Cl | Et | Me | Me | |
| 7-29 | Cl | c-Pr | Me | Me | |
| 7-30 | Cl | $CF_3$ | Me | Me | |
| 7-31 | Cl | $CF_3$ | Et | Me | |
| 7-32 | Cl | $CF_3$ | $CF_3$ | Me | |
| 7-33 | Cl | $CF_3$ | OMe | Me | |
| 7-34 | Cl | $CF_3$ | Me | Et | |
| 7-35 | Cl | $CF_3$ | Me | Pr | |
| 7-36 | Cl | $CF_3$ | Me | c-Pr | |
| 7-37 | Cl | $CF_3$ | Me | $CH_2$-c-Pr | |
| 7-38 | Cl | $CF_3$ | Me | $CH_2$—$CF_3$ | |
| 7-39 | Cl | OMe | Me | Me | |
| 7-40 | Cl | OMe | Me | Et | |
| 7-41 | Cl | OMe | Me | $CH_2$-c-Pr | |
| 7-42 | Cl | OMe | Me | $CH_2$—$CF_3$ | |
| 7-43 | Cl | $SO_2Et$ | Me | Me | |
| 7-44 | Cl | $SO_2Et$ | Me | Et | |
| 7-45 | Cl | $SO_2Et$ | Me | $CH_2$-c-Pr | |
| 7-46 | Cl | $SO_2Et$ | Me | $CH_2$—$CF_3$ | |
| 7-47 | Cl | $C_2F_5$ | Me | Me | |
| 7-48 | Cl | Vinyl | Me | Me | |
| 7-49 | Cl | 1-Me-vinyl | Me | Me | |
| 7-50 | Br | $SO_2Me$ | Me | Me | |
| 7-51 | Br | $SO_2Me$ | Et | Me | |
| 7-52 | Br | $SO_2Me$ | $CF_3$ | Me | |
| 7-53 | Br | $SO_2Me$ | OMe | Me | |
| 7-54 | Br | $SO_2Me$ | Me | Et | |
| 7-55 | Br | $SO_2Me$ | Me | Pr | |
| 7-56 | Br | $SO_2Me$ | Me | c-Pr | |
| 7-57 | Br | $SO_2Me$ | Me | $CH_2$-c-Pr | |
| 7-58 | Br | $SO_2Me$ | Me | $CH_2$—$CF_3$ | |
| 7-59 | Br | Me | Me | Me | |
| 7-60 | Br | Et | Me | Me | |
| 7-61 | Br | $CF_3$ | Me | Me | |
| 7-62 | Br | $CF_3$ | Me | Et | |
| 7-63 | Br | $CF_3$ | Me | $CH_2$-c-Pr | |
| 7-64 | Br | $CF_3$ | Me | $CH_2$—$CF_3$ | |
| 7-65 | Me | SMe | Me | Me | |
| 7-66 | Me | S(O)Me | Me | Me | |
| 7-67 | Me | $SO_2Me$ | Me | Me | |
| 7-68 | Me | $SO_2Me$ | Et | Me | |
| 7-69 | Me | $SO_2Me$ | $CF_3$ | Me | |
| 7-70 | Me | $SO_2Me$ | OMe | Me | |
| 7-71 | Me | $SO_2Me$ | Me | Et | * |
| 7-72 | Me | $SO_2Me$ | Me | Pr | |
| 7-73 | Me | $SO_2Me$ | Me | c-Pr | |
| 7-74 | Me | $SO_2Me$ | Me | $CH_2$-c-Pr | |
| 7-75 | Me | $SO_2Me$ | Me | $CH_2$—$CF_3$ | |
| 7-76 | Me | Me | Me | Me | |
| 7-77 | Me | Me | Me | Et | |
| 7-78 | Me | Me | $CF_3$ | Me | |
| 7-79 | Me | Me | OMe | Me | |
| 7-80 | Me | Me | Me | Et | |
| 7-81 | Me | Me | Me | Pr | |
| 7-82 | Me | Me | Me | c-Pr | |
| 7-83 | Me | Me | Me | $CH_2$-c-Pr | |
| 7-84 | Me | Me | Me | $CH_2$—$CF_3$ | |
| 7-85 | Me | Et | Me | Me | |
| 7-86 | Me | $CF_3$ | Me | Me | |
| 7-87 | Me | $CF_3$ | Et | Me | |
| 7-88 | Me | $CF_3$ | $CF_3$ | Me | |
| 7-89 | Me | $CF_3$ | OMe | Me | |
| 7-90 | Me | $CF_3$ | Me | Et | |
| 7-91 | Me | $CF_3$ | Me | Pr | |
| 7-92 | Me | $CF_3$ | Me | c-Pr | |
| 7-93 | Me | $CF_3$ | Me | $CH_2$-c-Pr | |
| 7-94 | Me | $CF_3$ | Me | $CH_2$—$CF_3$ | |
| 7-95 | Me | $SO_2Et$ | Me | Me | |
| 7-96 | Me | $SO_2Et$ | Me | Et | |
| 7-97 | Me | $SO_2Et$ | Me | $CH_2$-c-Pr | |
| 7-98 | Me | $SO_2Et$ | Me | $CH_2$—$CF_3$ | |
| 7-99 | Me | $C_2F_5$ | Me | Me | |
| 7-100 | Me | c-Pr | Me | Me | |
| 7-101 | OMe | Cl | Me | Me | |
| 7-102 | OMe | $CF_3$ | Me | Me | |
| 7-103 | OMe | $CF_3$ | Me | Et | |
| 7-104 | OMe | $CF_3$ | Me | $CH_2$-c-Pr | |
| 7-105 | OMe | $CF_3$ | Me | $CH_2$—$CF_3$ | |
| 7-106 | OMe | $CHF_2$ | Me | Me | |
| 7-107 | OMe | $CHF_2$ | Et | Me | |
| 7-108 | OMe | $CHF_2$ | $CF_3$ | Me | |
| 7-109 | OMe | $CHF_2$ | OMe | Me | |
| 7-110 | OMe | $CHF_2$ | Me | Et | |
| 7-111 | OMe | $CHF_2$ | Me | Pr | |
| 7-112 | OMe | $CHF_2$ | Me | c-Pr | |
| 7-113 | OMe | $CHF_2$ | Me | $CH_2$-c-Pr | |
| 7-114 | OMe | $CHF_2$ | Me | $CH_2$—$CF_3$ | |
| 7-115 | OMe | $CF_2Cl$ | Me | Me | |
| 7-116 | OMe | $SO_2Me$ | Me | Me | |
| 7-117 | $SO_2Me$ | $CF_3$ | Me | Me | |
| 7-118 | $SO_2Me$ | $CF_3$ | Et | Me | |
| 7-119 | $SO_2Me$ | $CF_3$ | $CF_3$ | Me | |
| 7-120 | $SO_2Me$ | $CF_3$ | OMe | Me | |
| 7-121 | $SO_2Me$ | $CF_3$ | Me | Et | |
| 7-122 | $SO_2Me$ | $CF_3$ | Me | Pr | |
| 7-123 | $SO_2Me$ | $CF_3$ | Me | c-Pr | |
| 7-124 | $SO_2Me$ | $CF_3$ | Me | $CH_2$-c-Pr | |
| 7-125 | $CH_2OMe$ | $CF_3$ | Me | $CH_2$—$CF_3$ | |
| 7-126 | SMe | $CF_3$ | Me | Me | |
| 7-127 | SMe | $CF_3$ | Me | Et | |
| 7-128 | SMe | $CF_3$ | Me | $CH_2$-c-Pr | |
| 7-129 | SMe | $CF_3$ | Me | $CH_2$—$CF_3$ | |
| 7-130 | SMe | $SO_2Me$ | Me | Me | |
| 7-131 | $CF_3$ | $CF_3$ | Me | Me | |
| 7-132 | $CF_3$ | $CF_3$ | Me | Et | |

TABLE 7-continued

Inventive compounds of the general formula (I) in which Q is Q4, $R^z$ is a methyl group, and R and W are each hydrogen (E isomer, or Z isomer)

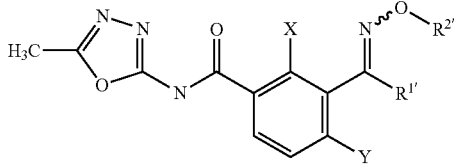

| No. | X | Y | $R^{1'}$ | $R^{2'}$ | Physical data ($^1$H NMR) |
|---|---|---|---|---|---|
| 7-133 | $CF_3$ | $CF_3$ | Me | $CH_2$-c-Pr | |
| 7-134 | $CF_3$ | $CF_3$ | Me | $CH_2$—$CF_3$ | |
| 7-135 | F | $CF_3$ | Me | Me | |
| 7-136 | Me | $SO_2Me$ | Me | i-Bu | |

TABLE 8

Inventive compounds of the general formula (I) in which Q is Q1, $R^x$ is a methyl group, and R and W are each hydrogen (Z isomer, or E isomer)

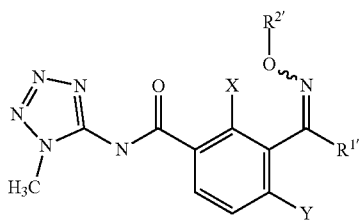

| No. | X | Y | $R^{1'}$ | $R^{2'}$ | Physical data ($^1$H NMR) |
|---|---|---|---|---|---|
| 8-1 | Cl | Cl | Me | Me | |
| 8-2 | Cl | Cl | Me | Et | |
| 8-3 | Cl | Cl | Me | $CH_2$-c-Pr | |
| 8-4 | Cl | Cl | Me | $CH_2$—$CF_3$ | |
| 8-5 | Cl | $SO_2Me$ | Me | Me | * |
| 8-6 | Cl | $SO_2Me$ | Me | Et | |
| 8-7 | Cl | $SO_2Me$ | Me | $CH_2$-c-Pr | |
| 8-8 | Cl | $SO_2Me$ | Me | $CH_2$—$CF_3$ | |
| 8-9 | Cl | Me | Me | Me | |
| 8-10 | Cl | Me | Me | Et | |
| 8-11 | Cl | Me | Me | $CH_2$-c-Pr | |
| 8-12 | Cl | Me | Me | $CH_2$—$CF_3$ | |
| 8-13 | Cl | $CF_3$ | Me | Me | |
| 8-14 | Cl | $CF_3$ | Me | Et | |
| 8-15 | Cl | $CF_3$ | Me | $CH_2$-c-Pr | |
| 8-16 | Cl | $CF_3$ | Me | $CH_2$—$CF_3$ | |
| 8-17 | Br | $SO_2Me$ | Me | Me | |
| 8-18 | Br | $SO_2Me$ | Me | Et | |
| 8-19 | Br | $SO_2Me$ | Me | $CH_2$-c-Pr | |
| 8-20 | Br | $SO_2Me$ | Me | $CH_2$—$CF_3$ | |
| 8-21 | Br | $CF_3$ | Me | Me | |
| 8-22 | Br | $CF_3$ | Me | Et | |
| 8-23 | Br | $CF_3$ | Me | $CH_2$-c-Pr | |
| 8-24 | Br | $CF_3$ | Me | $CH_2$—$CF_3$ | |
| 8-25 | Me | $SO_2Me$ | Me | Me | * |
| 8-26 | Me | $SO_2Me$ | Me | Et | * |
| 8-27 | Me | $SO_2Me$ | Me | $CH_2$-c-Pr | |
| 8-28 | Me | $SO_2Me$ | Me | $CH_2$—$CF_3$ | |
| 8-29 | Me | $CF_3$ | Me | Me | |
| 8-30 | Me | $CF_3$ | Me | Et | |
| 8-31 | Me | $CF_3$ | Me | $CH_2$-c-Pr | |
| 8-32 | Me | $CF_3$ | Me | $CH_2$—$CF_3$ | |
| 8-33 | OMe | $CF_3$ | Me | Me | |
| 8-34 | OMe | $CF_3$ | Me | Et | |
| 8-35 | OMe | $CF_3$ | Me | $CH_2$-c-Pr | |
| 8-36 | OMe | $CF_3$ | Me | $CH_2$—$CF_3$ | |
| 8-37 | OMe | $CHF_2$ | Me | Me | |
| 8-38 | OMe | $CHF_2$ | Me | Et | |

TABLE 8-continued

Inventive compounds of the general formula (I) in which Q is Q1, $R^x$ is a methyl group, and R and W are each hydrogen (Z isomer, or E isomer)

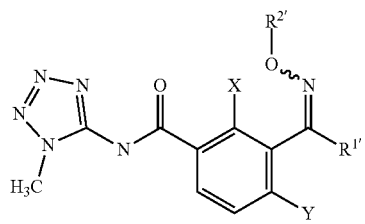

| No. | X | Y | $R^{1'}$ | $R^{2'}$ | Physical data ($^1$H NMR) |
|---|---|---|---|---|---|
| 8-39 | OMe | $CHF_2$ | Me | $CH_2$-c-Pr | |
| 8-40 | OMe | $CHF_2$ | Me | $CH_2$—$CF_3$ | |
| 8-41 | $SO2Me$ | $CF_3$ | Me | Me | |
| 8-42 | $SO2Me$ | $CF_3$ | Me | Et | |
| 8-43 | $SO2Me$ | $CF_3$ | Me | $CH_2$-c-Pr | |
| 8-44 | $SO2Me$ | $CF_3$ | Me | $CH_2$—$CF_3$ | |
| 8-45 | Me | $SO_2Me$ | Me | i-Bu | |

TABLE 9

Inventive compounds of the general formula (I) in which Q is Q1, $R^x$ is an ethyl group, and R and W are each hydrogen (Z isomer, or E isomer)

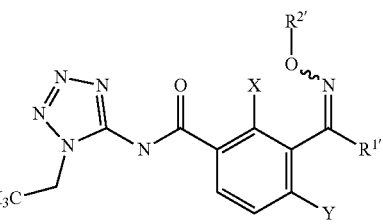

| No. | X | Y | $R^{1'}$ | $R^{2'}$ | Physical data ($^1$H NMR) |
|---|---|---|---|---|---|
| 9-1 | Cl | Cl | Me | Me | |
| 9-2 | Cl | Cl | Me | Et | |
| 9-3 | Cl | Cl | Me | $CH_2$-c-Pr | |
| 9-4 | Cl | Cl | Me | $CH_2$—$CF_3$ | |
| 9-5 | Cl | $SO_2Me$ | Me | Me | * |
| 9-6 | Cl | $SO_2Me$ | Me | Et | |
| 9-7 | Cl | $SO_2Me$ | Me | $CH_2$-c-Pr | |
| 9-8 | Cl | $SO_2Me$ | Me | $CH_2$—$CF_3$ | |
| 9-9 | Cl | Me | Me | Me | |
| 9-10 | Cl | Me | Me | Et | |
| 9-11 | Cl | Me | Me | $CH_2$-c-Pr | |
| 9-12 | Cl | Me | Me | $CH_2$—$CF_3$ | |
| 9-13 | Cl | $CF_3$ | Me | Me | |
| 9-14 | Cl | $CF_3$ | Me | Et | |
| 9-15 | Cl | $CF_3$ | Me | $CH_2$-c-Pr | |
| 9-16 | Cl | $CF_3$ | Me | $CH_2$—$CF_3$ | |
| 9-17 | Br | $SO_2Me$ | Me | Me | |
| 9-18 | Br | $SO_2Me$ | Me | Et | |
| 9-19 | Br | $SO_2Me$ | Me | $CH_2$-c-Pr | |
| 9-20 | Br | $SO_2Me$ | Me | $CH_2$—$CF_3$ | |
| 9-21 | Br | $CF_3$ | Me | Me | |
| 9-22 | Br | $CF_3$ | Me | Et | |
| 9-23 | Br | $CF_3$ | Me | $CH_2$-c-Pr | |
| 9-24 | Br | $CF_3$ | Me | $CH_2$—$CF_3$ | |
| 9-25 | Me | $SO_2Me$ | Me | Me | * |
| 9-26 | Me | $SO_2Me$ | Me | Et | |
| 9-27 | Me | $SO_2Me$ | Me | $CH_2$-c-Pr | |
| 9-28 | Me | $SO_2Me$ | Me | $CH_2$—$CF_3$ | |
| 9-29 | Me | $CF_3$ | Me | Me | |
| 9-30 | Me | $CF_3$ | Me | Et | |
| 9-31 | Me | $CF_3$ | Me | $CH_2$-c-Pr | |
| 9-32 | Me | $CF_3$ | Me | $CH_2$—$CF_3$ | |
| 9-33 | OMe | $CF_3$ | Me | Me | |
| 9-34 | OMe | $CF_3$ | Me | Et | |
| 9-35 | OMe | $CF_3$ | Me | $CH_2$-c-Pr | |

TABLE 9-continued

Inventive compounds of the general formula (I) in which Q is Q1, $R^x$ is an ethyl group, and R and W are each hydrogen (Z isomer, or E isomer)

| No. | X | Y | $R^{1'}$ | $R^{2'}$ | Physical data ($^1$H NMR) |
|---|---|---|---|---|---|
| 9-36 | OMe | $CF_3$ | Me | $CH_2$—$CF_3$ | |
| 9-37 | OMe | $CHF_2$ | Me | Me | |
| 9-38 | OMe | $CHF_2$ | Me | Et | |
| 9-39 | OMe | $CHF_2$ | Me | $CH_2$—c-Pr | |
| 9-40 | OMe | $CHF_2$ | Me | $CH_2$—$CF_3$ | |
| 9-41 | $SO_2Me$ | $CF_3$ | Me | Me | |
| 9-42 | $SO_2Me$ | $CF_3$ | Me | Et | |
| 9-43 | $SO_2Me$ | $CF_3$ | Me | $CH_2$—c-Pr | |
| 9-44 | $SO_2Me$ | $CF_3$ | Me | $CH_2$—$CF_3$ | |
| 9-45 | Me | $SO_2Me$ | Me | i-Bu | |

TABLE 10

Inventive compounds of the general formula (I) in which Q is Q1, $R^x$ is a propyl group, and R and W are each hydrogen (Z isomer, or E isomer)

| No. | X | Y | $R^{1'}$ | $R^{2'}$ | Physical data ($^1$H NMR) |
|---|---|---|---|---|---|
| 10-1 | Cl | Cl | Me | Me | |
| 10-2 | Cl | Cl | Me | Et | |
| 10-3 | Cl | Cl | Me | $CH_2$—c-Pr | |
| 10-4 | Cl | Cl | Me | $CH_2$—$CF_3$ | |
| 10-5 | Cl | $SO_2Me$ | Me | Me | * |
| 10-6 | Cl | $SO_2Me$ | Me | Et | |
| 10-7 | Cl | $SO_2Me$ | Me | $CH_2$—c-Pr | |
| 10-8 | Cl | $SO_2Me$ | Me | $CH_2$—$CF_3$ | |
| 10-9 | Cl | Me | Me | Me | |
| 10-10 | Cl | Me | Me | Et | |
| 10-11 | Cl | Me | Me | $CH_2$—c-Pr | |
| 10-12 | Cl | Me | Me | $CH_2$—$CF_3$ | |
| 10-13 | Cl | $CF_3$ | Me | Me | |
| 10-14 | Cl | $CF_3$ | Me | Et | |
| 10-15 | Cl | $CF_3$ | Me | $CH_2$—c-Pr | |
| 10-16 | Cl | $CF_3$ | Me | $CH_2$—$CF_3$ | |
| 10-17 | Br | $SO_2Me$ | Me | Me | |
| 10-18 | Br | $SO_2Me$ | Me | Et | |
| 10-19 | Br | $SO_2Me$ | Me | $CH_2$—c-Pr | |
| 10-20 | Br | $SO_2Me$ | Me | $CH_2$—$CF_3$ | |
| 10-21 | Br | $CF_3$ | Me | Me | |
| 10-22 | Br | $CF_3$ | Me | Et | |
| 10-23 | Br | $CF_3$ | Me | $CH_2$—c-Pr | |
| 10-24 | Br | $CF_3$ | Me | $CH_2$—$CF_3$ | |
| 10-25 | Me | $SO_2Me$ | Me | Me | |
| 10-26 | Me | $SO_2Me$ | Me | Et | |
| 10-27 | Me | $SO_2Me$ | Me | $CH_2$—c-Pr | |
| 10-28 | Me | $SO_2Me$ | Me | $CH_2$—$CF_3$ | |
| 10-29 | Me | $CF_3$ | Me | Me | |
| 10-30 | Me | $CF_3$ | Me | Et | |
| 10-31 | Me | $CF_3$ | Me | $CH_2$—c-Pr | |
| 10-32 | Me | $CF_3$ | Me | $CH_2$—$CF_3$ | |

TABLE 10-continued

Inventive compounds of the general formula (I) in which Q is Q1, $R^x$ is a propyl group, and R and W are each hydrogen (Z isomer, or E isomer)

| No. | X | Y | $R^{1'}$ | $R^{2'}$ | Physical data ($^1$H NMR) |
|---|---|---|---|---|---|
| 10-33 | OMe | $CF_3$ | Me | Me | |
| 10-34 | OMe | $CF_3$ | Me | Et | |
| 10-35 | OMe | $CF_3$ | Me | $CH_2$—c-Pr | |
| 10-36 | OMe | $CF_3$ | Me | $CH_2$—$CF_3$ | |
| 10-37 | OMe | $CHF_2$ | Me | Me | |
| 10-38 | OMe | $CHF_2$ | Me | Et | |
| 10-39 | OMe | $CHF_2$ | Me | $CH_2$—c-Pr | |
| 10-40 | OMe | $CHF_2$ | Me | $CH_2$—$CF_3$ | |
| 10-41 | $SO_2Me$ | $CF_3$ | Me | Me | |
| 10-42 | $SO_2Me$ | $CF_3$ | Me | Et | |
| 10-43 | $SO_2Me$ | $CF_3$ | Me | $CH_2$—c-Pr | |
| 10-44 | $SO_2Me$ | $CF_3$ | Me | $CH_2$—$CF_3$ | |
| 10-45 | Me | $SO_2Me$ | Me | i-Bu | |

TABLE 11

Inventive compounds of the general formula (I) in which Q is Q2, $R^x$ is a methyl group, and R and W are each hydrogen (Z isomer, or E isomer)

| No. | X | Y | $R^{1'}$ | $R^{2'}$ | Physical data ($^1$H NMR) |
|---|---|---|---|---|---|
| 11-1 | Cl | Cl | Me | Me | |
| 11-2 | Cl | Cl | Me | Et | |
| 11-3 | Cl | Cl | Me | $CH_2$—c-Pr | |
| 11-4 | Cl | Cl | Me | $CH_2$—$CF_3$ | |
| 11-5 | Cl | $SO_2Me$ | Me | Me | * |
| 11-6 | Cl | $SO_2Me$ | Me | Et | |
| 11-7 | Cl | $SO_2Me$ | Me | $CH_2$—c-Pr | |
| 11-8 | Cl | $SO_2Me$ | Me | $CH_2$—$CF_3$ | |
| 11-9 | Cl | Me | Me | Me | |
| 11-10 | Cl | Me | Me | Et | |
| 11-11 | Cl | Me | Me | $CH_2$—c-Pr | |
| 11-12 | Cl | Me | Me | $CH_2$—$CF_3$ | |
| 11-13 | Cl | $CF_3$ | Me | Me | |
| 11-14 | Cl | $CF_3$ | Me | Et | |
| 11-15 | Cl | $CF_3$ | Me | $CH_2$—c-Pr | |
| 11-16 | Cl | $CF_3$ | Me | $CH_2$—$CF_3$ | |
| 11-17 | Br | $SO_2Me$ | Me | Me | |
| 11-18 | Br | $SO_2Me$ | Me | Et | |
| 11-19 | Br | $SO_2Me$ | Me | $CH_2$—c-Pr | |
| 11-20 | Br | $SO_2Me$ | Me | $CH_2$—$CF_3$ | |
| 11-21 | Br | $CF_3$ | Me | Me | |
| 11-22 | Br | $CF_3$ | Me | Et | |
| 11-23 | Br | $CF_3$ | Me | $CH_2$—c-Pr | |
| 11-24 | Br | $CF_3$ | Me | $CH_2$—$CF_3$ | |
| 11-25 | Me | $SO_2Me$ | Me | Me | |
| 11-26 | Me | $SO_2Me$ | Me | Et | |
| 11-27 | Me | $SO_2Me$ | Me | $CH_2$—c-Pr | |
| 11-28 | Me | $SO_2Me$ | Me | $CH_2$—$CF_3$ | |
| 11-29 | Me | $CF_3$ | Me | Me | |

TABLE 11-continued

Inventive compounds of the general formula (I) in which Q is Q2, R$^x$ is a methyl group, and R and W are each hydrogen (Z isomer, or E isomer)

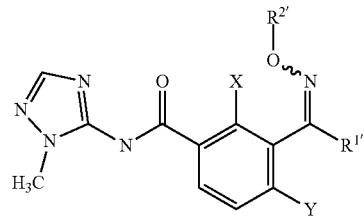

| No. | X | Y | R$^{1'}$ | R$^{2'}$ | Physical data ($^1$H NMR) |
|---|---|---|---|---|---|
| 11-30 | Me | CF$_3$ | Me | Et | |
| 11-31 | Me | CF$_3$ | Me | CH$_2$—c-Pr | |
| 11-32 | Me | CF$_3$ | Me | CH$_2$—CF$_3$ | |
| 11-33 | OMe | CF$_3$ | Me | Me | |
| 11-34 | OMe | CF$_3$ | Me | Et | |
| 11-35 | OMe | CF$_3$ | Me | CH$_2$—c-Pr | |
| 11-36 | OMe | CF$_3$ | Me | CH$_2$—CF$_3$ | |
| 11-37 | OMe | CHF$_2$ | Me | Me | |
| 11-38 | OMe | CHF$_2$ | Me | Et | |
| 11-39 | OMe | CHF$_2$ | Me | CH$_2$—c-Pr | |
| 11-40 | OMe | CHF$_2$ | Me | CH$_2$—CF$_3$ | |
| 11-41 | SO$_2$Me | CF$_3$ | Me | Me | |
| 11-42 | SO$_2$Me | CF$_3$ | Me | Et | |
| 11-43 | SO$_2$Me | CF$_3$ | Me | CH$_2$—c-Pr | |
| 11-44 | SO$_2$Me | CF$_3$ | Me | CH$_2$—CF$_3$ | |
| 11-45 | Me | SO$_2$Me | Me | i-Bu | |

TABLE 12

Inventive compounds of the general formula (I) in which Q is Q3, R$^y$ is chlorine, and R and W are each hydrogen (Z isomer, or E isomer)

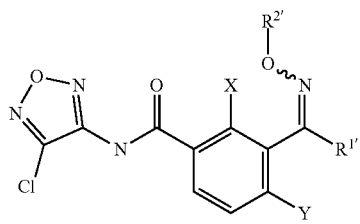

| No. | X | Y | R$^{1'}$ | R$^{2'}$ | Physical data ($^1$H NMR) |
|---|---|---|---|---|---|
| 12-1 | Cl | Cl | Me | Me | |
| 12-2 | Cl | Cl | Me | Et | |
| 12-3 | Cl | Cl | Me | CH$_2$—c-Pr | |
| 12-4 | Cl | Cl | Me | CH$_2$—CF$_3$ | |
| 12-5 | Cl | SO$_2$Me | Me | Me | |
| 12-6 | Cl | SO$_2$Me | Me | Et | |
| 12-7 | Cl | SO$_2$Me | Me | CH$_2$—c-Pr | |
| 12-8 | Cl | SO$_2$Me | Me | CH$_2$—CF$_3$ | |
| 12-9 | Cl | Me | Me | Me | |
| 12-10 | Cl | Me | Me | Et | |
| 12-11 | Cl | Me | Me | CH$_2$—c-Pr | |
| 12-12 | Cl | Me | Me | CH$_2$—CF$_3$ | |
| 12-13 | Cl | CF$_3$ | Me | Me | |
| 12-14 | Cl | CF$_3$ | Me | Et | |
| 12-15 | Cl | CF$_3$ | Me | CH$_2$—c-Pr | |
| 12-16 | Cl | CF$_3$ | Me | CH$_2$—CF$_3$ | |
| 12-17 | Br | SO$_2$Me | Me | Me | |
| 12-18 | Br | SO$_2$Me | Me | Et | |
| 12-19 | Br | SO$_2$Me | Me | CH$_2$—c-Pr | |
| 12-20 | Br | SO$_2$Me | Me | CH$_2$—CF$_3$ | |
| 12-21 | Br | CF$_3$ | Me | Me | |
| 12-22 | Br | CF$_3$ | Me | Et | |
| 12-23 | Br | CF$_3$ | Me | CH$_2$—c-Pr | |
| 12-24 | Br | CF$_3$ | Me | CH$_2$—CF$_3$ | |
| 12-25 | Me | SO$_2$Me | Me | Me | * |
| 12-26 | Me | SO$_2$Me | Me | Et | * |

TABLE 12-continued

Inventive compounds of the general formula (I) in which Q is Q3, R$^y$ is chlorine, and R and W are each hydrogen (Z isomer, or E isomer)

| No. | X | Y | R$^{1'}$ | R$^{2'}$ | Physical data ($^1$H NMR) |
|---|---|---|---|---|---|
| 12-27 | Me | SO$_2$Me | Me | CH$_2$—c-Pr | |
| 12-28 | Me | SO$_2$Me | Me | CH$_2$—CF$_3$ | |
| 12-29 | Me | CF$_3$ | Me | Me | |
| 12-30 | Me | CF$_3$ | Me | Et | |
| 12-31 | Me | CF$_3$ | Me | CH$_2$—c-Pr | |
| 12-32 | Me | CF$_3$ | Me | CH$_2$—CF$_3$ | |
| 12-33 | OMe | CF$_3$ | Me | Me | |
| 12-34 | OMe | CF$_3$ | Me | Et | |
| 12-35 | OMe | CF$_3$ | Me | CH$_2$—c-Pr | |
| 12-36 | OMe | CF$_3$ | Me | CH$_2$—CF$_3$ | |
| 12-37 | OMe | CHF$_2$ | Me | Me | |
| 12-38 | OMe | CHF$_2$ | Me | Et | |
| 12-39 | OMe | CHF$_2$ | Me | CH$_2$—c-Pr | |
| 12-40 | OMe | CHF$_2$ | Me | CH$_2$—CF$_3$ | |
| 12-41 | SO$_2$Me | CF$_3$ | Me | Me | |
| 12-42 | SO$_2$Me | CF$_3$ | Me | Et | |
| 12-43 | SO$_2$Me | CF$_3$ | Me | CH$_2$—c-Pr | |
| 12-44 | SO$_2$Me | CF$_3$ | Me | CH$_2$—CF$_3$ | |
| 12-45 | Me | SO$_2$Me | Me | i-Bu | |

TABLE 13

Inventive compounds of the general formula (I) in which Q is Q3, R$^y$ is methyl, and R and W are each hydrogen (Z isomer, or E isomer)

| No. | X | Y | R$^{1'}$ | R$^{2'}$ | Physical data ($^1$H NMR) |
|---|---|---|---|---|---|
| 13-1 | Cl | Cl | Me | Me | |
| 13-2 | Cl | Cl | Me | Et | |
| 13-3 | Cl | Cl | Me | CH$_2$—c-Pr | |
| 13-4 | Cl | Cl | Me | CH$_2$—CF$_3$ | |
| 13-5 | Cl | SO$_2$Me | Me | Me | * |
| 13-6 | Cl | SO$_2$Me | Me | Et | |
| 13-7 | Cl | SO$_2$Me | Me | CH$_2$—c-Pr | |
| 13-8 | Cl | SO$_2$Me | Me | CH$_2$—CF$_3$ | |
| 13-9 | Cl | Me | Me | Me | |
| 13-10 | Cl | Me | Me | Et | |
| 13-11 | Cl | Me | Me | CH$_2$—c-Pr | |
| 13-12 | Cl | Me | Me | CH$_2$—CF$_3$ | |
| 13-13 | Cl | CF$_3$ | Me | Me | |
| 13-14 | Cl | CF$_3$ | Me | Et | |
| 13-15 | Cl | CF$_3$ | Me | CH$_2$—c-Pr | |
| 13-16 | Cl | CF$_3$ | Me | CH$_2$—CF$_3$ | |
| 13-17 | Br | SO$_2$Me | Me | Me | |
| 13-18 | Br | SO$_2$Me | Me | Et | |
| 13-19 | Br | SO$_2$Me | Me | CH$_2$—c-Pr | |
| 13-20 | Br | SO$_2$Me | Me | CH$_2$—CF$_3$ | |
| 13-21 | Br | CF$_3$ | Me | Me | |
| 13-22 | Br | CF$_3$ | Me | Et | |
| 13-23 | Br | CF$_3$ | Me | CH$_2$—c-Pr | |

TABLE 13-continued

Inventive compounds of the general formula (I) in which Q is Q3, R$^y$ is methyl, and R and W are each hydrogen (Z isomer, or E isomer)

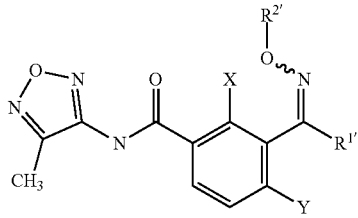

| No. | X | Y | R$^{1'}$ | R$^{2'}$ | Physical data ($^1$H NMR) |
|---|---|---|---|---|---|
| 13-24 | Br | CF$_3$ | Me | CH$_2$—CF$_3$ | |
| 13-25 | Me | SO$_2$Me | Me | Me | * |
| 13-26 | Me | SO$_2$Me | Me | Et | * |
| 13-27 | Me | SO$_2$Me | Me | CH$_2$—c-Pr | |
| 13-28 | Me | SO$_2$Me | Me | CH$_2$—CF$_3$ | |
| 13-29 | Me | CF$_3$ | Me | Me | |
| 13-30 | Me | CF$_3$ | Me | Et | |
| 13-31 | Me | CF$_3$ | Me | CH$_2$—c-Pr | |
| 13-32 | Me | CF$_3$ | Me | CH$_2$—CF$_3$ | |
| 13-33 | OMe | CF$_3$ | Me | Me | |
| 13-34 | OMe | CF$_3$ | Me | Et | |
| 13-35 | OMe | CF$_3$ | Me | CH$_2$—c-Pr | |
| 13-36 | OMe | CF$_3$ | Me | CH$_2$—CF$_3$ | |
| 13-37 | OMe | CHF$_2$ | Me | Me | |
| 13-38 | OMe | CHF$_2$ | Me | Et | |
| 13-39 | OMe | CHF$_2$ | Me | CH$_2$—c-Pr | |
| 13-40 | OMe | CHF$_2$ | Me | CH$_2$—CF$_3$ | |
| 13-41 | SO$_2$Me | CF$_3$ | Me | Me | |
| 13-42 | SO$_2$Me | CF$_3$ | Me | Et | |
| 13-43 | SO$_2$Me | CF$_3$ | Me | CH$_2$—c-Pr | |
| 13-44 | SO$_2$Me | CF$_3$ | Me | CH$_2$—CF$_3$ | |
| 13-45 | Me | SO$_2$Me | Me | i-Bu | |

TABLE 14

Inventive compounds of the general formula (I) in which Q is Q4, R$^z$ is methyl, and R and W are each hydrogen (Z isomer, or E isomer)

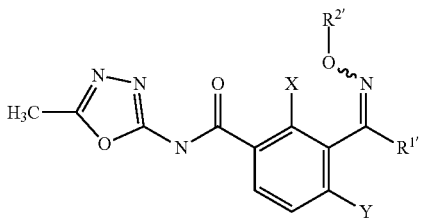

| No. | X | Y | R$^{1'}$ | R$^{2'}$ | Physical data ($^1$H NMR) |
|---|---|---|---|---|---|
| 14-1 | Cl | Cl | Me | Me | |
| 14-2 | Cl | Cl | Me | Et | |
| 14-3 | Cl | Cl | Me | CH$_2$—c-Pr | |
| 14-4 | Cl | Cl | Me | CH$_2$—CF$_3$ | |
| 14-5 | Cl | SO$_2$Me | Me | Me | * |
| 14-6 | Cl | SO$_2$Me | Me | Et | |
| 14-7 | Cl | SO$_2$Me | Me | CH$_2$—c-Pr | |
| 14-8 | Cl | SO$_2$Me | Me | CH$_2$—CF$_3$ | |
| 14-9 | Cl | Me | Me | Me | |
| 14-10 | Cl | Me | Me | Et | |
| 14-11 | Cl | Me | Me | CH$_2$—c-Pr | |
| 14-12 | Cl | Me | Me | CH$_2$—CF$_3$ | |
| 14-13 | Cl | CF$_3$ | Me | Me | |
| 14-14 | Cl | CF$_3$ | Me | Et | |
| 14-15 | Cl | CF$_3$ | Me | CH$_2$—c-Pr | |
| 14-16 | Cl | CF$_3$ | Me | CH$_2$—CF$_3$ | |
| 14-17 | Br | SO$_2$Me | Me | Me | |
| 14-18 | Br | SO$_2$Me | Me | Et | |
| 14-19 | Br | SO$_2$Me | Me | CH$_2$—c-Pr | |
| 14-20 | Br | SO$_2$Me | Me | CH$_2$—CF$_3$ | |

TABLE 14-continued

Inventive compounds of the general formula (I) in which Q is Q4, R$^z$ is methyl, and R and W are each hydrogen (Z isomer, or E isomer)

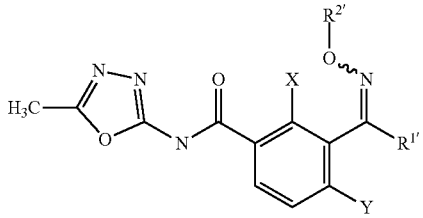

| No. | X | Y | R$^{1'}$ | R$^{2'}$ | Physical data ($^1$H NMR) |
|---|---|---|---|---|---|
| 14-21 | Br | CF$_3$ | Me | Me | |
| 14-22 | Br | CF$_3$ | Me | Et | |
| 14-23 | Br | CF$_3$ | Me | CH$_2$—c-Pr | |
| 14-24 | Br | CF$_3$ | Me | CH$_2$—CF$_3$ | |
| 14-25 | Me | SO$_2$Me | Me | Me | |
| 14-26 | Me | SO$_2$Me | Me | Et | |
| 14-27 | Me | SO$_2$Me | Me | CH$_2$—c-Pr | |
| 14-28 | Me | SO$_2$Me | Me | CH$_2$—CF$_3$ | |
| 14-29 | Me | CF$_3$ | Me | Me | |
| 14-30 | Me | CF$_3$ | Me | Et | |
| 14-31 | Me | CF$_3$ | Me | CH$_2$—c-Pr | |
| 14-32 | Me | CF$_3$ | Me | CH$_2$—CF$_3$ | |
| 14-33 | OMe | CF$_3$ | Me | Me | |
| 14-34 | OMe | CF$_3$ | Me | Et | |
| 14-35 | OMe | CF$_3$ | Me | CH$_2$—c-Pr | |
| 14-36 | OMe | CF$_3$ | Me | CH$_2$—CF$_3$ | |
| 14-37 | OMe | CHF$_2$ | Me | Me | |
| 14-38 | OMe | CHF$_2$ | Me | Et | |
| 14-39 | OMe | CHF$_2$ | Me | CH$_2$—c-Pr | |
| 14-40 | OMe | CHF$_2$ | Me | CH$_2$—CF$_3$ | |
| 14-41 | SO$_2$Me | CF$_3$ | Me | Me | |
| 14-42 | SO$_2$Me | CF$_3$ | Me | Et | |
| 14-43 | SO$_2$Me | CF$_3$ | Me | CH$_2$—c-Pr | |
| 14-44 | SO$_2$Me | CF$_3$ | Me | CH$_2$—CF$_3$ | |
| 14-45 | Me | SO$_2$Me | Me | i-Bu | |

The abbreviations used mean:
Et=ethyl  Me=methyl  n-Pr=n-propyl  i-Pr=isopropyl  c-Pr=cyclopropyl  Ph=phenyl  Bn=benzyl  Bu=butyl  c=cyclo NMR data for selected examples reported by the NMR peak list method The $^1$H NMR data for selected examples are noted in the form of 1H NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:
δ$_1$ (intensity$_1$); δ$_2$ (intensity$_2$); . . . ; δ$_i$ (intensity$_i$); . . . ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra was accomplished using tetramethylsilane and/or the chemical shift of the solvent, particularly in the case of spectra which are measured in DMSO. Therefore, the tetramethylsilane peak may occur in NMR peak lists.

The lists of the $^1$H NMR peaks are similar to the conventional $^1$H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Example 1-5

$^1$H-NMR (400.0 MHz, $d_6$-DMSO): δ=11.861 (0.6); 7.818 (0.7); 7.797 (1.2); 7.740 (2.1); 7.720 (1.3); 4.185 (1.0); 4.168 (3.2); 4.150 (3.2); 4.133 (1.0); 3.997 (16.0); 3.310 (13.3); 2.510 (4.5); 2.505 (9.7); 2.501 (13.4); 2.496 (9.3); 2.491 (4.2); 2.113 (11.1); 2.072 (15.1); 1.267 (3.6); 1.250 (8.1); 1.232 (3.5)

Example 1-8

$^1$H-NMR (400.0 MHz, $d_6$-DMSO): δ=11.859 (0.8); 7.816 (0.7); 7.795 (1.2); 7.739 (2.1); 7.718 (1.3); 3.996 (16.0); 3.969 (2.0); 3.951 (2.0); 3.310 (30.4); 2.518 (0.6); 2.510 (7.4); 2.505 (15.7); 2.500 (21.7); 2.496 (15.2); 2.491 (6.8); 2.130 (10.7); 1.145 (0.6); 0.533 (1.4); 0.528 (1.5); 0.523 (0.6); 0.518 (0.7); 0.512 (1.5); 0.508 (1.3); 0.498 (0.6); 0.308 (0.6); 0.297 (1.6); 0.293 (1.6); 0.285 (1.4); 0.281 (1.7)

Example 1-9

$^1$H-NMR (400.0 MHz, $d_6$-DMSO): δ=11.881 (0.8); 7.856 (0.7); 7.835 (1.2); 7.768 (2.0); 7.747 (1.3); 5.751 (1.0); 4.840 (0.6); 4.817 (2.0); 4.794 (2.1); 4.772 (0.7); 3.996 (16.0); 3.310 (39.5); 2.523 (0.6); 2.518 (0.9); 2.510 (10.8); 2.505 (23.1); 2.500 (31.9); 2.496 (22.3); 2.491 (10.0); 2.192 (10.9); 2.072 (1.2)

Example 1-15

$^1$H-NMR (400.0 MHz, CDCl$_3$): δ=8.163 (2.1); 8.142 (2.5); 7.873 (1.9); 7.852 (1.6); 7.261 (38.1); 4.141 (12.7); 3.823 (15.7); 3.100 (16.0); 2.340 (13.5); 1.285 (0.5); 0.000 (14.4)

Example 1-22

$^1$H-NMR (400.0 MHz, $d_6$-DMSO): δ=12.009 (1.1); 8.125 (0.6); 8.105 (1.4); 8.079 (0.7); 5.751 (9.1); 4.017 (16.0); 3.970 (2.3); 3.953 (2.4); 3.346 (16.1); 2.518 (0.6); 2.510 (7.7); 2.505 (16.6); 2.500 (22.9); 2.496 (16.0); 2.491 (7.2); 2.164 (6.2); 1.146 (0.6); 0.542 (1.3); 0.538 (1.5); 0.530 (0.7); 0.528 (0.5); 0.522 (1.4); 0.518 (1.3); 0.302 (0.6); 0.291 (1.3); 0.287 (1.1); 0.279 (1.4); 0.275 (0.9); 0.000 (1.1)

Example 1-67

$^1$H-NMR (400.0 MHz, CDCl$_3$): δ=8.096 (1.0); 8.075 (1.4); 7.939 (1.5); 7.918 (1.2); 7.260 (38.5); 4.126 (9.5); 3.965 (16.0); 3.219 (14.2); 2.472 (8.7); 2.221 (14.5); 00.000 (14.8)

Example 1-71

$^1$H-NMR (400.0 MHz, CDCl$_3$): δ=8.081 (1.2); 8.061 (1.6); 7.937 (1.8); 7.917 (1.4); 7.261 (32.7); 4.220 (1.3); 4.202 (4.1); 4.185 (4.2); 4.167 (1.3); 4.123 (11.9); 3.204 (15.7); 2.466 (9.9); 2.221 (16.0); 1.337 (4.6); 1.319 (10.1); 1.302 (4.5); 0.000 (12.9)

Example 1-74

$^1$H-NMR (400.0 MHz, $d_6$-DMSO): δ=7.987 (0.9); 7.967 (1.6); 7.918 (1.3); 7.898 (0.7); 5.753 (7.7); 4.010 (16.0); 3.956 (1.7); 3.951 (1.7); 3.938 (1.8); 3.934 (1.7); 3.311 (15.0); 3.275 (10.5); 3.247 (1.2); 2.518 (0.6); 2.510 (7.3); 2.505 (15.7); 2.500 (21.7); 2.496 (15.1); 2.491 (6.8); 2.375 (1.0); 2.331 (8.0); 2.146 (11.6); 2.116 (1.4); 1.144 (0.6); 0.536 (1.3); 0.531 (1.5); 0.520 (0.6); 0.516 (1.5); 0.511 (1.4); 0.294 (0.6); 0.287 (0.8); 0.283 (1.3); 0.278 (1.2); 0.271 (1.5); 0.266 (0.9); 0.260 (0.6); 0.000 (5.0)

Example 2-1

$^1$H-NMR (400.0 MHz, $d_6$-DMSO): δ=11.765 (1.4); 7.815 (0.8); 7.795 (1.4); 7.744 (2.5); 7.723 (1.4); 4.384 (1.0); 4.366 (3.3); 4.347 (3.3); 4.329 (1.1); 3.907 (16.0); 3.889 (0.6); 3.313 (26.3); 2.523 (0.7); 2.510 (9.4); 2.505 (19.9); 2.501 (27.5); 2.496 (19.6); 2.492 (9.1); 2.112 (12.7); 2.083 (0.6); 1.484 (3.7); 1.466 (8.3); 1.447 (3.7); 0.000 (0.5)

Example 2-15

$^1$H-NMR (400.0 MHz, CDCl$_3$): δ=8.169 (1.9); 8.149 (2.2); 7.899 (1.4); 7.878 (1.2); 7.263 (38.0); 4.533 (0.6); 4.515 (2.0); 4.497 (2.1); 4.479 (0.7); 3.986 (16.0); 3.270 (14.2); 2.262 (11.9); 1.646 (3.2); 1.628 (7.3); 1.610 (3.1); 0.000 (14.7)

Example 2-19

$^1$H-NMR (400.0 MHz, CDCl$_3$): δ=8.160 (2.1); 8.140 (2.5); 7.892 (1.6); 7.872 (1.4); 7.263 (34.8); 4.532 (0.7); 4.514 (2.2); 4.496 (2.3); 4.478 (0.8); 4.241 (1.0); 4.223 (3.0); 4.206 (3.3); 4.188 (1.1); 3.256 (16.0); 2.261 (13.6); 1.645 (3.6); 1.627 (8.2); 1.609 (3.5); 1.347 (4.8); 1.330 (10.3); 1.312 (4.6); 0.000 (13.1)

Example 2-22

$^1$H-NMR (400.0 MHz, $d_6$-DMSO): δ=11.913 (4.1); 8.126 (1.6); 8.105 (3.5); 8.075 (1.6); 8.054 (0.8); 5.752 (9.0); 4.402 (2.0); 4.384 (6.4); 4.366 (6.5); 4.348 (2.1); 3.972 (4.6); 3.969 (4.6); 3.954 (4.9); 3.952 (4.6); 3.394 (0.7); 3.345 (63.8); 2.669 (0.6); 2.550 (0.8); 2.545 (0.7); 2.540 (0.6); 2.523 (2.1); 2.518 (3.2); 2.509 (34.2); 2.505 (71.6); 2.500 (98.2); 2.496 (68.7); 2.491 (31.0); 2.327 (0.7); 2.165 (14.5); 1.492 (7.1); 1.474 (16.0); 1.456 (7.0); 1.166 (0.8); 1.163 (0.8); 1.158 (0.8); 1.154 (0.6); 1.146 (1.4); 1.137

(0.6); 1.133 (0.8); 1.128 (0.8); 1.126 (0.9); 0.552 (0.8); 0.543 (3.1); 0.539 (3.5); 0.531 (1.7); 0.528 (1.3); 0.523 (3.3); 0.519 (3.1); 0.510 (0.9); 0.302 (1.4); 0.291 (3.3); 0.279 (3.3); 0.275 (2.2); 0.267 (1.0); 0.000 (4.6)

Example 2-67

$^1$H-NMR (400.0 MHz, CDCl$_3$): δ=8.092 (1.0); 8.071 (1.3); 7.925 (1.4); 7.904 (1.1); 7.260 (43.7); 5.299 (10.0); 4.488 (10.2); 4.484 (1.3); 4.470 (1.2); 4.466 (1.3); 3.964 (16.0); 3.218 (14.4); 2.472 (8.9); 2.221 (14.6); 2.004 (0.9); 1.651 (2.9); 1.633 (6.3); 1.615 (2.8); 0.000 (17.1)

Example 2-71

$^1$H-NMR (400.0 MHz, CDCl$_3$): δ=8.085 (1.2); 8.065 (1.5); 7.908 (1.2); 7.888 (1.0); 7.261 (59.3); 4.510 (0.5); 4.507 (0.5); 4.492 (1.5); 4.489 (1.5); 4.473 (1.6); 4.470 (1.6); 4.455 (0.6); 4.452 (0.5); 4.222 (1.3); 4.204 (4.3); 4.187 (4.3); 4.169 (1.4); 3.206 (15.7); 2.466 (9.0); 2.224 (16.0); 1.655 (3.3); 1.636 (7.4); 1.618 (3.2); 1.339 (4.7); 1.321 (10.2); 1.303 (4.6); 0.008 (0.6); 0.000 (21.8); −0.009 (0.6)

Example 2-74

$^1$H-NMR (400.0 MHz, d$_6$-DMSO): δ=11.689 (1.7); 7.990 (1.2); 7.970 (2.1); 7.911 (1.5); 7.890 (0.9); 5.753 (8.2); 4.385 (1.1); 4.367 (3.7); 4.349 (3.8); 4.330 (1.2); 3.956 (2.2); 3.951 (2.3); 3.938 (2.3); 3.934 (2.2); 3.311 (33.8); 3.274 (14.3); 2.523 (0.7); 2.518 (1.0); 2.510 (11.8); 2.505 (25.4); 2.500 (35.2); 2.496 (24.4); 2.491 (10.8); 2.328 (10.9); 2.147 (16.0); 1.493 (4.6); 1.475 (10.9); 1.456 (4.6); 1.144 (0.8); 0.537 (1.8); 0.532 (2.0); 0.528 (0.8); 0.521 (0.7); 0.516 (1.9); 0.512 (1.8); 0.507 (0.5); 0.293 (0.8); 0.287 (1.0); 0.283 (1.7); 0.278 (1.5); 0.274 (1.2); 0.271 (1.9); 0.266 (1.2); 0.260 (0.7); 0.000 (7.5)

Example 2-136

$^1$H-NMR (400.0 MHz, d$_6$-DMSO): δ=11.682 (2.9); 8.312 (3.3); 7.990 (1.4); 7.970 (2.3); 7.910 (1.7); 7.890 (1.0); 4.384 (1.2); 4.366 (3.7); 4.348 (3.7); 4.330 (1.2); 3.902 (2.6); 3.898 (2.8); 3.884 (2.8); 3.881 (2.7); 3.335 (18.2); 3.255 (14.1); 2.523 (1.0); 2.509 (18.0); 2.505 (37.3); 2.500 (51.0); 2.496 (36.9); 2.492 (17.5); 2.319 (11.8); 2.145 (15.1); 1.974 (0.9); 1.957 (1.1); 1.940 (0.9); 1.493 (4.3); 1.475 (9.4); 1.457 (4.2); 0.933 (16.0); 0.917 (15.5); 0.008 (0.6); 0.000 (17.6); −0.009 (0.7)

Example 3-1

$^1$H-NMR (400.0 MHz, d$_6$-DMSO): δ=11.750 (1.2); 7.802 (0.7); 7.781 (1.5); 7.744 (2.7); 7.723 (1.3); 5.752 (4.2); 4.323 (1.6); 4.305 (2.4); 4.287 (1.7); 3.907 (16.0); 3.309 (31.3); 2.523 (0.5); 2.518 (0.7); 2.510 (9.7); 2.505 (20.8); 2.500 (28.9); 2.496 (20.2); 2.491 (9.1); 2.113 (12.6); 2.072 (0.8); 1.907 (1.0); 1.888 (1.7); 1.870 (1.7); 1.852 (1.0); 0.895 (3.5); 0.877 (7.7); 0.858 (3.3); 0.000 (0.6)

Example 3-5

$^1$H-NMR (400.0 MHz, d$_6$-DMSO): δ=11.747 (1.3); 7.797 (0.9); 7.776 (1.9); 7.740 (3.5); 7.719 (1.7); 5.751 (1.0); 4.322 (2.1); 4.305 (3.0); 4.287 (2.1); 4.186 (1.4); 4.168 (4.7); 4.151 (4.7); 4.133 (1.5); 3.310 (36.8); 2.523 (0.5); 2.518 (0.8); 2.510 (9.7); 2.505 (20.9); 2.501 (29.0); 2.496 (20.2); 2.491 (9.0); 2.114 (16.0); 2.072 (7.7); 1.907 (1.2); 1.889 (2.2); 1.871 (2.2); 1.853 (1.3); 1.267 (5.3); 1.250 (11.9); 1.232 (5.1); 0.895 (4.5); 0.876 (9.9); 0.858 (4.2); 0.000 (1.8)

Example 3-8

$^1$H-NMR (400.0 MHz, d$_6$-DMSO): δ=11.746 (1.7); 7.795 (1.0); 7.774 (2.1); 7.738 (3.6); 7.717 (1.7); 5.752 (0.5); 4.321 (2.2); 4.303 (3.3); 4.285 (2.2); 3.969 (4.2); 3.951 (4.2); 3.308 (81.7); 2.523 (1.8); 2.518 (2.7); 2.510 (27.3); 2.505 (56.6); 2.500 (77.1); 2.496 (53.8); 2.491 (24.1); 2.131 (16.0); 2.072 (0.7); 1.905 (1.3); 1.887 (2.4); 1.869 (2.4); 1.851 (1.3); 1.164 (0.6); 1.161 (0.6); 1.156 (0.5); 1.144 (1.0); 1.131 (0.5); 1.123 (0.5); 0.894 (4.7); 0.875 (10.0); 0.857 (4.4); 0.544 (0.8); 0.533 (2.2); 0.529 (2.3); 0.524 (1.0); 0.518 (1.1); 0.513 (2.4); 0.508 (2.0); 0.498 (0.9); 0.308 (0.9); 0.297 (2.5); 0.294 (2.4); 0.286 (2.2); 0.282 (2.6); 0.271 (0.6); 0.000 (1.7)

Example 3-9

$^1$H-NMR (400.0 MHz, d$_6$-DMSO): δ=11.767 (1.4); 7.836 (1.0); 7.815 (1.8); 7.768 (3.3); 7.747 (1.8); 5.751 (1.4); 4.840 (0.9); 4.818 (2.9); 4.795 (3.0); 4.773 (1.0); 4.321 (2.2); 4.304 (3.2); 4.285 (2.2); 3.309 (62.7); 3.257 (0.6); 2.523 (1.4); 2.518 (2.0); 2.510 (19.5); 2.505 (40.5); 2.500 (55.3); 2.496 (38.3); 2.491 (16.8); 2.194 (16.0); 2.072 (2.5); 1.906 (1.3); 1.888 (2.3); 1.870 (2.4); 1.852 (1.3); 0.894 (4.7); 0.876 (10.1); 0.857 (4.3); 0.000 (1.1)

Example 3-15

$^1$H-NMR (400.0 MHz, CDCl$_3$): δ=8.150 (2.0); 8.130 (2.3); 7.852 (2.0); 7.832 (1.8); 7.261 (29.5); 4.452 (1.4); 4.434 (2.2); 4.415 (1.4); 3.820 (16.0); 3.097 (15.7); 2.337 (13.9); 2.065 (1.1); 2.047 (2.1); 2.028 (2.1); 2.010 (1.2); 1.285 (0.9); 1.256 (0.7); 1.020 (1.0); 1.012 (3.8); 1.003 (1.2); 0.994 (7.7); 0.975 (3.6); 0.000 (11.0)

Example 3-19

$^1$H-NMR (400.0 MHz, CDCl$_3$): δ=8.173 (1.0); 8.153 (1.2); 7.888 (1.9); 7.867 (1.7); 7.519 (0.7); 7.260 (134.4); 6.996 (0.7); 4.444 (0.7); 4.425 (1.1); 4.406 (0.7); 4.244 (1.0); 4.227 (3.1); 4.209 (3.3); 4.209 (3.3); 4.192 (1.1); 3.249 (16.0); 2.265 (15.0); 2.060 (0.9); 2.041 (1.5); 2.023 (1.5); 2.004 (0.9); 1.350 (4.8); 1.333 (10.6); 1.315 (4.6); 1.285 (0.7); 1.011 (3.6); 0.992 (7.8); 0.974 (3.4); 0.008 (1.5); 0.000 (51.6); −0.009 (1.4)

Example 3-22

$^1$H-NMR (400.0 MHz, d$_6$-DMSO): δ=11.898 (3.0); 8.127 (1.7); 8.107 (3.1); 8.063 (1.3); 8.043 (0.7); 5.752 (16.0); 4.340 (3.1); 4.322 (4.6); 4.304 (3.1); 3.973 (3.4); 3.968 (3.5); 3.955 (3.6); 3.951 (3.3); 3.345 (22.9); 3.318 (47.5); 2.669 (0.7); 2.523 (2.0); 2.518 (2.9); 2.509 (38.3); 2.505 (82.3); 2.500 (114.3); 2.496 (79.8); 2.491 (35.7); 2.332 (0.5); 2.327 (0.8); 2.322 (0.5); 2.165 (12.9); 1.914 (1.8); 1.896 (3.2); 1.878 (3.2); 1.860 (1.8); 1.165 (0.7); 1.163 (0.7); 1.157 (0.7); 1.154 (0.5); 1.145 (1.3); 1.137 (0.5); 1.133 (0.7); 1.128 (0.7); 1.125 (0.8); 0.902 (6.7); 0.883 (14.6); 0.865 (6.3); 0.551 (0.7); 0.543 (2.6); 0.539 (3.1); 0.531 (1.5); 0.528 (1.1); 0.523 (2.8); 0.518 (2.7); 0.510

(0.8); 0.508 (0.8); 0.302 (1.1); 0.291 (2.8); 0.287 (2.3); 0.279 (2.9); 0.275 (1.8); 0.267 (0.9); 0.000 (11.5)

Example 4-1

$^1$H-NMR (400.0 MHz, d$_6$-DMSO): δ=11.294 (0.8); 7.741 (0.6); 7.708 (0.8); 3.903 (16.0); 3.764 (8.6); 3.309 (26.7); 2.523 (0.5); 2.518 (0.8); 2.509 (9.9); 2.505 (21.1); 2.500 (29.2); 2.496 (20.5); 2.491 (9.2); 2.105 (7.5); 0.000 (0.6)

Example 4-5

$^1$H-NMR (400.0 MHz, d$_6$-DMSO): δ=11.292 (1.3); 7.894 (0.8); 7.757 (0.6); 7.736 (1.0); 7.704 (1.5); 7.683 (0.7); 5.751 (0.9); 4.182 (1.9); 4.165 (6.3); 4.147 (6.4); 4.130 (2.0); 3.764 (15.2); 3.310 (73.9); 2.523 (1.0); 2.518 (1.5); 2.510 (19.0); 2.505 (40.9); 2.500 (56.8); 2.496 (39.8); 2.491 (18.0); 2.107 (12.9); 2.072 (3.4); 1.266 (7.3); 1.249 (16.0); 1.231 (7.1); 0.000 (0.7)

Example 4-8

$^1$H-NMR (400.0 MHz, d$_6$-DMSO): δ=3.486 (16.0); 2.522 (0.9); 2.517 (1.3); 2.513 (0.9)

Example 4-9

$^1$H-NMR (400.0 MHz, d$_6$-DMSO): δ=11.313 (1.8); 7.893 (0.9); 7.797 (0.7); 7.776 (1.2); 7.732 (1.6); 7.711 (0.9); 4.836 (1.5); 4.813 (5.0); 4.791 (5.2); 4.768 (1.8); 3.765 (16.0); 3.361 (0.7); 3.309 (100.1); 2.669 (0.6); 2.523 (1.7); 2.518 (2.6); 2.509 (30.1); 2.505 (64.1); 2.500 (89.2); 2.496 (62.4); 2.491 (27.7); 2.327 (0.6); 2.186 (15.5); 0.000 (1.0)

Example 4-15

$^1$H-NMR (400.0 MHz, CDCl$_3$): δ=8.113 (2.3); 8.093 (2.6); 7.818 (1.6); 7.798 (1.4); 7.588 (1.0); 7.261 (28.3); 3.997 (16.0); 3.872 (11.6); 3.245 (15.1); 2.242 (12.8); 0.000 (10.4)

Example 4-19

$^1$H-NMR (400.0 MHz, CDCl$_3$): δ=8.130 (2.3); 8.110 (2.6); 7.806 (2.1); 7.786 (2.1); 7.778 (2.6); 7.261 (49.3); 4.248 (0.8); 4.232 (2.5); 4.231 (2.6); 4.214 (2.6); 4.196 (0.9); 3.928 (12.8); 3.241 (16.0); 2.250 (14.3); 1.353 (4.7); 1.335 (10.0); 1.317 (4.6); 0.008 (0.5); 0.000 (18.0); −0.009 (0.6)

Example 4-22

$^1$H-NMR (400.0 MHz, d$_6$-DMSO): δ=8.098 (0.6); 8.078 (0.9); 8.043 (0.5); 8.023 (1.5); 7.991 (0.9); 7.934 (0.7); 5.751 (11.1); 3.968 (2.9); 3.959 (0.9); 3.951 (3.2); 3.935 (0.5); 3.784 (16.0); 3.337 (9.8); 3.312 (2.3); 2.523 (0.7); 2.510 (13.1); 2.505 (27.5); 2.501 (37.4); 2.496 (26.5); 2.492 (12.3); 2.161 (4.1); 2.135 (2.8); 1.146 (0.8); 1.126 (0.5); 0.541 (1.7); 0.537 (1.9); 0.530 (1.3); 0.521 (1.9); 0.517 (1.7); 0.509 (0.8); 0.301 (0.7); 0.290 (1.9); 0.279 (2.0); 0.267 (0.7); 0.000 (1.3)

Example 4-74

$^1$H-NMR (400.0 MHz, d$_6$-DMSO): δ=11.231 (1.1); 8.312 (4.4); 7.964 (0.8); 7.944 (1.2); 7.900 (0.9); 7.862 (0.8); 7.843 (0.6); 3.953 (2.9); 3.949 (3.0); 3.935 (3.0); 3.931 (2.9); 3.777 (11.4); 3.310 (41.3); 3.266 (15.3); 2.523 (0.7); 2.518 (1.1); 2.509 (16.1); 2.505 (35.6); 2.500 (49.9); 2.496 (35.1); 2.491 (15.9); 2.326 (10.5); 2.141 (16.0); 1.164 (0.6); 1.161 (0.5); 1.156 (0.5); 1.144 (1.0); 1.132 (0.6); 1.126 (0.5); 1.124 (0.6); 0.540 (0.5); 0.535 (2.2); 0.531 (2.6); 0.526 (1.0); 0.519 (0.9); 0.515 (2.5); 0.510 (2.3); 0.505 (0.7); 0.499 (0.6); 0.293 (1.0); 0.286 (1.3); 0.282 (2.1); 0.277 (2.0); 0.274 (1.5); 0.270 (2.5); 0.265 (1.5); 0.259 (0.9); 0.000 (10.9)

Example 4-136

$^1$H-NMR (400.0 MHz, d$_6$-DMSO): δ=11.226 (0.7); 7.963 (0.7); 7.943 (1.0); 7.902 (0.7); 7.862 (0.6); 3.900 (2.3); 3.895 (2.4); 3.882 (2.5); 3.878 (2.3); 3.776 (10.5); 3.310 (19.3); 3.246 (12.2); 2.518 (0.7); 2.509 (9.0); 2.505 (19.7); 2.500 (27.5); 2.496 (19.1); 2.491 (8.5); 2.317 (8.1); 2.140 (12.4); 1.974 (0.8); 1.957 (1.0); 1.940 (0.8); 0.932 (16.0); 0.916 (15.4); 0.000 (15.2)

Example 5-1

$^1$H-NMR (400.0 MHz, d$_6$-DMSO): δ=11.843 (1.1); 7.723 (10.6); 5.751 (4.3); 3.905 (16.0); 3.309 (19.5); 2.510 (5.6); 2.505 (12.0); 2.501 (16.5); 2.496 (11.5); 2.491 (5.1); 2.110 (14.7); 2.072 (1.1)

Example 5-5

$^1$H-NMR (400.0 MHz, d$_6$-DMSO): δ=11.839 (1.2); 7.718 (12.5); 4.184 (1.2); 4.166 (3.9); 4.149 (4.0); 4.131 (1.2); 3.310 (40.6); 2.523 (0.5); 2.518 (0.8); 2.510 (9.2); 2.505 (19.6); 2.501 (27.2); 2.496 (18.8); 2.491 (8.4); 2.112 (16.0); 1.266 (4.4); 1.248 (9.9); 1.231 (4.3)

Example 5-8

$^1$H-NMR (400.0 MHz, d$_6$-DMSO): δ=3.472 (16.0); 2.522 (0.9); 2.517 (1.3); 2.513 (0.9)

Example 5-9

$^1$H-NMR (400.0 MHz, d$_6$-DMSO): δ=11.855 (1.3); 7.775 (0.7); 7.754 (6.1); 7.749 (6.1); 7.728 (0.7); 4.836 (0.8); 4.814 (2.5); 4.791 (2.6); 4.768 (0.9); 3.309 (38.4); 2.523 (0.6); 2.518 (0.9); 2.510 (10.3); 2.505 (21.9); 2.501 (30.6); 2.496 (21.5); 2.491 (9.6); 2.192 (16.0)

Example 5-15

$^1$H-NMR (400.0 MHz, CDCl$_3$): δ=8.073 (1.1); 8.053 (1.4); 7.840 (0.8); 7.820 (0.6); 7.262 (18.3); 3.831 (13.3); 3.079 (16.0); 2.514 (8.6); 2.467 (0.6); 2.302 (10.6); 1.581 (1.2); 0.000 (7.1)

Example 5-22

$^1$H-NMR (400.0 MHz, d$_6$-DMSO): δ=11.987 (2.2); 8.115 (3.4); 8.095 (4.7); 7.988 (4.3); 7.967 (3.3); 3.968 (3.1); 3.951 (3.3); 3.344 (15.8); 3.308 (33.4); 2.523 (0.7); 2.518 (1.0); 2.510 (12.9); 2.505 (28.0); 2.500 (39.1); 2.496 (27.5); 2.491 (12.4); 2.162 (16.0); 1.144 (0.9); 1.124 (0.5); 0.542 (1.8); 0.538 (2.1); 0.530 (1.0); 0.527 (0.7); 0.521 (2.0); 0.517 (1.8); 0.510 (0.5); 0.507 (0.5); 0.300 (0.8); 0.290 (1.9); 0.286 (1.5); 0.278 (1.9); 0.274 (1.2); 0.266 (0.6); 0.000 (2.2)

Example 5-67

$^1$H-NMR (400.0 MHz, CDCl$_3$): δ=7.840 (0.9); 7.819 (1.1); 7.677 (1.9); 7.656 (1.5); 7.261 (36.6); 3.956 (16.0); 3.191 (14.4); 2.428 (9.7); 2.161 (12.2); 1.591 (2.5); 0.000 (13.6)

Example 5-71

$^1$H-NMR (400.0 MHz, CDCl$_3$): δ=7.851 (1.1); 7.831 (1.0); 7.681 (2.0); 7.668 (0.7); 7.661 (1.6); 7.261 (43.5); 3.956 (16.0); 3.808 (4.6); 3.192 (14.7); 3.034 (4.4); 2.429 (10.7); 2.371 (3.2); 2.232 (3.5); 2.160 (11.8); 1.603 (3.4); 0.008 (0.6); 0.000 (16.9)

Example 5-74

$^1$H-NMR (400.0 MHz, d$_6$-DMSO): δ=11.803 (1.7); 7.983 (1.6); 7.981 (1.6); 7.962 (2.1); 7.961 (2.1); 7.830 (2.5); 7.809 (1.9); 4.038 (0.5); 4.021 (0.5); 3.954 (2.1); 3.949 (2.2); 3.936 (2.2); 3.931 (2.1); 3.310 (33.4); 3.272 (14.0); 2.523 (0.7); 2.518 (1.0); 2.510 (12.1); 2.505 (26.1); 2.500 (36.1); 2.496 (25.1); 2.491 (11.2); 2.313 (10.5); 2.145 (16.0); 1.988 (2.5); 1.193 (0.8); 1.175 (1.6); 1.157 (0.9); 1.141 (0.8); 0.858 (0.9); 0.534 (1.7); 0.530 (2.0); 0.526 (0.8); 0.519 (0.7); 0.514 (1.8); 0.510 (1.7); 0.292 (0.8); 0.285 (1.0); 0.281 (1.6); 0.276 (1.5); 0.273 (1.1); 00.269 (1.8); 0.264 (1.1); 0.258 (0.7); 0.000 (16.7)

Example 6-1

$^1$H-NMR (400.0 MHz, d$_6$-DMSO): δ=11.503 (0.9); 7.768 (0.7); 7.747 (2.1); 7.726 (3.1); 7.705 (1.1); 3.904 (16.0); 3.309 (36.0); 2.523 (0.6); 2.518 (0.9); 2.510 (11.4); 2.505 (24.6); 2.500 (34.2); 2.496 (23.7); 2.491 (10.5); 2.387 (18.8); 2.110 (12.6); 2.072 (5.8); 0.000 (0.6)

Example 6-5

$^1$H-NMR (400.0 MHz, d$_6$-DMSO): δ=11.500 (1.4); 7.763 (1.0); 7.742 (2.8); 7.722 (4.1); 7.702 (1.4); 4.183 (1.4); 4.165 (4.6); 4.148 (4.7); 4.130 (1.4); 3.307 (23.9); 2.523 (0.9); 2.518 (1.3); 2.509 (15.4); 2.505 (32.8); 2.500 (45.4); 2.496 (31.5); 2.491 (14.1); 2.387 (23.6); 2.111 (16.0); 1.266 (5.2); 1.248 (11.6); 1.230 (5.1); 0.008 (1.1); 0.000 (33.7); −0.009 (0.9)

Example 6-8

$^1$H-NMR (400.0 MHz, d$_6$-DMSO): δ=11.500 (1.3); 7.761 (1.0); 7.740 (3.0); 7.720 (4.2); 7.700 (1.4); 3.966 (2.9); 3.949 (2.9); 3.309 (49.4); 2.523 (0.8); 2.518 (1.1); 2.510 (13.2); 2.505 (27.7); 2.500 (38.2); 2.496 (26.7); 2.491 (11.9); 2.386 (23.5); 2.129 (16.0); 2.072 (0.7); 1.163 (0.5); 1.143 (0.9); 1.122 (0.5); 0.542 (0.7); 0.532 (2.1); 0.527 (2.2); 0.522 (1.0); 0.517 (1.0); 0.511 (2.3); 0.507 (2.0); 0.497 (0.9); 0.306 (0.9); 0.296 (2.4); 0.292 (2.4); 0.284 (2.1); 0.280 (2.5); 0.269 (0.6)

Example 6-9

$^1$H-NMR (400.0 MHz, d$_6$-DMSO): δ=11.519 (1.2); 7.802 (1.2); 7.781 (2.6); 7.751 (3.9); 7.730 (1.7); 4.836 (0.9); 4.813 (2.9); 4.790 (3.0); 4.768 (1.0); 3.309 (53.9); 2.523 (0.9); 2.518 (1.2); 2.510 (13.7); 2.505 (29.1); 2.501 (40.3); 2.496 (28.2); 2.491 (12.6); 2.386 (24.4); 2.191 (16.0)

Example 6-15

$^1$H-NMR (400.0 MHz, d$_6$-DMSO): δ=11.638 (1.5); 8.116 (1.5); 8.096 (2.3); 8.028 (1.5); 8.008 (1.0); 5.753 (0.7); 3.918 (16.0); 3.349 (13.6); 3.311 (30.4); 2.510 (17.4); 2.505 (33.0); 2.501 (43.3); 2.496 (30.8); 2.492 (14.9); 2.400 (19.6); 2.327 (0.6); 2.146 (9.4); 0.000 (2.9)

Example 6-19

$^1$H-NMR (400.0 MHz, CDCl$_3$): δ=8.070 (1.5); 8.050 (1.9); 7.849 (1.0); 7.829 (0.8); 7.263 (32.8); 4.238 (0.9); 4.220 (3.1); 4.203 (3.3); 4.185 (1.1); 3.236 (16.0); 2.510 (13.1); 2.233 (12.6); 1.572 (4.3); 1.346 (4.4); 1.328 (9.3); 1.310 (4.2); 0.000 (12.7)

Example 6-22

$^1$H-NMR (400.0 MHz, d$_6$-DMSO): δ=11.640 (2.7); 8.112 (2.6); 8.092 (4.1); 8.022 (2.6); 8.002 (1.7); 5.751 (12.4); 3.968 (4.8); 3.951 (5.3); 3.341 (37.1); 3.337 (39.9); 2.523 (1.6); 2.509 (24.3); 2.505 (50.1); 2.500 (68.0); 2.496 (48.4); 2.491 (23.0); 2.399 (35.3); 2.163 (16.0); 1.164 (0.8); 1.162 (0.8); 1.156 (0.8); 1.152 (0.6); 1.144 (1.4); 1.136 (0.7); 1.132 (0.8); 1.126 (0.8); 1.124 (0.9); 0.552 (0.7); 0.550 (0.8); 0.541 (3.1); 0.537 (3.4); 0.530 (1.7); 0.527 (1.4); 0.521 (3.2); 0.517 (3.1); 0.509 (1.0); 0.507 (0.9); 0.300 (1.3); 0.289 (3.3); 0.285 (2.8); 0.278 (3.3); 0.274 (2.2); 0.266 (1.1); 0.000 (2.3)

Example 6-67

$^1$H-NMR (400.0 MHz, CDCl$_3$): δ=7.903 (0.9); 7.882 (1.0); 7.691 (1.4); 7.670 (1.1); 7.261 (42.6); 3.960 (16.0); 3.199 (14.3); 2.509 (14.4); 2.427 (8.8); 2.175 (13.3); 1.643 (1.2); 0.000 (16.2)

Example 6-71

$^1$H-NMR (400.0 MHz, CDCl$_3$): δ=8.375 (0.9); 7.889 (1.6); 7.869 (2.0); 7.684 (2.0); 7.663 (1.7); 7.261 (38.3); 4.215 (1.4); 4.197 (4.2); 4.179 (4.3); 4.162 (1.5); 3.184 (15.8); 2.509 (16.0); 2.419 (11.8); 2.175 (16.0); 1.602 (2.6); 1.332 (4.5); 1.314 (9.1); 1.297 (4.4); 0.008 (1.1); 0.000 (13.9); −0.008 (0.8)

Example 6-74

$^1$H-NMR (400.0 MHz, d$_6$-DMSO): δ=11.453 (1.5); 8.312 (4.2); 7.974 (1.4); 7.973 (1.4); 7.954 (2.0); 7.953 (2.0); 7.854 (1.9); 7.834 (1.3); 3.953 (2.1); 3.948 (2.2); 3.935 (2.2); 3.930 (2.1); 3.309 (28.5); 3.269 (14.0); 2.523 (0.7); 2.518 (1.1); 2.510 (13.5); 2.505 (29.3); 2.500 (40.7); 2.496 (28.3); 2.491 (12.6); 2.395 (22.6); 2.306 (10.2); 2.144 (16.0); 1.141 (0.8); 0.534 (1.7); 0.530 (2.0); 0.526 (0.8); 0.519 (0.7); 0.514 (1.9); 0.510 (1.8); 0.291 (0.7); 0.285 (1.0); 0.281 (1.6); 0.276 (1.5); 0.273 (1.1); 0.269 (1.8); 0.264 (1.1); 0.258 (0.7); 0.008 (0.9); 0.000 (31.0); −0.009 (0.9)

Example 7-1

$^1$H-NMR (400.0 MHz, d$_6$-DMSO): δ=7.695 (2.9); 7.691 (3.2); 3.900 (16.0); 3.308 (7.7); 2.518 (0.7); 2.510 (7.8); 2.505 (16.5); 2.500 (22.8); 2.496 (15.9); 2.491 (7.3); 2.481 (8.7); 2.098 (14.2); 0.008 (0.5); 0.000 (17.7); −0.009 (0.5)

Example 7-5

¹H-NMR (400.0 MHz, d₆-DMSO): δ=7.690 (3.3); 7.687 (3.5); 4.178 (1.2); 4.161 (4.1); 4.143 (4.1); 4.126 (1.3); 3.306 (17.8); 2.523 (0.7); 2.518 (1.0); 2.509 (11.9); 2.505 (25.5); 2.500 (35.5); 2.496 (24.7); 2.491 (11.2); 2.480 (9.0); 2.100 (16.0); 1.262 (4.7); 1.245 (10.6); 1.227 (4.5); 0.000 (15.1)

Example 7-8

¹H-NMR (400.0 MHz, d₆-DMSO): δ=7.705 (3.7); 7.702 (3.9); 3.978 (3.7); 3.961 (3.7); 3.329 (51.6); 2.540 (0.6); 2.535 (1.0); 2.526 (12.8); 2.522 (27.3); 2.517 (38.1); 2.512 (26.7); 2.508 (12.1); 2.496 (9.9); 2.133 (16.0); 1.156 (0.8); 0.556 (0.6); 0.545 (1.8); 0.541 (2.0); 0.536 (0.9); 0.531 (0.9); 0.525 (2.0); 0.521 (1.8); 0.510 (0.8); 0.320 (0.8); 0.310 (2.1); 0.306 (2.1); 0.298 (1.8); 0.294 (2.2); 0.283 (0.5)

Example 7-9

¹H-NMR (400.0 MHz, d₆-DMSO): δ=12.301 (0.6); 7.749 (0.6); 7.728 (2.3); 7.716 (2.6); 7.695 (0.6); 4.833 (0.8); 4.810 (2.6); 4.788 (2.7); 4.765 (0.9); 3.309 (42.2); 2.523 (1.1); 2.518 (1.6); 2.510 (17.3); 2.505 (36.2); 2.501 (49.7); 2.496 (34.7); 2.491 (15.8); 2.480 (9.3); 2.179 (16.0); 0.000 (0.9)

Example 7-15

¹H-NMR (400.0 MHz, CDCl₃): δ=8.080 (1.7); 8.060 (2.0); 7.840 (1.6); 7.820 (1.3); 7.261 (33.6); 3.816 (16.0); 3.081 (15.6); 2.525 (12.3); 2.321 (14.6); 1.286 (0.8); 1.256 (0.7); 0.000 (13.1)

Example 7-19

¹H-NMR (400.0 MHz, CDCl₃): δ=8.100 (1.1); 8.080 (1.3); 7.880 (1.0); 7.859 (0.8); 7.260 (74.5); 4.235 (0.7); 4.234 (0.7); 4.218 (2.3); 4.216 (2.3); 4.200 (2.4); 4.199 (2.3); 4.182 (0.8); 3.234 (14.8); 2.526 (12.2); 2.248 (16.0); 1.343 (4.4); 1.326 (9.4); 1.308 (4.2); 0.008 (1.0); 0.000 (28.6); −0.009 (0.7)

Example 7-22

¹H-NMR (400.0 MHz, d₆-DMSO): δ=12.441 (0.9); 8.083 (1.7); 8.063 (2.4); 8.043 (1.4); 8.022 (3.0); 7.991 (2.7); 7.970 (2.4); 7.968 (2.0); 7.947 (1.4); 3.966 (3.2); 3.961 (3.6); 3.948 (3.6); 3.943 (3.5); 3.935 (1.4); 3.378 (0.6); 3.333 (22.7); 3.323 (18.8); 3.312 (14.4); 2.523 (1.8); 2.518 (2.7); 2.510 (29.3); 2.505 (60.1); 2.500 (81.6); 2.496 (58.6); 2.491 (29.8); 2.327 (0.5); 2.149 (16.0); 2.134 (9.3); 1.880 (0.8); 1.161 (0.7); 1.159 (0.8); 1.154 (0.8); 1.149 (0.8); 1.141 (1.3); 1.137 (0.9); 1.129 (0.9); 1.124 (0.9); 1.121 (0.9); 0.547 (0.8); 0.539 (2.7); 0.534 (3.7); 0.530 (2.3); 0.527 (2.1); 0.519 (3.1); 0.514 (3.4); 0.298 (1.2); 0.286 (3.4); 0.283 (3.3); 0.275 (3.4); 0.264 (1.1); 0.000 (3.3)

Example 7-71

¹H-NMR (400.0 MHz, CDCl₃): δ=8.120 (1.4); 8.099 (2.4); 8.052 (1.9); 8.051 (1.9); 8.031 (1.1); 8.030 (1.1); 7.261 (34.5); 4.237 (1.1); 4.219 (3.5); 4.201 (3.7); 4.184 (1.2); 3.208 (15.5); 2.561 (10.1); 2.229 (16.0); 1.350 (4.3); 1.333 (9.1); 1.315 (4.2); 0.000 (12.8)

Example 7-74

¹H-NMR (400.0 MHz, d₆-DMSO): δ=8.312 (5.3); 7.947 (1.5); 7.927 (1.9); 7.799 (1.5); 7.778 (1.1); 3.951 (2.0); 3.942 (2.1); 3.933 (2.2); 3.925 (2.0); 3.311 (32.9); 3.262 (13.8); 3.246 (1.5); 2.523 (0.8); 2.518 (1.2); 2.510 (15.0); 2.505 (32.5); 2.500 (45.2); 2.496 (31.7); 2.491 (14.9); 2.486 (13.2); 2.373 (1.1); 2.279 (8.3); 2.133 (16.0); 2.116 (1.7); 1.139 (0.8); 0.532 (1.8); 0.528 (2.1); 0.523 (0.9); 0.516 (0.8); 0.512 (1.9); 0.507 (1.9); 0.289 (0.8); 0.282 (1.1); 0.278 (1.8); 0.273 (1.7); 0.270 (1.3); 0.267 (2.1); 0.262 (1.2); 0.255 (0.7); 0.000 (8.8)

Example 8-5

¹H-NMR (400.0 MHz, CDCl₃): δ=8.163 (2.1); 8.142 (2.5); 7.873 (1.9); 7.852 (1.6); 7.261 (38.1); 4.141 (12.7); 3.823 (15.7); 3.100 (16.0); 2.340 (13.5); 1.285 (0.5); 0.000 (14.4)

Example 8-25

¹H-NMR (400.0 MHz, CDCl₃): δ=8.092 (1.1); 8.071 (1.3); 7.886 (1.4); 7.866 (1.2); 7.260 (51.7); 7.256 (0.6); 4.129 (9.3); 3.816 (16.0); 3.064 (15.6); 2.422 (9.1); 2.293 (14.5); 0.008 (0.6); 0.000 (19.5); −0.009 (0.5)

Example 8-26

¹H-NMR (400.0 MHz, CDCl₃): δ=8.090 (1.1); 8.070 (1.3); 7.855 (1.2); 7.835 (1.0); 7.268 (0.6); 7.267 (0.6); 7.2663 (0.7); 7.2655 (0.9); 7.260 (90.0); 7.253 (0.6); 5.299 (1.3); 4.135 (9.1); 4.122 (0.8); 4.113 (1.4); 4.095 (1.4); 4.090 (0.6); 4.078 (0.5); 4.072 (1.4); 4.054 (1.4); 4.045 (0.7); 4.028 (0.7); 3.085 (16.0); 3.063 (1.8); 2.430 (1.2); 2.409 (9.1); 2.284 (15.5); 2.263 (1.7); 2.005 (13.3); 1.197 (4.1); 1.185 (0.7); 1.179 (8.7); 1.168 (1.1); 1.162 (4.0); 0.008 (1.1); 0.008 (1.1); 0.005 (0.5); 0.000 (34.5); −0.009 (0.9)

Example 9-5

¹H-NMR (400.0 MHz, CDCl₃): δ=8.149 (2.1); 8.128 (2.5); 7.858 (1.7); 7.838 (1.5); 7.262 (25.9); 4.530 (0.8); 4.512 (2.7); 4.493 (2.8); 4.475 (0.9); 3.984 (1.4); 3.817 (15.6); 3.267 (1.3); 3.098 (16.0); 2.338 (12.6); 2.258 (1.1); 1.652 (3.5); 1.642 (0.5); 1.633 (8.0); 1.624 (0.8); 1.615 (3.5); 0.000 (9.7)

Example 9-25

¹H-NMR (400.0 MHz, CDCl₃): δ=8.081 (1.6); 8.061 (2.0); 7.870 (1.8); 7.849 (1.5); 7.262 (36.1); 4.507 (1.0); 4.489 (3.0); 4.471 (3.1); 4.453 (1.0); 3.966 (0.6); 3.815 (16.0); 3.064 (15.7); 2.420 (11.4); 2.291 (15.0); 2.200 (0.6); 1.661 (3.7); 1.642 (8.0); 1.624 (3.6); 0.000 (13.5)

Example 10-5

¹H-NMR (400.0 MHz, CDCl₃): δ=8.150 (2.0); 8.130 (2.3); 7.852 (2.0); 7.832 (1.7); 7.261 (29.5); 4.452 (1.4); 4.434 (2.2); 4.415 (1.4); 3.820 (16.0); 3.097 (15.6); 2.337 (13.9); 2.065 (1.1); 2.047 (2.0); 2.028 (2.1); 2.010 (1.2);

1.285 (0.8); 1.256 (0.7); 1.020 (1.0); 1.012 (3.8); 1.003 (1.2); 0.994 (7.7); 0.975 (3.6); 0.000 (11.0)

Example 11-5

$^1$H-NMR (400.0 MHz, CDCl$_3$): δ=8.117 (2.4); 8.097 (2.7); 7.782 (1.7); 7.762 (1.6); 7.406 (0.8); 7.262 (22.7); 3.887 (12.1); 3.851 (16.0); 3.100 (16.0); 2.324 (13.8); 0.000 (8.4)

Example 12-25

$^1$H-NMR (400.0 MHz, CDCl$_3$): δ=7.840 (0.9); 7.819 (1.1); 7.677 (1.9); 7.656 (1.5); 7.261 (36.6); 3.956 (16.0); 3.191 (14.4); 2.428 (9.7); 2.161 (12.2); 1.591 (2.5); 00.000 (13.6)

Example 12-26

1H-NMR (400.0 MHz, CDCl$_3$): δ=8.371 (0.6); 7.871 (1.1); 7.850 (1.4); 7.675 (1.8); 7.654 (1.5); 7.262 (33.5); 4.133 (0.7); 4.116 (0.7); 4.106 (1.4); 4.089 (1.4); 4.058 (1.4); 4.040 (1.4); 4.031 (0.7); 4.013 (0.7); 3.056 (16.0); 2.365 (10.6); 2.209 (13.5); 1.627 (1.5); 1.195 (4.2); 1.178 (8.9); 1.160 (4.0); 0.000 (13.0)

Example 13-5

$^1$H-NMR (400.0 MHz, CDCl$_3$): δ=8.073 (1.1); 8.053 (1.4); 7.840 (0.8); 7.820 (0.6); 7.262 (18.3); 3.831 (13.3); 3.079 (16.0); 2.514 (8.6); 2.467 (0.6); 2.302 (10.6); 1.581 (1.2); 0.000 (7.1)

Example 13-25

$^1$H-NMR (400.0 MHz, CDCl$_3$): δ=7.932 (1.1); 7.912 (1.3); 7.685 (1.3); 7.665 (1.1); 7.261 (37.8); 3.812 (16.0); 3.040 (15.5); 2.514 (10.8); 2.372 (9.0); 2.242 (13.9); 1.607 (0.8); 0.000 (13.7)

Example 13-26

$^1$H-NMR (400.0 MHz, CDCl$_3$): δ=8.275 (0.9); 7.930 (1.7); 7.910 (1.9); 7.683 (1.8); 7.663 (1.5); 7.261 (35.5); 4.136 (0.8); 4.127 (0.6); 4.119 (0.9); 4.109 (1.5); 4.101 (0.5); 4.092 (1.5); 4.080 (0.7); 4.074 (0.7); 4.063 (1.5); 4.053 (0.6); 4.045 (1.6); 4.036 (0.9); 4.028 (0.6); 4.018 (0.8); 3.062 (16.0); 2.516 (12.0); 2.364 (11.9); 2.231 (15.0); 1.599 (1.7); 1.200 (4.4); 1.182 (8.7); 1.165 (4.2); 0.000 (12.9); −0.008 (0.8)

Example 14-5

$^1$H-NMR (400.0 MHz, CDCl$_3$): δ=8.080 (1.7); 8.060 (2.0); 7.840 (1.5); 7.820 (1.3); 7.261 (33.6); 3.816 (16.0); 3.081 (15.6); 2.525 (12.3); 2.321 (14.6); 1.286 (0.7); 1.256 (0.7); 0.000 (13.1)

B. Formulation Examples a) A dusting product is obtained by mixing 10 parts by weight of a compound of the formula (I) and 90 parts by weight of talc as inert substance and comminuting the mixture in a hammer mill.
b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.
c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.
d) An emulsifiable concentrate is obtained from 15 parts by weight of a compound of the formula (I), 75 parts by weight of cyclohexanone as solvent and 10 parts by weight of oxyethylated nonylphenol as emulsifier.
e) Water-dispersible granules are obtained by mixing
75 parts by weight of a compound of the formula (I) and/or salts thereof,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spray application of water as a granulating liquid.
f) Water-dispersible granules are also obtained by homogenizing and precomminuting, in a colloid mill,
25 parts by weight of a compound of the formula (I),
5 parts by weight of sodium 2,2'-dinaphthylmethane-6,6'-disulfonate
2 parts by weight of sodium oleoylmethyltaurate,
1 part by weight of polyvinyl alcohol
17 parts by weight of calcium carbonate and
50 parts by weight of water,
then grinding the mixture in a bead mill and atomizing and drying the resulting suspension in a spray tower by means of a one-phase nozzle.

C. Biological Examples

1. Pre-Emergence Herbicidal Action Against Harmful Plants
Seeds of monocotyledonous and dicotyledonous weed plants and crop plants are laid out in wood-fiber pots in sandy loam and covered with soil. The compounds of the invention, formulated in the form of wettable powders (WP) or as emulsion concentrates (EC), are then applied to the surface of the covering soil in the form of an aqueous suspension or emulsion at a water application rate equating to 600 to 800 l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). In this case, for example, compound Nos. 1-15, 1-71, 1-74, 2-15, 2-19, 2-67, 2-71, 2-74, 2-136, 3-15, 3-19, 4-74, 5-15, 5-67, 5-71, 5-74, 6-15, 6-19, 6-67, 6-71, 6-74, 7-15, 7-19, 7-71, 7-74, 8-1, 8-25, 9-5, 9-25, 10-5 and 12-25, at an application rate of 320 g/ha, each show at least 80% efficacy against *Abutilon theophrasti* and *Veronica persica*.
2. Post-Emergence Herbicidal Action Against Harmful Plants
Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 I/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). In this case, for example, compound Nos. 1-15, 1-71, 1-74, 2-15, 2-19, 2-67, 2-71, 2-74, 2-136, 3-15, 3-19, 4-19, 4-136, 5-15, 7-15, 7-19, 7-74, 8-1, 8-25, 8-26, 9-5, 9-25, 10-5 and 10-5, at an application rate of 80 g/ha, each show at least 80% efficacy against *Abutilon theophrasti* and *Veronica persica*.

3. Comparative Experiments

In addition, comparative tests were conducted under the conditions specified above on different harmful plants between inventive compounds and the most structurally similar known compounds from WO 2013/064459 A1 (D1). The results listed in the tables which follow show the superiority of these compounds of the invention.

The abbreviations used here mean:

| | | | |
|---|---|---|---|
| ALOMY | *Alopecurus myosuroides* | AVEFA | *Avena fatua* |
| CYPES | *Cyperus esculentus* | ECHCG | *Echinochloa crus galli* |
| MATIN | *Matricaria inodora* | POLCO | *Polygonum convolvulus* |
| STEME | *Stellaria media* | VIOTR | *Viola tricolor* |
| a.i. | active ingredient | | |

Pre-Emergence Comparative Tests

| Compound No. | Dosage [g a.i./ha] | Herbicidal efficacy against | | |
|---|---|---|---|---|
| | | AVEFA | CYPES | VIOTR |
| 1-5, inventive | 320 | 90% | 90% | 100% |
| 1-2, from D1 | 320 | 0% | 40% | 0% |

| Compound No. | Dosage [g a.i./ha] | Herbicidal efficacy against | | |
|---|---|---|---|---|
| | | AVEFA | STEME | VIOTR |
| 1-8, inventive | 320 | 90% | 100% | 100% |
| 1-4, from D1 | 320 | 0% | 20% | 50% |

| Compound No. | Dosage [g a.i./ha] | Herbicidal efficacy against | | |
|---|---|---|---|---|
| | | AVEFA | CYPES | VIOTR |
| 2-1, inventive | 320 | 100% | 100% | 100% |
| 1-40, from D1 | 320 | 50% | 30% | 50% |

| Compound No. | Dosage [g a.i./ha] | Herbicidal efficacy against | | |
|---|---|---|---|---|
| | | AVEFA | CYPES | VIOTR |
| 3-1, inventive | 320 | 80% | 100% | 100% |
| 1-79, from D1 | 320 | 50% | 30% | 40% |

| Compound No. | Dosage [g a.i./ha] | Herbicidal efficacy against | | |
|---|---|---|---|---|
| | | AVEFA | STEME | VIOTR |
| 3-5, inventive | 320 | 70% | 100% | 100% |
| 1-80, from D1 | 320 | 10% | 60% | 20% |

| Compound No. | Dosage [g a.i./ha] | Herbicidal efficacy against | | |
|---|---|---|---|---|
| | | CYPES | ECHCG | VIOTR |
| 3-19, inventive | 80 | 80% | 90% | 100% |
| 1-93, from D1 | 80 | 20% | 40% | 20% |

| Compound No. | Dosage [g a.i./ha] | Herbicidal efficacy against | | |
|---|---|---|---|---|
| | | ECHCG | STEME | VIOTR |
| 4-5, inventive | 320 | 90% | 80% | 100% |
| 2-2, from D1 | 320 | 0% | 40% | 0% |

| Compound No. | Dosage [g a.i./ha] | Herbicidal efficacy against | | |
|---|---|---|---|---|
| | | ECHCG | POLCO | STEME |
| 6-1, inventive | 320 | 60% | 40% | 60% |
| 3-1, from D1 | 320 | 0% | 0% | 0% |

| Compound No. | Dosage [g a.i./ha] | Herbicidal efficacy against | | |
|---|---|---|---|---|
| | | AVEFA | CYPES | VIOTR |
| 6-19, inventive | 320 | 30% | 80% | 100% |
| 3-15, from D1 | 320 | 0% | 20% | 60% |

| Compound No. | Dosage [g a.i./ha] | Herbicidal efficacy against | | |
|---|---|---|---|---|
| | | AVEFA | POLCO | VIOTR |
| 10-6, inventive | 320 | 40% | 60% | 100% |
| 1-93, from D1 | 320 | 0% | 20% | 30% |

| Compound No. | Dosage [g a.i./ha] | Herbicidal efficacy against | | |
|---|---|---|---|---|
| | | AVEFA | CYPES | VIOTR |
| 13-6, inventive | 320 | 60% | 60% | 100% |
| 3-15, from D1 | 320 | 0% | 20% | 60% |

Post-Emergence Comparative Tests

| Compound No. | Dosage [g a.i./ha] | Herbicidal efficacy against | |
|---|---|---|---|
| | | MATIN | VIOTR |
| 1-5, inventive | 20 | 90% | 90% |
| 1-2, from D1 | 20 | 60% | 60% |

| Compound No. | Dosage [g a.i./ha] | Herbicidal efficacy against ALOMY | MATIN |
|---|---|---|---|
| 1-8, inventive | 80 | 70% | 100% |
| 1-4, from D1 | 80 | 10% | 70% |

| Compound No. | Dosage [g a.i./ha] | Herbicidal efficacy against ALOMY | VIOTR |
|---|---|---|---|
| 2-1, inventive | 80 | 60% | 100% |
| 1-40, from D1 | 80 | 40% | 60% |

| Compound No. | Dosage [g a.i./ha] | Herbicidal efficacy against MATIN | VIOTR |
|---|---|---|---|
| 3-1, inventive | 20 | 80% | 100% |
| 1-79, from D1 | 20 | 60% | 30% |

| Compound No. | Dosage [g a.i./ha] | Herbicidal efficacy against MATIN | VIOTR |
|---|---|---|---|
| 3-5, inventive | 80 | 90% | 100% |
| 1-80, from D1 | 80 | 60% | 60% |

| Compound No. | Dosage [g a.i./ha] | Herbicidal efficacy against MATIN | VIOTR |
|---|---|---|---|
| 3-8, inventive | 80 | 70% | 80% |
| 1-82, from D1 | 80 | 20% | 20% |

| Compound No. | Dosage [g a.i./ha] | Herbicidal efficacy against MATIN | VIOTR |
|---|---|---|---|
| 3-15, inventive | 20 | 90% | 90% |
| 1-92, from D1 | 20 | 70% | 60% |

| Compound No. | Dosage [g a.i./ha] | Herbicidal efficacy against ALOMY | VIOTR |
|---|---|---|---|
| 3-19, inventive | 80 | 50% | 100% |
| 1-93, from D1 | 80 | 0% | 80% |

| Compound No. | Dosage [g a.i./ha] | Herbicidal efficacy against ALOMY | VIOTR |
|---|---|---|---|
| 4-5, inventive | 80 | 30% | 90% |
| 2-2, from D1 | 80 | 0% | 40% |

| Compound No. | Dosage [g a.i./ha] | Herbicidal efficacy against ALOMY | VIOTR |
|---|---|---|---|
| 4-19, inventive | 20 | 80% | 100% |
| 2-15, from D1 | 20 | 40% | 80% |

| Compound No. | Dosage [g a.i./ha] | Herbicidal efficacy against MATIN | VIOTR |
|---|---|---|---|
| 6-15, inventive | 80 | 80% | 100% |
| 3-14, from D1 | 80 | 0% | 60% |

| Compound No. | Dosage [g a.i./ha] | Herbicidal efficacy against MATIN | VIOTR |
|---|---|---|---|
| 6-19, inventive | 80 | 70% | 100% |
| 3-15, from D1 | 80 | 30% | 60% |

| Compound No. | Dosage [g a.i./ha] | Herbicidal efficacy against ALOMY | MATIN |
|---|---|---|---|
| 10-5, inventive | 80 | 60% | 100% |
| 1-92, from D1 | 80 | 10% | 80% |

| Compound No. | Dosage [g a.i./ha] | Herbicidal efficacy against MATIN | VIOTR |
|---|---|---|---|
| 10-6, inventive | 20 | 90% | 100% |
| 1-93, from D1 | 20 | 40% | 60% |

| Compound No. | Dosage [g a.i./ha] | Herbicidal efficacy against MATIN | VIOTR |
|---|---|---|---|
| 13-5, inventive | 80 | 60% | 90% |
| 3-14, from D1 | 80 | 0% | 60% |

| Compound No. | Dosage [g a.i./ha] | Herbicidal efficacy against MATIN | VIOTR |
|---|---|---|---|
| 13-6, inventive | 80 | 60% | 100% |
| 3-14, from D1 | 80 | 30% | 60% |

The invention claimed is:

1. A substituted ketoxime benzoylamide of formula (I)

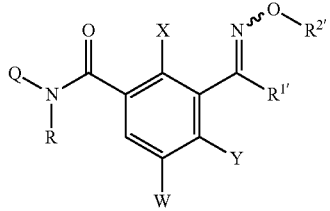

in which
Q is a Q1, Q2, Q3 or Q4 radical

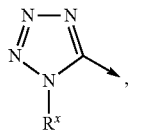

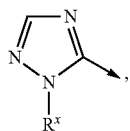

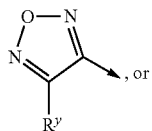

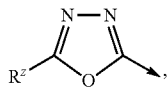

R is hydrogen, $(C_1-C_6)$-alkyl, halo-$(C_1-C_6)$-alkyl, $(C_2$-$C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3$-$C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1O)C$—$(C_1$-$C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $R^1O)CO$—$(C_1-C_6)$-alkyl, $R^1O(O)C$—O—$(C_1$-$C_6)$-alkyloxy, $R^2(O)_2SO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S$(R)N—$(C_1-C_6)$-alkyl, $R^2(O)_nS$—$(C_1-C_6)$-alkyl, $R^1O$$(O)_2S$—$(C_1-C_6)$-alkyl, $(R^1)_2N(O)_2S$—$(C_1-C_6)$-alkyl, $R^1(O)C$, $R^1O(O)C$, $(R^1)_2N(O)C$, $R^{10}$, $(R^1)_2N$, $R^1O(O)C(R^1)N$, $(R^1)_2N(O)C(R^1)N$, $R^2(O)_2S$, or benzyl substituted in each case by s radicals selected from the group consisting of methyl, ethyl, methoxy, nitro, trifluoromethyl and halogen, $R^1$ is hydrogen, $(C_1-C_6)$-alkyl, halo-$(C_1-C_6)$-alkyl, $(C_2$-$C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1$-$C_6)$-alkyl, heteroaryl-O—$(C_1-C_6)$-alkyl, heterocyclyl-O—$(C_1-C_6)$-alkyl, phenyl-N$(R^3)$—$(C_1-C_6)$-alkyl, heteroaryl-N$(R^3)$—$(C_1-C_6)$-alkyl, heterocyclyl-N$(R^3)$—$(C_1-C_6)$-alkyl, phenyl-S(O)$_n$—$(C_1-C_6)$-alkyl, heteroaryl-S(O)$_n$—$(C_1-C_6)$-alkyl or heterocyclyl-S(O)$_n$—$(C_1-C_6)$-alkyl, where the fifteen latter radicals are each substituted by s radicals selected from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1-C_6)$-alkyl, and where heterocyclyl bears n oxo groups, $R^2$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N$(R^3)$—$(C_1-C_6)$-alkyl, heteroaryl-N$(R^3)$—$(C_1-C_6)$-alkyl, heterocyclyl-N$(R^3)$—$(C_1-C_6)$-alkyl, phenyl-S(O)$_n$—$(C_1-C_6)$-alkyl, heteroaryl-S(O)$_n$—$(C_1-C_6)$-alkyl or heterocyclyl-S(O)$_n$—$(C_1-C_6)$-alkyl, where the fifteen latter radicals are each substituted by s radicals selected from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O$$(O)_2S$, $(R^3)_2N(O)_2S$ and $R^3O$—$(C_1-C_6)$-alkyl, and where heterocyclyl bears n oxo groups, $R^3$ is hydrogen, $(C_1-C_6)$-alkyl, halo-$(C_1-C_6)$-alkyl, $(C_2$-$C_6)$-alkenyl, $(C_2-C_6)$-alkynyl, $(C_3-C_6)$-cycloalkyl, $(C_3$-$C_6)$-cycloalkyl-$(C_1-C_6)$-alkyl or phenyl, $R^4$ is $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^5$ is hydrogen or $(C_1-C_4)$-alkyl, $R^6$ is $(C_1-C_4)$-alkyl, $R^7$ is acetoxy, acetamido, N-methylacetamido, benzoyloxy, benzamido, N-methyl-benzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, methylsulfenyl, methylsulfinyl, methylsulfonyl, $(C_3-C_6)$-cycloalkyl, or heteroaryl or heterocyclyl each substituted by s radicals selected from the group consisting of methyl, ethyl, methoxy, trifluoromethyl and halogen, $R^8$ is $(C_1-C_6)$-alkyl, halo-$(C_1-C_6)$-alkyl, $(C_1-C_6)$-alkyl-O—$(C_1-C_6)$-alkyl, $(C_2-C_6)$-alkenyl or $(C_3-C_6)$-alkynyl, $R^9$ is $(C_1-C_6)$-alkyl, halo-$(C_1-C_6)$-alkyl, $(C_2-C_6)$-alkenyl or $(C_3-C_6)$-alkynyl, $R^{10}$ is hydrogen, $(C_1-C_6)$-alkyl, halo-$(C_1-C_6)$-alkyl, $(C_2$-$C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^{11}$ is $(C_1-C_6)$-alkyl, $(C_2-C_6)$-alkenyl or $(C_2-C_6)$-alkynyl, $R^{1'}$ is cyano, $(C_1-C_6)$-alkyl, $(C_3-C_6)$-cycloalkyl, halo-$(C_1$-$C_6)$-alkyl, $OR^8$, $SR^8$, or $NR^8R^9$, $R^{2'}$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, or $(C_3-C_6)$-cycloalkyl-$(C_1-C_6)$-alkyl, where the last six radicals are each substituted by s radicals selected from the group consisting of cyano, halogen, nitro, thiocyanato, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1-C_4)$-alkoxy- ($C_2$-$C_6$)-alkoxycarbonyl; or is phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-$NR^{10}$-heteroaryl, or ($C_1$-$C_6$)-alkyl-$NR^{10}$-heterocyclyl, where the ten latter radicals are each substituted by s radicals selected from the group consisting of cyano, halogen, nitro, thiocyanato, ($C_1$-$C_6$)-alkyl, halo-($C_1$-$C_6$)-alkyl, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and ($C_1$-$C_4$)-alkoxy-($C_2$-$C_6$)-alkoxycarbonyl, and where heterocyclyl bears n oxo groups, $R^X$ is ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, or halo-($C_3$-$C_6$)-alkynyl, where the six aforementioned radicals are each substituted by s radicals selected from the group consisting of nitro, cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, ($C_3$-$C_6$)-cycloalkyl, heteroaryl, heterocyclyl and phenyl, where the four latter radicals themselves are in turn substituted by s radicals selected from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl bears n oxo groups; or is ($C_3$-$C_7$)-cycloalkyl, heteroaryl, heterocyclyl or phenyl, where the four aforementioned radicals are each substituted by s radicals selected from the group consisting of halogen, nitro, cyano, ($C_1$-$C_6$)-alkyl, halo-($C_1$-$C_6$)-alkyl, ($C_3$-$C_6$)-cycloalkyl, ($C_1$-$C_6$)-alkyl-$S(O)_n$, ($C_1$-$C_6$)-alkoxy, halo-($C_1$-$C_6$)-alkoxy and ($C_1$-$C_6$)-alkoxy-($C_1$-$C_4$)-alkyl, $R^Y$ is hydrogen, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_7$)-cycloalkyl, ($C_1$-$C_6$)-alkoxy, halo-($C_1$-$C_6$)-alkoxy, ($C_2$-$C_6$)-alkenyloxy, ($C_2$-$C_6$)-alkynyloxy, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonyl-methyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by s radicals selected from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl bears n oxo groups, $R^Z$ is hydrogen, ($C_1$-$C_6$)-alkyl, $R^1O$—($C_1$-$C_6$)-alkyl, $R^7CH_2$, ($C_3$-$C_7$)-cycloalkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, $R^1O$, $R^1(H)N$, methoxycarbonyl, ethoxycarbonyl, methylcarbonyl, dimethylamino, trifluoromethylcarbonyl, acetylamino, methylsulfenyl, methyl-sulfinyl, methylsulfonyl, or heteroaryl, heterocyclyl, benzyl or phenyl each substituted by s radicals selected from the group consisting of halogen, nitro, cyano, ($C_1$-$C_6$)-alkyl, halo-($C_1$-$C_6$)-alkyl, ($C_3$-$C_6$)-cycloalkyl, ($C_1$-$C_6$)-alkyl-$S(O)_n$, ($C_1$-$C_6$)-alkoxy, halo-($C_1$-$C_6$)-alkoxy and ($C_1$-$C_6$)-alkoxy-($C_1$-$C_4$)-alkyl, where heterocyclyl bears n oxo groups, W is hydrogen, halogen, nitro, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_7$)-cycloalkyl, halo-($C_3$-$C_7$)-cycloalkyl, ($C_1$-$C_6$)-alkoxy, halo-($C_1$-$C_6$)-alkoxy, ($C_1$-$C_6$)-alkyl-$(O)_nS$—, ($C_1$-$C_6$)-haloalkyl-$(O)_nS$—, ($C_1$-$C_6$)-alkoxy-($C_1$-$C_4$)-alkyl, ($C_1$-$C_6$)-alkoxy-($C_1$-$C_4$)-haloalkyl, $R^1(O)C$, $R^1(R^1ON=)C$, $R^1O(O)C$, $(R^1)_2N$, $R^1(O)C(R^1)N$ or $R^2(O)_2S(R^1)N$, X is nitro, halogen, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^1O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^1O(O)CO$, $(R^1)_2N(O)CO$, $(R^1)_2N$, $R^1(O)C(R^1)N$, $R^2(O)_2S(R^1)N$, $R^1O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1O(O)C(R^1)N(O)_2S$, $R^1O(O)C(R^1)N(O)_2S$, $(R^1)_2N(O)C(R^1)N(O)_2S$, $(R^5O)_2(O)P$, $R^1(O)C$—($C_1$-$C_6$)-alkyl, $R^1O(O)C$—($C_1$-$C_6$)-alkyl, $(R^1)_2N(O)C$—($C_1$-$C_6$)-alkyl, $R^1O(R^1)N(O)C$—($C_1$-$C_6$)-alkyl, $(R^1)_2N(R^1)N(O)C$—($C_1$-$C_6$)-alkyl, $R^1(O)C(R^1)N(O)C$—($C_1$-$C_6$)-alkyl, $R^1O(O)C(R^1)N(O)C$—($C_1$-$C_6$)-alkyl, $(R^1)_2N(O)C(R^1)N(O)C$—($C_1$-$C_6$)-alkyl, $R^2(O)_2S(R^1)N(O)C$—($C_1$-$C_6$)-alkyl, $R^1O(O)_2S(R^1)N(O)C$—($C_1$-$C_6$)-alkyl, $(R^1)_2N(O)_2S(R^1)N(O)C$—($C_1$-$C_6$)-alkyl, NC—($C_1$-$C_6$)-alkyl, $R^{10}$—($C_1$-$C_6$)-alkyl, $R^1(O)CO$—($C_1$-$C_6$)-alkyl, $R^2(O)_2SO$—($C_1$-$C_6$)-alkyl, $R^1O(O)CO$—($C_1$-$C_6$)-alkyl, $(R^1)_2N(O)CO$—($C_1$-$C_6$)-alkyl, $(R^1)_2N$—($C_1$-$C_6$)-alkyl, $R^1(O)C(R^1)N$—($C_1$-$C_6$)-alkyl, $R^2(O)_2S(R^1)N$—($C_1$-$C_6$)-alkyl, $R^1O(O)C(R^1)N$—($C_1$-$C_6$)-alkyl, $(R^1)_2N(O)C(R^1)N$—($C_1$-$C_6$)-alkyl, $R^1O(O)_2S(R^1)N$—($C_1$-$C_6$)-alkyl, $(R^1)_2N(O)_2S(R^1)N$—($C_1$-$C_6$)-alkyl, $R^2(O)_nS$—($C_1$-$C_6$)-alkyl, $R^1O(O)_2S$—($C_1$-$C_6$)-alkyl, $(R^1)_2N(O)_2S$—($C_1$-$C_6$)-alkyl, $R^1(O)C(R^1)N(O)_2S$—($C_1$-$C_6$)-alkyl, $R^1O(O)C(R^1)N(O)_2S$—($C_1$-$C_6$)-alkyl, $(R^1)_2N(O)C(R^1)N(O)_2S$—($C_1$-$C_6$)-alkyl, $(R^5O)_2(O)P$—($C_1$-$C_6$)-alkyl, phenyl, heteroaryl, heterocyclyl, phenyl-($C_1$-$C_6$)-alkyl, heteroaryl-($C_1$-$C_6$)-alkyl, or heterocyclyl-($C_1$-$C_6$)-alkyl, where the six latter radicals are each substituted by s radicals selected from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—($C_1$-$C_6$)-alkyl, and where heterocyclyl bears n oxo groups, Y is hydrogen, nitro, halogen, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^1O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^1O(O)CO$, $(R^1)_2N(O)CO$, $(R^1)_2N$, $R^1(O)C(R^1)N$, $R^2(O)_2S(R^1)N$, $R^1O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^1O(O)C(R^1)N(O)_2S$, $(R^1)_2N(O)C(R^1)N(O)_2S$, $(R^5O)_2(O)P$, $R^1(O)C$—($C_1$-$C_6$)-alkyl, $R^1O(O)C$—($C_1$-$C_6$)-alkyl, $(R^1)_2N(O)C$—($C_1$-$C_6$)-alkyl, $R^1O(R^1)N(O)C$—($C_1$-$C_6$)-alkyl, $(R^1)_2N(R^1)N(O)C$—($C_1$-$C_6$)-alkyl, $R^1(O)C(R^1)N(O)C$—($C_1$-$C_6$)-alkyl, $R^1O(O)C(R^1)N(O)C$—($C_1$-$C_6$)-alkyl, $(R^1)_2N(O)C(R^1)N(O)$ C—$(C_1$-$C_6)$-alkyl, $R^2(O)_2S(R^1)N(O)C$—$(C_1$-$C_6)$-alkyl, $R^1O(O)_2S(R^1)N(O)C$—$(C_1$-$C_6)$-alkyl, $(R^1)_2N(O)_2S(R^1)N(O)C$—$(C_1$-$C_6)$-alkyl, NC—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^1O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^1O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C(R^1)N(O)_2S$—$(C_1$-$C_6)$-alkyl, $R^1O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, or heterocyclyl-$(C_1$-$C_6)$-alkyl, where the six latter radicals are each substituted by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl bears n oxo groups, n is 0, 1 or 2, and s is 0, 1, 2 or 3.

2. A substituted ketoxime benzoylamide of formula (I) as claimed in claim 1, in which Q is a Q1, Q2, Q3 or Q4 radical

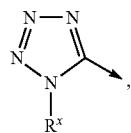 (Q1)

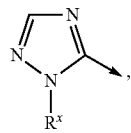 (Q2)

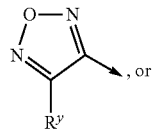 (Q3)

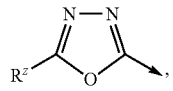 (Q4)

R is hydrogen, $(C_1$-$C_6)$-alkyl, halo-$(C_1$-$C_6)$-alkyl, $R^1(O)C$—$(C_1$-$C_6)$-alkyl, $R^1O(O)C$—$(C_1$-$C_6)$-alkyl, $R^1O(O)C$—O—$(C_1$-$C_6)$-alkyloxy, $R^1O$—$(C_1$-$C_6)$-alkyl, $R^1(O)C$, $R^1O(O)C$, $R^1O$, $R^2(O)_2S$, or benzyl substituted in each case by s radicals selected from the group consisting of methyl, ethyl, methoxy, nitro, trifluoromethyl and halogen, $R^1$ is hydrogen, $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkenyl, $(C_1$-$C_6)$-alkyl-O—$(C_1$-$C_6)$-alkyl, phenyl, heteroaryl or heterocyclyl, where the three latter radicals are each substituted by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1$-$C_6)$-alkyl, and where heterocyclyl bears n oxo groups, $R^2$ is $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, $(C_1$-$C_6)$-alkyl-O—$(C_1$-$C_6)$-alkyl, phenyl, heteroaryl or heterocyclyl, where the three latter radicals are each substituted by s radicals selected from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1$-$C_6)$-alkyl, and where heterocyclyl bears n oxo groups, $R^3$ is hydrogen, $(C_1$-$C_6)$-alkyl, halo-$(C_1$-$C_6)$-alkyl, $(C_3$-$C_6)$-cycloalkyl or phenyl, $R^4$ is $(C_1$-$C_6)$-alkyl, halo-$(C_1$-$C_6)$-alkyl, $(C_3$-$C_6)$-cycloalkyl or phenyl, $R^5$ is hydrogen or $(C_1$-$C_4)$-alkyl, $R^6$ is $(C_1$-$C_4)$-alkyl, $R^7$ is acetoxy, benzoyloxy, methoxycarbonyl, ethoxycarbonyl, methylcarbonyl, trifluoromethylcarbonyl, methylsulfenyl, methylsulfinyl, methylsulfonyl, $(C_3$-$C_6)$-cycloalkyl, or heteroaryl or heterocyclyl each substituted by s radicals selected from the group consisting of methyl, ethyl, methoxy, trifluoromethyl and halogen, $R^8$ is $(C_1$-$C_6)$-alkyl, halo-$(C_1$-$C_6)$-alkyl, $(C_1$-$C_6)$-alkyl-O—$(C_1$-$C_6)$-alkyl, $(C_2$-$C_6)$-alkenyl or $(C_3$-$C_6)$-alkynyl, $R^9$ is $(C_1$-$C_6)$-alkyl or halo-$(C_1$-$C_6)$-alkyl, $R^{10}$ is hydrogen, $(C_1$-$C_6)$-alkyl, halo-$(C_1$-$C_6)$-alkyl or $(C_3$-$C_6)$-cycloalkyl, $R^{11}$ is $(C_1$-$C_6)$-alkyl, $R^{1'}$ is $(C_1$-$C_6)$-alkyl, $(C_3$-$C_6)$-cycloalkyl, halo-$(C_1$-$C_6)$-alkyl, $OR^8$, $SR^8$, $NR^8R^9$, $R^{2'}$ is hydrogen, $(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkenyl, $(C_3$-$C_6)$-cycloalkyl-$(C_1$-$C_6)$-alkyl, where the last six radicals are each substituted by s radicals from the group consisting of cyano, halogen, $OR^{10}$, $S(O)_nR^{11}$, $N(R^{10})_2$, $COR^{10}$, $CO_2R^{10}$ and $(C_1$-$C_4)$-alkoxy-$(C_2$-$C_6)$-alkoxycarbonyl; or is phenyl, heteroaryl, or heterocyclyl, where the three latter radicals are each substituted by s radicals selected from the group consisting of cyano, halogen, nitro, thiocyanato, $(C_1$-$C_6)$-alkyl, halo-$(C_1$-$C_6)$-alkyl, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1$-$C_4)$-alkoxy-$(C_2$-$C_6)$-alkoxycarbonyl, and where heterocyclyl bears n oxo groups, $R^x$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, where the five aforementioned radicals are each substituted by s radicals selected from the group consisting of cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)CO$, $(C_3$-$C_6)$-cycloalkyl, heteroaryl, heterocyclyl and phenyl, where the four latter radicals themselves are in turn substituted by s radicals selected from the group consisting of $(C_1$-$C_6)$-alkyl, halo-$(C_1$-$C_6)$-alkyl, $(C_1$-$C_6)$-alkoxy, halo-$(C_1$-$C_6)$-alkoxy and halogen, and where heterocyclyl bears n oxo group; or is $(C_3$-$C_7)$-cycloalkyl, heteroaryl, heterocyclyl or phenyl, where the four aforementioned radicals are each substituted by s radicals selected from the group consisting of halogen, nitro, cyano, $(C_1$-$C_6)$-alkyl, halo-$(C_1$-$C_6)$-alkyl, $(C_3$-$C_6)$-cycloalkyl, $(C_1$-$C_6)$-alkyl-$S(O)_n$, $(C_1$-$C_6)$-alkoxy, halo-$(C_1$-$C_6)$-alkoxy and $(C_1$-$C_6)$-alkoxy-$(C_1$-$C_4)$-alkyl, $R^Y$ is hydrogen, $(C_1-C_6)$-alkyl, halo-$(C_1-C_6)$-alkyl, $(C_2-C_6)$-alkenyl, $(C_2-C_6)$-alkynyl, $(C_3-C_7)$-cycloalkyl, $(C_1-C_6)$-alkoxy, cyano, methylsulfenyl, methylsulfinyl, methylsulfonyl, acetylamino, methoxycarbonyl, ethoxycarbonyl, methoxy-carbonylmethyl, ethoxycarbonylmethyl, benzoyl, methylcarbonyl, trifluoro-methylcarbonyl, halogen, amino, methylaminocarbonyl, dimethylaminocarbonyl, methoxymethyl, or heteroaryl, heterocyclyl or phenyl each substituted by s radicals selected from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl bears n oxo groups, $R^Z$ is hydrogen, $(C_1-C_6)$-alkyl, $R^1O$—$(C_1-C_6)$-alkyl, $R^7CH_2$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, $R^1O$, $R^1(H)N$, methoxycarbonyl, ethoxycarbonyl, methylcarbonyl, dimethylamino, trifluoro-methylcarbonyl, acetylamino, methylsulfenyl, methylsulfinyl, methylsulfonyl, or heteroaryl, heterocyclyl, benzyl or phenyl each substituted by s radicals selected from the group consisting of halogen, cyano, $(C_1-C_6)$-alkyl, halo-$(C_1-C_6)$-alkyl, $(C_3-C_6)$-cycloalkyl, $(C_1-C_6)$-alkyl-$S(O)_n$, $(C_1-C_6)$-alkoxy, halo-$(C_1-C_6)$-alkoxy and $(C_1-C_6)$-alkoxy-$(C_1-C_4)$-alkyl, where heterocyclyl bears n oxo groups, W is hydrogen, halogen, $(C_1-C_6)$-alkyl, halo-$(C_1-C_6)$-alkyl, $(C_2-C_6)$-alkenyl, $(C_2-C_6)$-alkynyl, $(C_3-C_7)$-cycloalkyl, $(C_1-C_6)$-alkoxy, halo-$(C_1-C_6)$-alkoxy, $(C_1-C_6)$-alkyl-$(O)_nS$—, $(C_1-C_6)$-alkoxy-$(C_1-C_4)$-alkyl, $(C_1-C_6)$-alkoxy-$(C_1-C_4)$-haloalkyl, $R^1(O)C$, $(R^1)_2N$, $R^1(O)C(R^1)N$ or $R^2(O)_2S(R^1)N$, X is nitro, halogen, cyano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $R(O)CO$, $R^1O(O)CO$, $(R^1)_2N$, $R^1(O)C(R)N$, $R^2(O)_2S(R^1)N$, $R^1O(O)C(R^1)N$, $R^2(O)_nS$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $NC$—$(C_1-C_6)$-alkyl, $R^1O$—$(C_1-C_6)$-alkyl, $R^1(O)CO$—$(C_1-C_6)$-alkyl, $R^2(O)_2SO$—$(C_1-C_6)$-alkyl, $R^1O(O)CO$—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^1O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $(R^5O)_2(O)P$—$(C_1-C_6)$-alkyl, phenyl, heteroaryl or heterocyclyl, where the three latter radicals are each substituted by s radicals selected from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1$, $R^1(O)CO$, $R^2(O)_2SO$, $R^1O(O)CO$, $(R^1)_2N(O)CO$, $(R^1)_2N$, $R^1(O)C(R^1)N$, $R^2(O)_2S(R^1)N$, $R^1O(O)C(R^1)N$, $R^2(O)_nS$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $NC$—$(C_1-C_6)$-alkyl, $R^1O$—$(C_1-C_6)$-alkyl, $R(O)CO$—$(C_1-C_6)$-alkyl, $R^2(O)_2SO$—$(C_1-C_6)$-alkyl, $R^1O(O)CO$—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^1O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $(R^5O)_2(O)P$—$(C_1-C_6)$-alkyl, phenyl, heteroaryl, or heterocyclyl, where the three latter radicals are each substituted by s radicals selected from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, n is 0, 1 or 2, and s is 0, 1, 2 or 3.

3. A substituted ketoxime benzoylamide of formula (I) as claimed in claim 1, in which Q is a Q1, Q2, Q3 or Q4 radical

(Q1)

(Q2)

(Q3)

(Q4)

R is hydrogen, $(C_1-C_6)$-alkyl, halo-$(C_1-C_6)$-alkyl, $R^1(O)C$—$(C_1-C_6)$-alkyl, $R^1O(O)C$—$O$—$(C_1-C_6)$-alkyloxy, $R^1(O)C$, $R^1O(O)C$ or $R^2(O)_2S$, $R^1$ is hydrogen, $(C_1-C_6)$-alkyl, halo-$(C_1-C_6)$-alkyl, $(C_3-C_6)$-cycloalkyl, $(C_1-C_6)$-alkyl-$O$—$(C_1-C_6)$-alkyl, phenyl, heteroaryl or heterocyclyl, where the three latter radicals are each substituted by s radicals selected from the group consisting of halogen, $(C_1-C_6)$-alkyl, halo-$(C_1-C_6)$-alkyl and $R^3O(O)C$, and where heterocyclyl bears n oxo groups, $R^2$ is $(C_1-C_6)$-alkyl, halo-$(C_1-C_6)$-alkyl, $(C_3-C_6)$-cycloalkyl, $(C_1-C_6)$-alkyl-$O$—$(C_1-C_6)$-alkyl, phenyl, heteroaryl or heterocyclyl, where the three latter radicals are each substituted by s radicals selected from the group consisting of halogen, $(C_1-C_6)$-alkyl, halo-$(C_1-C_6)$-alkyl, $R^3O(O)C$, $R^3O$, $R^4(O)_nS$ and $R^3O$—$(C_1-C_6)$-alkyl, and where heterocyclyl bears n oxo groups, $R^3$ is hydrogen, $(C_1-C_6)$-alkyl or halo-$(C_1-C_6)$-alkyl, $R^4$ is $(C_1-C_6)$-alkyl or halo-$(C_1-C_6)$-alkyl, $R^5$ is hydrogen or $(C_1-C_4)$-alkyl, $R^6$ is $(C_1-C_4)$-alkyl, $R^7$ is acetoxy, methylsulfenyl or $(C_3-C_6)$-cycloalkyl, $R^8$ is $(C_1-C_6)$-alkyl or halo-$(C_1-C_6)$-alkyl,
$R^9$ is $(C_1-C_6)$-alkyl,
$R^{10}$ is hydrogen, $(C_1-C_6)$-alkyl or halo-$(C_1-C_6)$-alkyl,
$R^{11}$ is $(C_1-C_6)$-alkyl,
$R^{1'}$ is $(C_1-C_6)$-alkyl, $(C_3-C_6)$-cycloalkyl, halo-$(C_1-C_6)$-alkyl, $OR^8$, $SR^8$, $NR^8R^9$,
$R^{2'}$ is hydrogen, $(C_1-C_6)$-alkyl, $(C_3-C_6)$-cycloalkyl, or $(C_3-C_6)$-cycloalkyl-$(C_1-C_6)$-alkyl, where the last three radicals are each substituted by s radicals selected from the group consisting of cyano, halogen, $OR^{10}$, $S(O)_nR^{11}$, $N(R^{10})_2$, $COR^{10}$, $CO_2R^{10}$ and $(C_1-C_4)$-alkoxy-$(C_2-C_6)$-alkoxycarbonyl; or is phenyl, heteroaryl, or heterocyclyl, where the three latter radicals are each substituted by s radicals selected from the group consisting of cyano, halogen, $(C_1-C_6)$-alkyl, halo-$(C_1-C_6)$-alkyl, $OR^{10}$, $S(O)_nR^{11}$, $N(R^{10})_2$, $COR^{10}$ and $CO_2R^{10}$, and where heterocyclyl bears n oxo groups,
$R^x$ is $(C_1-C_6)$-alkyl, halo-$(C_1-C_6)$-alkyl, $(C_2-C_6)$-alkenyl, or $(C_2-C_6)$-alkynyl, where the four aforementioned radicals are each substituted by s radicals selected from the group consisting of cyano, $(R^6)_3Si$, $(R^5O)_2(O)P$, $R^2(O)_nS$, $(R^1)_2N$, $R^1O$, $R^1(O)C$, $R^1O(O)C$, $(C_3-C_6)$-cycloalkyl, heteroaryl, heterocyclyl and phenyl, where the four latter radicals are in turn substituted by s radicals selected from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl bears n oxo groups; or is $(C_3-C_7)$-cycloalkyl, heteroaryl, heterocyclyl or phenyl, where the four aforementioned radicals are each substituted by s radicals selected from the group consisting of halogen, cyano, $(C_1-C_6)$-alkyl, halo-$(C_1-C_6)$-alkyl, $(C_3-C_6)$-cycloalkyl, $(C_1-C_6)$-alkyl-$S(O)_n$, $(C_1-C_6)$-alkoxy, halo-$(C_1-C_6)$-alkoxy and $(C_1-C_6)$-alkoxy-$(C_1-C_4)$-alkyl,
$R^Y$ is hydrogen, $(C_1-C_6)$-alkyl, halo-$(C_1-C_6)$-alkyl, $(C_2-C_6)$-alkenyl, $(C_2-C_6)$-alkynyl, $(C_3-C_7)$-cycloalkyl, $(C_1-C_6)$-alkoxy, methylsulfenyl, methylsulfinyl, methylsulfonyl, acetylamino, methoxycarbonyl, ethoxycarbonyl, methoxycarbonylmethyl, ethoxycarbonylmethyl, benzoyl, methylcarbonyl, trifluoromethylcarbonyl, halogen, methoxymethyl, or phenyl substituted in each case by s radicals selected from the group consisting of $(C_1-C_6)$-alkyl, halo-$(C_1-C_6)$-alkyl, $(C_1-C_6)$-alkoxy, halo-$(C_1-C_6)$-alkoxy and halogen,
$R^Z$ is hydrogen, $(C_1-C_6)$-alkyl, $R^1O$—$(C_1-C_6)$-alkyl, $R^7CH_2$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, $R^1O$, $R^1(H)N$, methoxycarbonyl, ethoxycarbonyl, methylcarbonyl, dimethylamino, trifluoro-methylcarbonyl, acetylamino, methylsulfenyl, methylsulfinyl, methylsulfonyl, or phenyl substituted in each case by s radicals selected from the group consisting of halogen, cyano, $(C_1-C_6)$-alkyl, halo-$(C_1-C_6)$-alkyl, $(C_3-C_6)$-cycloalkyl, $(C_1-C_6)$-alkyl-$S(O)_n$, $(C_1-C_6)$-alkoxy and halo-$(C_1-C_6)$-alkoxy,
W is hydrogen, halogen, $(C_1-C_6)$-alkyl, halo-$(C_1-C_6)$-alkyl, $(C_3-C_7)$-cycloalkyl, $(C_1-C_6)$-alkoxy, halo-$(C_1-C_6)$-alkoxy, $(C_1-C_6)$-alkyl-$S(O)_n$ or $(C_1-C_6)$-alkoxy-$(C_1-C_4)$-alkyl,
X is halogen, $(C_1-C_6)$-alkyl, halo-$(C_1-C_6)$-alkyl, $(C_3-C_6)$-cycloalkyl, $R^1(O)C$, $R^1O(O)C$, $(R^1)_2N(O)C$, $R^1O$, $(R^1)_2N$, $R^2(O)_nS$, $R^1O$—$(C_1-C_6)$-alkyl, $(R^1)_2N$—$(C_1-C_6)$-alkyl, $R^2(O)_nS$—$(C_1-C_6)$-alkyl, or phenyl, where the latter radical is substituted in each case by s radicals selected from the group consisting of halogen, $(C_1-C_6)$-alkyl, halo-$(C_1-C_6)$-alkyl, $R^1O(O)C$, $R^1O$, $(R^1)_2N$, $R^2(O)_nS$ and $R^1O$—$(C_1-C_6)$-alkyl,
Y is hydrogen, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, $R^1(O)C$, $R^1O(O)C$, $R^1O$, $(R^1)_2N$, $R^2(O)_nS$, $(R^5O)_2(O)P$, $R^1O$—$(C_1-C_6)$-alkyl, $(R^1)_2N$—$(C_1-C_6)$-alkyl, $R^2(O)_nS$—$(C_1-C_6)$-alkyl, or phenyl, where the latter radical is substituted in each case by s radicals selected from the group consisting of halogen, $(C_1-C_6)$-alkyl, halo-$(C_1-C_6)$-alkyl, $R^1O(O)C$, $R^1O$, $(R^1)_2N$, $R^2(O)_nS$ and $R^1O$—$(C_1-C_6)$-alkyl,
n is 0, 1 or 2, and
s is 0, 1, 2 or 3.

4. A substituted ketoxime benzoylamide of formula (I) as claimed in claim 1, in which Q is a Q1, Q2, Q3 or Q4 radical

(Q1)

(Q2)

(Q3)

(Q4)

R is hydrogen,
$R^{1'}$ is methyl, ethyl, trifluoromethyl or cyclopropyl,
$R^{2'}$ is methyl, ethyl, 2,2,2-trifluoroethyl, cyclopropylmethyl or trifluoromethyl,
$R^X$ is methyl, ethyl, propyl, methoxyethyl, 2-methoxy-2-methyl-1-propyl or phenyl,
$R^Y$ is chlorine, methyl or ethyl,
$R^Z$ is chlorine, methyl or ethyl,
X is fluorine, chlorine, bromine, methyl, methoxy, methylsulfonyl, methoxymethyl, methylsulfenyl, trifluoromethyl or cyclopropyl,
Y is chlorine, methyl, ethyl, cyclopropyl, allyl, vinyl, trifluoromethyl, difluoromethyl, chlorodifluoromethyl, pentafluoroethyl, methoxy, methylsulfenyl, methylsulfinyl, methylsulfonyl or ethylsulfonyl, and
W is hydrogen, fluorine, chlorine, methyl or trifluoromethyl.

5. A herbicidal composition comprising a herbicidally active content of at least one ketoxime benzoylamide of formula (I) as claimed in claim 1.

6. The herbicidal composition as claimed in claim 5 in a mixture with one or more formulation auxiliaries.

7. The herbicidal composition as claimed in claim 5, comprising at least one further pesticidally active substance from the group consisting of insecticides, acaricides, herbicides, fungicides, safeners, and growth regulators.

8. The herbicidal composition as claimed in claim 7, comprising a safener.

9. The herbicidal composition as claimed in claim 7, comprising a further herbicide.

10. A method of controlling one or more unwanted plants, which comprises applying an effective amount of at least one ketoxime benzoylamide of the formula (I) as claimed in claim 1 or of a herbicidal composition thereof to the plants or to a site of the unwanted vegetation.

11. A product comprising one or more ketoxime benzoylamides of formula (I) as claimed in claim 1 or a herbicidal composition thereof for controlling one or more unwanted plants.

12. The product as claimed in claim 11, wherein the ketoxime benzoylamides of formula (I) are used for controlling unwanted plants in crops of useful plants.

13. The product as claimed in claim 12, wherein the useful plants are transgenic useful plants.

14. A substituted ketoxime benzoylamide of formula (I) according to claim 1 in which Q is Q1

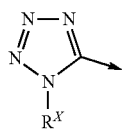

(Q1)

and R and W are each hydrogen,
wherein
(a) $R^X$ is methyl, X is Cl, Y is Cl, $R^{1'}$ is methyl, and $R^{2'}$ is ethyl;
(b) $R^X$ is methyl, X is Cl, Y is Cl, $R^{1'}$ is methyl, and $R^{2'}$ is —$CH_2$-cyclopropyl;
(c) $R^X$ is ethyl, X is Cl, Y is Cl, $R^{1'}$ is methyl, and $R^{2'}$ is methyl;
(d) $R^X$ is propyl, X is Cl, Y is Cl, $R^{1'}$ is methyl, and $R^{2'}$ is methyl;
(e) $R^X$ is propyl, X is Cl, Y is Cl, $R^{1'}$ is methyl, and $R^{2'}$ is ethyl;
(f) $R^X$ is propyl, X is Cl, Y is Cl, $R^{1'}$ is methyl, and $R^{2'}$ is —$CH_2$-cyclopropyl;
(g) $R^X$ is propyl, X is Cl, Y is —$SO_2$-methyl, $R^{1'}$ is methyl, and $R^{2'}$ is methyl; or
(f) $R^X$ is propyl, X is Cl, Y is —$SO_2$-methyl, $R^{1'}$ is methyl, and $R^{2'}$ is ethyl.

15. A substituted ketoxime benzoylamide of formula (I) according to claim 1 in which Q is Q2

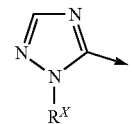

(Q2)

and R and W are each hydrogen,
wherein
(a) $R^X$ is methyl, X is Cl, Y is Cl, $R^{1'}$ is methyl, and $R^{2'}$ is ethyl; or
(b) $R^X$ is methyl, X is Cl, Y is —$SO_2$-methyl, $R^{1'}$ is methyl, and $R^{2'}$ is ethyl.

16. A substituted ketoxime benzoylamide of formula (I) according to claim 1 in which Q is Q3

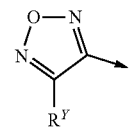

(Q3)

and R and W are each hydrogen,
wherein
(a) $R^X$ is methyl, X is Cl, Y is Cl, $R^{1'}$ is methyl, and $R^{2'}$ is methyl;
(b) $R^X$ is methyl, X is Cl, Y is —$SO_2$-methyl, $R^{1'}$ is methyl, and $R^{2'}$ is methyl; or
(c) $R^X$ is methyl, X is Cl, Y is —$SO_2$-methyl, $R^{1'}$ is methyl, and $R^{2'}$ is ethyl.

* * * * *